US012649021B2

(12) United States Patent
Pouchoulin

(10) Patent No.: US 12,649,021 B2
(45) Date of Patent: Jun. 9, 2026

(54) APPARATUS FOR EXTRACORPOREAL TREATMENT OF BLOOD INCLUDING CALCULATION OF PRE-BLOOD PUMP INFUSION FLOW RATE

(71) Applicant: GAMBRO LUNDIA AB, Lund (SE)

(72) Inventor: Dominique Pouchoulin, Tramoyes (FR)

(73) Assignee: GAMBRO LUNDIA AB, Lund (SE)

( * ) Notice: Subject to any disclaimer, the term of this patent is extended or adjusted under 35 U.S.C. 154(b) by 0 days.

(21) Appl. No.: 17/132,348

(22) Filed: Dec. 23, 2020

(65) Prior Publication Data

US 2021/0106738 A1 Apr. 15, 2021

Related U.S. Application Data

(63) Continuation of application No. 16/036,423, filed on Jul. 16, 2018, now Pat. No. 10,918,776, which is a
(Continued)

(30) Foreign Application Priority Data

Aug. 30, 2011 (EP) .................................... 11007041

(51) Int. Cl.
*A61M 1/16* (2006.01)
*A61M 1/34* (2006.01)
(Continued)

(52) U.S. Cl.
CPC ............ *A61M 1/1613* (2014.02); *A61M 1/16* (2013.01); *A61M 1/1601* (2014.02); *A61M 1/1605* (2014.02); *A61M 1/34* (2013.01);

*A61M 1/3403* (2014.02); *A61M 1/3406* (2014.02); *A61M 1/341* (2014.02); *A61M 1/342* (2013.01);
(Continued)

(58) Field of Classification Search
CPC .............................. A61M 1/1615; B01D 61/32
See application file for complete search history.

(56) References Cited

U.S. PATENT DOCUMENTS 4,731,731 A 3/1988 Cochran
5,366,630 A 11/1994 Chevallet
(Continued)

FOREIGN PATENT DOCUMENTS

DE 3442744 6/1986
DE 19928407 10/2000
(Continued)

OTHER PUBLICATIONS

B. Braun, "Diapact CRRT", Service Manual Edition Apr. 2003 Gebrauchsanweisung, IFU 38919907 Apr. 28, 2008, 470 pages.
(Continued)

*Primary Examiner* — Ryan B Huang
(74) *Attorney, Agent, or Firm* — K&L Gates LLP

(57) ABSTRACT

An apparatus for extracorporeal treatment of fluid and a process of setting up a medical apparatus for the delivery or collection of fluids are disclosed. According to the apparatus and the process, a control unit (10) is configured calculate set values of two or more of the fluid flow rates based on a fluid flow rate set by the operator and on a prescribed dose value ($D_{set}$).

21 Claims, 12 Drawing Sheets

Related U.S. Application Data continuation of application No. 14/342,025, filed as application No. PCT/IB2012/001620 on Aug. 23, 2012, now Pat. No. 10,052,423.

(51) Int. Cl.

| | |
|---|---|
| *A61M 1/36* | (2006.01) |
| *G01F 1/00* | (2022.01) |
| *G16H 20/17* | (2018.01) |
| *G16H 20/30* | (2018.01) |
| *G16Z 99/00* | (2019.01) |

(52) U.S. Cl.

CPC ........ *A61M 1/3434* (2014.02); *A61M 1/3437* (2014.02); *A61M 1/3451* (2014.02); *A61M 1/3607* (2014.02); *A61M 1/3609* (2014.02); *G01F 1/00* (2013.01); *G16H 20/17* (2018.01); *G16H 20/30* (2018.01); *G16Z 99/00* (2019.02); *A61M 1/3441* (2013.01); *A61M 2202/0413* (2013.01); *A61M 2205/3331* (2013.01); *A61M 2205/3334* (2013.01); *A61M 2205/3393* (2013.01); *A61M 2205/502* (2013.01); *A61M 2205/52* (2013.01); *A61M 2205/75* (2013.01)

(56) References Cited

U.S. PATENT DOCUMENTS

| | | | |
|---|---|---|---|
| 5,389,078 A | | 2/1995 | Zalesky et al. |
| 5,567,320 A | | 10/1996 | Goux et al. |
| 6,558,343 B1 | | 5/2003 | Neftel |
| 6,730,233 B2 | | 5/2004 | Pedrazzi et al. |
| 6,860,866 B1 | | 3/2005 | Graf et al. |
| 6,939,471 B2 | | 9/2005 | Gross et al. |
| 7,351,218 B2 | | 4/2008 | Bene |
| 7,563,240 B2 | | 7/2009 | Gross et al. |
| 8,216,478 B2 | | 7/2012 | Noack et al. |
| 8,512,271 B2 | | 8/2013 | Moissl et al. |
| 8,617,393 B2 | | 12/2013 | Remkes et al. |
| 8,668,825 B2 | | 3/2014 | Pouchoulin et al. |
| 8,900,172 B2 | | 12/2014 | Pohlmeier |
| 2002/0121471 A1 | | 9/2002 | Pedrazzi et al. |
| 2004/0182787 A1 | | 9/2004 | Chevallet |
| 2005/0070837 A1 | | 3/2005 | Ferrarini et al. |
| 2006/0054215 A1 | | 3/2006 | Remkes |
| 2006/0124548 A1 | | 6/2006 | Soichirou |
| 2006/0157413 A1 | | 7/2006 | Bene et al. |
| 2007/0062861 A1 | | 3/2007 | Lannoy |
| 2007/0066928 A1* | | 3/2007 | Lannoy ............... A61M 1/3609 |
| | | | 604/6.07 |
| 2008/0149551 A1 | | 6/2008 | Brugger |
| 2008/0154170 A1 | | 6/2008 | Lannoy |
| 2009/0221948 A1 | | 9/2009 | Szamosfalvi et al. |
| 2009/0276099 A1* | | 11/2009 | Fujii ................... A61M 1/3441 |
| | | | 700/282 |
| 2010/0168925 A1 | | 7/2010 | Hilgers et al. |
| 2011/0017667 A1 | | 1/2011 | Delmage |
| 2011/0037968 A1 | | 2/2011 | Li |
| 2015/0034536 A1 | | 2/2015 | Rada |

FOREIGN PATENT DOCUMENTS

| | | |
|---|---|---|
| DE | 10213179 | 8/2003 |
| DE | 10218846 | 9/2003 |
| DE | 10212247 | 12/2003 |
| DE | 10302691 | 4/2004 |
| DE | 60113624 | 6/2006 |
| DE | 102006032926 | 1/2008 |
| DE | 102006045437 | 4/2008 |
| DE | 60315118 | 9/2008 |
| DE | 102007052571 | 5/2009 |
| EP | 0658352 | 6/1995 |
| EP | 1348457 | 10/2003 |
| EP | 1430920 | 6/2004 |
| EP | 2163271 | 3/2010 |
| EP | 2324871 | 5/2011 |
| EP | 2433662 | 3/2012 |
| WO | 9716220 | 5/1997 |
| WO | 98023311 | 6/1998 |
| WO | 98050091 | 11/1998 |
| WO | 0176661 | 10/2001 |
| WO | 0195956 | 12/2001 |
| WO | 02062454 | 8/2002 |
| WO | 03028860 | 4/2003 |
| WO | 2005107833 | 11/2005 |
| WO | 2006011009 | 2/2006 |
| WO | 2007073739 | 7/2007 |
| WO | 2007140993 | 12/2007 |
| WO | 2008080055 | 7/2008 |
| WO | 2008135193 | 11/2008 |
| WO | 2009144522 | 12/2009 |
| WO | 2009147478 | 12/2009 |
| WO | 2010028860 | 3/2010 |
| WO | 2010029401 | 3/2010 |
| WO | 2010043593 | 4/2010 |

OTHER PUBLICATIONS

Kollbeck, T., B. Braun Sharing Expertise, Diapact CRRT Software Version 2.1 0.1/2.12.1, 12 pages.

Notice of Opposition—European Patent Office; Opposition against EP 2 433 662, Mar. 4, 2015, 60 pages.

European Search Report Appl. No. 17156418.0 dated Jun. 1, 2017—5 pages.

PRISMA System—Operator's Manual for use with Software versions R03.10; Gambro Dasco S.p.A.; Catalog No. 6983811, Rev. A; P/N 9032167800, Rev. A (Sep. 2006)—276 pages.

* cited by examiner

APPARATUS FOR EXTRACORPOREAL TREATMENT OF BLOOD INCLUDING CALCULATION OF PRE-BLOOD PUMP INFUSION FLOW RATE

PRIORITY CLAIM

The present application is a continuation of U.S. application Ser. No. 16/036,423 filed on Jul. 16, 2018, now issued U.S. Pat. No. 10,918,776, which is a continuation of U.S. application Ser. No. 14/342,025, filed on Jun. 3, 2014, now issued U.S. Pat. No. 10,052,423 issued on Aug. 21, 2018, which is a U.S. National Stage Application of International Application No. PCT/IB2012/001620, filed Aug. 23, 2012, which claims priority to European Patent Application No. 11007041.4, filed Aug. 30, 2011, the entire contents of each of which are incorporated herein by reference and relied upon.

BACKGROUND

The present invention relates to a medical apparatus for extracorporeal treatment of blood. The present invention also relates to a process of calculating set flow rates in a medical apparatus for delivery, collection or delivery and collection of fluids, such as for example in an apparatus for extracorporeal fluid processing.

In the field of biological fluid processing for medical use, several apparatuses are known which require manipulation of fluids of various nature. Known type of fluid processing system include extracorporeal blood treatment apparatus which are typically used to extract undesirable fluids and/or solutes from the patient's blood and/or add desirable fluids and/or substances to the blood. Extracorporeal blood treatment is used for treating patients unable to effectively remove excess water and undesirable particles from their blood, such as when a patient suffers temporary or permanent kidney failure. These patients may receive an extracorporeal blood treatment to add/or remove substances to their blood, to maintain an acid/base balance, and/or to remove excess body fluids, for example. Extracorporeal blood treatment is typically accomplished by removing the blood from the patient in e.g. a continuous flow, introducing the blood into a primary chamber, also referred to as blood chamber, of a filtration unit (such as a dialyzer or an hemofilter or an hemodiafilter) where the blood is allowed to flow along a semipermeable membrane. The semipermeable membrane selectively allows matter in the blood to cross the membrane from the primary chamber into a secondary chamber and also selectively allows matter in the secondary chamber to cross the membrane into the blood in the primary chamber, depending on the type of treatment. Cleared blood is then returned to the patient.

A number of different types of extracorporeal blood treatments may be performed. In an ultrafiltration (UF) treatment, undesirable fluids and particles is removed from the blood by convection across the membrane into the secondary chamber. In a hemofiltration (HF) treatment, the blood flows past the semipermeable membrane as in UF and desirable substances are added to the blood, typically by dispensing a fluid into the blood either via respective infusion lines before and/or after it passes through the filtration unit and before it is returned to the patient. In a hemodialysis (HD) treatment, a secondary fluid containing desirable substances is introduced into the secondary chamber of the filtration unit. Undesirable substances from the blood may cross the semipermeable membrane by diffusion into the secondary fluid and desirable substances from the secondary fluid may cross the membrane into the blood. In a hemodiafiltration (HDF) treatment, blood and secondary fluid exchange matter as in HD+UF, and, in addition, fluid is added to the blood, typically by dispensing it into the blood before its return to the patient as in HF.

To perform one or more of the above described treatments, extracorporeal blood treatment equipment may comprise a plurality of lines for delivering fluid directly to the patient or into the extracorporeal blood circuit.

When setting up the machine, an operator usually imposes the blood pump flow rate, the individual flow rates for each of the infusion lines, the flow rate for the dialysis line and for the effluent line (in reality this latter may alternatively be calculated based on the information of the set weight loss and treatment time or based on the set patient fluid removal rate). The set values for the flow rates on each line are used to control respective pumps: in other words, a plurality of pumps are used where each pump draws fluid from or supplies fluid to a respective fluid container according to the set flow rate value for the respective line. Setting up of the machine is therefore cumbersome as it entails the definition and entry on the part of the operator of a relatively high number of flow rates. Moreover, the independent setting of each one of the flow rates does not provide the operator with intuitive information in terms of medically relevant prescription parameters. Finally, the need for independently setting a plurality of parameters may be source of errors and does not allow to optimize fluid consumption.

SUMMARY

In this situation, it is a general object of the present invention to offer a technical solution capable overcoming one or more of the above drawbacks.

More in detail, it is an object of the present invention to render available a medical apparatus for the extracorporeal treatment of blood and a process for calculating set flow rates in said apparatus capable of reducing as possible the actions required for setting up the apparatus.

Is a further object of aspects of the invention to define an apparatus and a process allowing the operator to set up a blood treatment apparatus using medically meaningful parameters which may result in an easier to use user interface.

It is an auxiliary object of the invention to offer a medical apparatus for the treatment of fluid and a process for calculating set flow rates in said apparatus which may facilitate flow rate setting before and during the treatment and optimize the consumption of fluid with respect to the prescription target and the system constraints.

It is also an object of certain aspects of the present invention to render available a medical apparatus for the treatment of fluid and a process for calculating set flow rates in said apparatus capable of reducing as possible the frequency of container changes and consequent interruptions of treatment deliver.

Another auxiliary object is an apparatus capable of controlling operating parameters in a safe manner.

At least one of the above objects is substantially reached by an apparatus according to one or more of the appended apparatus claims. One or more of the above objects is also substantially reached by a process according to any one of the appended process claims.

Apparatus and processes according to aspects of the invention are here below described.

A first aspect concerns an apparatus for extracorporeal treatment of blood comprising a filtration unit having a primary chamber and a secondary chamber separated by a semi-permeable membrane; a blood withdrawal line connected to an inlet of the primary chamber, and a blood return line connected to an outlet of the primary chamber said blood lines being configured for connection to a patient cardiovascular system; a blood pump configured to control the flow of blood through the blood lines; an effluent fluid line connected to an outlet of the secondary chamber; at least two further fluid lines selected in the group comprising:

a pre-dilution infusion fluid line connected at one end thereof to the blood withdrawal line, a post-dilution infusion fluid line connected at one end thereof to the blood return line, a dialysis fluid line connected at one end thereof to the inlet of the secondary chamber, a pre-blood pump infusion fluid line connected at one end thereof to the blood withdrawal line in a region of this latter which is positioned in use upstream the blood pump, means, such as peristaltic pumps or flow regulating valves or centrifugal pumps, for regulating the flow of fluid through said fluid lines; and a control unit connected to the means for regulating, the control unit being configured to:

allow entry by an operator of the set value for at least a first fluid flow rate selected in the group including:

a fluid flow rate $Q_{rep1}$ through the pre-dilution infusion fluid line, a fluid flow rate $Q_{rep2}$ through the post-infusion fluid line, a fluid flow rate $Q_{pbp}$ through the pre-blood pump infusion fluid line, a fluid flow rate $Q_{dial}$ through the dialysis liquid fluid line, and a fluid removal rate $Q_{pfr}$ from the patient, allow entry of a set value for a prescribed dose $D_{set}$ to be delivered, calculate set values of at least a second and a third of the fluid flow rates of said group of flow rates, based on the said first fluid flow rate set by the operator and on said prescribed dose value $D_{set}$.

In a second aspect according to the second aspect the control unit is further configured to control said means for regulating the flow of fluid based on said set values of the fluid flow rates. In other words the control unit uses the calculated set values of the fluid flow rates for e.g. controlling the rotational pump of the pumps or the position of the regulating valves used on the fluid lines.

In a third aspect according to any one of the preceding aspects a memory is provided storing a plurality of mathematical relations correlating fluid flow rates selected in said group, said control unit being connected to said memory.

In a fourth aspect according to the preceding aspect the control unit is further configured to calculate the set values at least of the second and third fluid flow rates by applying said prescribed dose value $D_{set}$ and the set value of the first fluid flow rate entered by the operator to said mathematical relations.

In a fifth aspect according to any one of the preceding two aspects, wherein said mathematical relations stored in said memory comprise one or more of the following:

a convection-diffusion relation, relating the total fluid flow rate through said infusion fluid lines $Q_{rep1}+Q_{rep2}+Q_{pbp}$ with the fluid flow rate through said dialysis fluid line $Q_{dial}$, a blood pre-dilution relation, relating the flow rate of blood or of plasma $Q_{BLOOD}$, $Q_{PLASMA}$ and the fluid flow rate infused in the blood withdrawal line $Q_{rep1}+Q_{pbp}$ through said pre-dilution infusion fluid line and through said pre-blood pump infusion line, a pre-post relation, relating the fluid flow rates $Q_{rep1}+Q_{pbp}$ through pre-dilution infusion fluid line and pre-blood pump infusion line with the fluid flow rate through the post-dilution infusion line $Q_{rep2}$.

In a sixth aspect according to the preceding aspects all said mathematical relations specified in the fifth aspect are stored in said memory.

In a seventh aspect according to any one of the preceding aspects from the $3^{rd}$ to the sixth, the control unit is further configured to allow the user to select at least two of said relations and to calculate the set values of at least the second and third of said fluid flow rates by applying the set value of the prescribed dose and the set value of the first fluid flow rate entered by the operator to the mathematical relations selected by the user.

In an eighth aspect according to any one of the preceding aspects from the fifth to the seventh, the convection-diffusion relation defines a first ratio $R_1$ dividing the total fluid flow rate $Q_{rep1}+Q_{rep2}+Q_{pbp}$ through said infusion fluid lines by the fluid flow rate $Q_{dial}$ through said dialysis fluid line.

In a ninth aspect according to any one of the preceding aspects from the fifth to the eighth, the blood pre-dilution relation defines a second ratio $R_2$ dividing the flow rate of blood or of plasma $Q_{BLOOD}$, $Q_{PLASMA}$ by the sum of fluid flow rates $Q_{rep1}+Q_{pbp}$ infused in the blood withdrawal line through said pre-dilution infusion fluid line and through said pre-blood pump infusion line.

In a tenth aspect according to any one of the preceding aspects from the fifth to the ninth, the pre-post relation defines a third ratio $R_3$ dividing the sum of the fluid flow rates $Q_{rep1}+Q_{pbp}$ through said pre-blood pump infusion line and pre-dilution infusion line by the fluid flow rate $Q_{rep2}$ through said post-dilution infusion line.

In an eleventh aspect according to any one of the preceding aspects from the fifth to the tenth, the control unit is further configured to: store a preset value or preset range for each one of said first, second and third ratios $R_1$, $R_2$, $R_3$.

In a twelfth aspect according to any one of the preceding aspects from the fifth to the eleventh, the control unit is further configured to allow entry by an operator of a set value or a set range for each one of said first, second and third ratios $R_1$, $R_2$, $R_3$.

In a thirteenth aspect according to any one of the preceding aspects the blood pump is active in correspondence of a segment of the blood withdrawal line and the apparatus comprises the following fluid lines:

a pre-dilution infusion fluid line connected to the blood withdrawal line between the blood pump segment and the filtration unit, a post-dilution infusion fluid line connected to the blood return line, a dialysis fluid line connected to the inlet of the secondary chamber;

wherein the control unit is configured to calculate the set value for the fluid flow rate through each of the above-listed infusion lines which is not set by the operator based on said first fluid flow rate set by the operator and on said prescribed dose value $D_{set}$.

In a fourteenth aspect according to any one of the preceding aspects the blood pump is active in correspondence of a segment of the blood withdrawal line and the apparatus comprises the following fluid lines:

a pre-dilution infusion fluid line connected to the blood withdrawal line between the blood pump segment and the filtration unit, a pre-blood pump infusion line connected to the blood withdrawal line in a region of this latter which is positioned in use upstream the blood pump segment, a post-dilution infusion fluid line connected to the blood return line, a dialysis fluid line connected to the inlet of the secondary chamber;

wherein the control unit is configured to calculate the set value for the fluid flow rate through each of the above-listed infusion lines which is not set by the operator based on said first fluid flow rate set by the operator and on said prescribed dose value $D_{set}$.

In a fifteenth aspect according to any one of the preceding aspects said prescribed dose value $D_{set}$ comprises a prescribed value for a flow rate or a combination of flow rates.

In a sixteenth aspect according to any one of the preceding aspects, said prescribed dose value $D_{set}$ comprises a prescribed value for one selected in the group including:

an effluent dose flow rate $D_{eff\_set}$, which is the prescribed mean value of the flow rate through the effluent line, a convective dose flow rate $D_{conv\_set}$, which is the prescribed mean value of the sum of the flow rates through all infusion fluid lines $Q_{rep1}$, $Q_{rep2}$, $Q_{pbp}$ and the patient fluid removal rate $Q_{pfr}$, optionally wherein the prescribed convective dose flow rate value is corrected for predilution, a diffusive dose flow rate $D_{dial\_set}$: which is the prescribed mean value of the flow rate through the dialysis fluid line $Q_{dial}$, an urea dose $D_{urea\_set}$, which is a prescribed mean value for an estimated urea clearance, a clearance dose $K_{solute\_set}$, which is a prescribed mean value for an estimated clearance for a given solute.

In a seventeenth aspect according to the preceding aspect, the control unit is configured to correct the selected one of the above defined doses to take into account a predilution effect, when a fluid replacement or infusion line is present and delivers fluid upstream the treatment unit, by multiplying the dose value times a dilution factor $F_{dilution}$, which is <then 1, as per the following formula:

$$\text{Dose}_{corr\_xxx} = F_{dilution} \times \text{Dose}_{-xxx} \text{ (with } xxx = \text{eff,conv, dial).}$$

In an eighteenth aspect according to any one of the preceding aspects from the third to the seventeenth, said first fluid flow rate is the fluid removal rate $Q_{pfr}$ from the patient and wherein the control unit is configured to receive the set value of the patient fluid removal rate $Q_{pfr}$ and to calculate the fluid flow rate $Q_{dial}$ through the dialysis liquid fluid line and the fluid flow rate $Q_{rep1}$, $Q_{pbp}$, $Q_{rep2}$ through the infusion fluid line or lines using at least two of said mathematical relations.

In a nineteenth aspect according to any one of the preceding aspects the control unit is further configured to allow entry by an operator of the set value for a blood flow $Q_{BLOOD}$ through the blood withdrawal or blood return line.

In a twentieth aspect according to any one of the preceding aspects the control unit is configured to calculate the set value for the blood flow based on a sensed value of a patient parameter selected in the group comprising:

blood pressure measured in a tract of the blood withdrawal line portion extending, in use, upstream the blood pump, a measured blood recirculation fraction re-circulating from the blood return line into the blood withdrawal line, a measured value of hemo-concentration measured in correspondence of one of the blood lines, a measured value of transmembrane pressure across the filter semipermeable membrane.

In a twenty-first aspect according to any one of the preceding two aspects the control unit is configured to control the blood pump using either the entered or the calculated set value for the blood flow $Q_{BLOOD}$.

In a twenty-second aspect according to any one of the preceding aspects the control unit is further configured to calculate the set value for the fluid flow rate $Q_{pbp}$ through said pre-blood pump infusion line as a function of:

the set or calculated value of flow rate of blood or of plasma $Q_{BLOOD}$; $Q_{PLASMA}$, a concentration $C_{citrate}$ of an anticoagulant, such as a citrate based solution, present in a container connected at an end of said pre-blood pump infusion line, a prescribed dose for said anticoagulant $D_{set-citrate}$, such as a citrate based solution, to be delivered through said pre-blood pump infusion line.

In a twenty-third aspect according to any one of the preceding aspects from the third to the twenty-second, the apparatus further comprises a graphic user interface connected to said control unit, said control unit being configured to:

display on the graphic user interface an indicium prompting a user to select the value for said first flow rate, display on the graphic user interface an indicium allowing selection of the mathematical relations the user intends to select, detecting selection of a mathematical relation and display an indicium allowing selection of a set value for one or more of said first, second and third ratios.

In a twenty-fourth aspect according to any one of the preceding aspects the means for regulating the flow of fluid through said fluid lines comprises a pre-dilution pump for regulating the flow through said pre-dilution fluid line and a post-dilution pump for regulating the flow through said post-dilution fluid line.

In a twenty-fifth aspect according to any one of the preceding aspects a dialysis fluid line is connected to the inlet of the secondary chamber, and the means for regulating the flow of fluid through said fluid lines comprises at least a dialysis fluid pump for regulating the flow through said dialysis fluid line.

In a twenty-sixth aspect according to any one of the preceding aspects said one or more infusion fluid lines comprise:

a pre-blood pump infusion line connected to the blood withdrawal line in a region of this latter which is positioned in use upstream the blood pump, the means for regulating the flow of fluid through said fluid lines comprises at least a pre-blood infusion pump for regulating the flow through said pre-blood pump infusion line.

In a twenty-seventh aspect according to any one of the preceding aspects the apparatus further comprises a memory storing a one or a plurality of optimization criteria, said control unit being connected to said memory and being further configured to calculate the set values at least one of the second and third fluid flow rates by applying the optimization criteria.

In a twenty-eighth aspect according to any one of the preceding aspects, the apparatus includes a waste container connected to an end of the effluent fluid line.

In a twenty-ninth aspect according to any one of the preceding aspects, the apparatus includes a first container of fresh fluid connected to an end of the pre-dilution infusion fluid line.

In a thirtieth aspect according to any one of the preceding aspects, the apparatus includes a second container of fresh fluid connected to an end of the post-infusion fluid line.

In a thirty-first aspect according to any one of the preceding aspects, the apparatus includes a third container of fresh fluid connected to an end of the dialysis liquid fluid line.

In a thirty-second aspect according to any one of the preceding aspects, the apparatus includes a fourth container of fresh fluid connected to an end of the pre-blood pump infusion fluid line.

In a thirty-third aspect according to any one of the preceding aspects from the twenty-seventh to the thirty-second, the optimization criteria comprises a first optimization criterion imposing that an emptying time of at least two among the containers of fresh fluid and, optionally, a filling time of the waste container are multiple of a same reference time.

In a thirty-fourth aspect according to any one of the preceding aspects from the twenty-seventh to the thirty-second, the optimization criteria comprises a first optimization criterion imposing that an emptying time of at least one among the containers of fresh fluid and/or a filling time of the waste container is substantially same as or multiple of the emptying time of one or more of the other containers of fresh fluid.

In a thirty-fifth aspect according to any one of the preceding aspects from the twenty-seventh to the thirty-fourth the optimization criteria comprises a second optimization criterion imposing that fluid consumption through said fluid lines is minimized.

In a thirty-sixth aspect according to any one of the preceding aspects from the twenty-seventh to the thirty-fifth the optimization criteria comprises a third optimization criterion imposing that a life time of said filtration unit is maximized.

In a thirty-seventh aspect according to any one of the preceding aspects from the twenty-seventh to the thirty-sixth the optimization criteria comprises a fourth optimization criterion imposes that urea clearance or dialysance of a given solute is maximized.

In a thirty-eighth aspect according to any one of the preceding aspects from the twenty-seventh to the thirty-seventh the control unit is configured to allow the user selecting one or more of said criteria and calculate said at least second and third flow rate using said selected criteria.

In a thirty-ninth aspect according to any one of the preceding aspects from the twenty-seventh to the thirty-seventh allow the user selecting one or more of said criteria and one or more of said mathematical relations and to calculate said at least second and third flow rate using said selected criteria and said selected mathematical relations.

In a fortieth aspect according to the preceding aspect the control unit is configured to determine if said selected criteria and said selected mathematical relations are compatible or conflicting and then:

in case the selected criteria and the selected mathematical relations are compatible, calculate the at least second and third flow rate based on the selected mathematical relations and optimization criteria, in case one or more of the selected criteria is conflicting with one or more selected mathematical relations, execute one or more of the following sub-steps:

inform the user, allow the user to assign a priority to each of the selected criteria or mathematical relations, assign a priority ranking to the selected criteria and/or mathematical relations, said priority ranking being either predetermined or user adjustable, and then ignore criteria or mathematical relations as soon as flow rates have been calculated from the prioritized criteria/mathematical relations, define a compromise between conflicting criteria and mathematical relations using preset rules.

In a variant of the invention it should be noted that the control unit may be configured combine the use of the flow rate set-up procedure with the use of one or more optimization criteria. For example the control unit may be configured to:

execute said flow-rate setup (see previous aspects) procedure to calculate set values for a plurality of flow rates of said group and, at least for a first time interval, control the means for regulating the flow of fluid (17, 18, 21, 24, 27) based on the set values calculated executing the flow-rate setup procedure; and then allow selection of one optimization criteria, for instance the first optimization criterion, to calculate the set values for a plurality of flow rates using the selected optimization criterion, for then (at least for a second time interval subsequent to the first time interval) controlling said means for regulating the flow of fluid (17, 18, 21, 24, 27) based on the set values calculated based on the selected optimization criterion.

A forty-first aspect relates to an apparatus for extracorporeal treatment of fluid comprising:

a filtration unit having a primary chamber and a secondary chamber separated by a semi-permeable membrane;

a blood withdrawal line connected to an inlet of the primary chamber, and a blood return line connected to an outlet of the primary chamber said blood lines being configured for connection to a patient cardiovascular system;

a blood pump configured to control the flow of blood through the blood lines;

an effluent fluid line connected, at one end thereof, to an outlet of the secondary chamber and, at its other end, optionally connected to a waste container;

at least two further fluid lines selected in the group of fluid lines comprising:

a pre-dilution infusion fluid line connected at one end thereof to the blood withdrawal line and at its other end to a first container of fresh fluid, a post-dilution infusion fluid line connected at one end thereof to the blood return line and at its other end to a second container of fresh fluid, a dialysis fluid line connected at one end thereof to the inlet of the secondary chamber and at its other end to a third container of fresh fluid, a pre-blood pump infusion fluid line connected at one end thereof to a fourth container of fresh fluid and at its other end to the blood withdrawal line in a region of this latter which is positioned in use upstream the blood pump, one or more syringe lines (50) connected at one end thereof either to the blood withdrawal line (6) or to the blood return line (7) or directly to the patient, and at its other end to a syringe container (S), means for regulating the flow of fluid (17, 18, 21, 22, 27, P) through one or more said fluid lines (13, 15, 21, 25, 19); and a control unit (10) connected to the means for regulating, the control unit being configured to:

calculate set values ($Q_{iset}$) of two or more of the fluid flow rates selected in the group of fluid flow rates including:

a fluid flow rate ($Q_{rep1}$) through the pre-dilution infusion fluid line (15), a fluid flow rate ($Q_{rep2}$) through the post-infusion fluid line (25), a fluid flow rate ($Q_{pbp}$) through the pre-blood pump infusion fluid line (21), a fluid flow rate ($Q_{dial}$) through the dialysis liquid fluid line (27), a fluid flow rate ($Q_{syr}$) through the syringe fluid line (50), a fluid flow rate ($Q_{eff}$) through the effluent fluid line (13), by imposing that emptying times of at least two among the containers of fresh fluid (16, 20, 21, 26, S) and, optionally, the filling time of the waste container are multiple of a same reference time ($T_r$).

By defining the reference time $T_r$ and a multiplication factor, it is possible to define in relation to each fresh fluid line e.g. the following:

an emptying time of the respective container which is the same of the emptying time of a container relating to another line, an emptying time of the respective container which is the multiple of the emptying time of a container relating to another line, an emptying time of the respective container which is a fraction (A/B where both A and B are integers) of the emptying time of a container relating to another line.

Optionally the above relations may be applied, mutatis mutandis, to the filling time of the waste container.

In a forty-second aspect according to the forty-first aspect the control unit is configured to:

calculate the set values of (N–1) of said fluid flow rates ($Q_{iset}$) by imposing that an emptying time of at least one among the containers of fresh fluid (16, 20, 21, 26) is substantially same as, or multiple of the emptying time of one or more of the other containers of fresh fluid; note that alternatively said empting time may be imposed to be substantially same as, or multiple of one selected among: the emptying time of one or more of the other containers of fresh fluid, and the filling time of the waste container; also note that the reference time ($T_r$) may be the shortest among said empting times; and calculate the remaining of said fluid flow rates ($Q_{iset}$) by applying a fluid balance equation imposing that the sum of the fluid flow rates through fluid lines coming from fresh fluid containers ($Q_{rep1}$, $Q_{rep2}$, $Q_{dial}$, $Q_{pbp}$) and of a patient fluid removal rate ($Q_{pfr}$) is equal to the effluent fluid line flow rate ($Q_{eff}$):

$$\Sigma(Q_{repi}+Q_{dial}+Q_{pbp}+Q_{pfr})=Q_{eff}$$

In a forty-third aspect according to the forty-first aspect the control unit is configured to:

calculate the set values of (N–1) of said fluid flow rates ($Q_{iset}$) by imposing that an emptying time of at least one among the containers of fresh fluid (16, 20, 21, 26) is substantially same as, or multiple of the filling time of the waste container, and calculate the remaining of said fluid flow rates ($Q_{iset}$) by applying a fluid balance equation imposing that the sum of the fluid flow rates through fluid lines coming from fresh fluid containers ($Q_{rep1}$, $Q_{rep2}$, $Q_{dial}$, $Q_{pbp}$) and of a patient fluid removal rate ($Q_{pfr}$) is equal to the effluent fluid line flow rate ($Q_{eff}$):

$$\Sigma(Q_{repi}+Q_{dial}+Q_{pbp}+Q_{pfr})=Q_{eff}$$

In a forty-fourth aspect, according to any one of the preceding three aspects, the control unit is configured to use at least two reference times $T_{r1}$ and $T_{r2}$. This solution may be adopted when the apparatus includes at least four of the fluid lines selected in said group of fluid lines specified in aspect 41. The control unit is configured to calculate set values ($Q_{iset}$) of two or more of:

a fluid flow rate ($Q_{rep1}$) through the pre-dilution infusion fluid line (15), a fluid flow rate ($Q_{rep2}$) through the post-infusion fluid line (25), a fluid flow rate ($Q_{pbp}$) through the pre-blood pump infusion fluid line (21), a fluid flow rate ($Q_{dial}$) through the dialysis liquid fluid line (27), a fluid flow rate ($Q_{syr}$) through the syringe fluid line (50), a fluid flow rate ($Q_{eff}$) through the effluent fluid line (13), by imposing that the emptying times of at least two among the containers of fresh fluid (16, 20, 21, 26, S) and, optionally, the filling time of the waste container are multiple of a first reference time ($T_{r1}$) and also imposing that that emptying times of at least two other among the containers of fresh fluid (16, 20, 21, 26, S) and, optionally, the filling time of the waste container are multiple of a second reference time ($T_{r2}$).

In other words, in accordance with this aspect it is possible to synchronize the emptying of two or more containers (e.g. container 16 and 20) of fresh fluid with reference to a first reference time such that for instance the emptying time of said two containers is multiple of the first reference time, while the emptying two or more other containers (e.g. containers 21 and 26, or 21, 26 and S) may be synchronized with reference to a second reference time such that for instance the emptying time of said two other containers is multiple of the second reference time. This may still allow a good degree of overall synchronization and time saving. Of course it is also possible to synchronize the filling of the waste container with reference to either one of the two reference times.

In principle, if the apparatus would include a relevant number of lines bringing and or withdrawing fluid from the blood circuit and leading to respective fresh fluid containers or waste containers, it may be possible to synchronize the emptying/filling of the containers in 3 or more groups where each group of containers is synchronized relative to a respective reference time.

In a forty-fifth aspect according to any one of the aspects from the forty-first to the forty-fourth, the control unit is further configured to control said means for regulating based on said calculated set values, either automatically or after receipt of a confirmation signal.

In a forty-sixth aspect according to any one of the aspects from the forty-first to the forty-fifth the apparatus comprises at least the following fluid lines:

a pre-dilution infusion fluid line connected to the blood withdrawal line, a post-dilution infusion fluid line connected to the blood return line, a dialysis fluid line connected to the inlet of the secondary chamber.

In a forty-seventh aspect according to any one of the aspects from the forty-first to the forty-sixth the control unit is configured to calculate the set value for the fluid flow rate through each of the infusion fluid lines and dialysis fluid line by imposing that the emptying time of each given of said first, second and third containers is multiple of the same reference time $T_r$.

In a forty-eighth aspect according to any one of the aspects from the forty-first to the forty-sixth the control unit is configured to calculate the set value for the fluid flow rate through each of the infusion fluid lines and dialysis fluid line by imposing that the emptying time of each given of said first, second and third containers is same as or multiple of the emptying time of one or more other of said first, second and third containers.

In a forty-ninth aspect according to any one of the preceding aspects the blood pump is active in correspondence of a segment of the blood withdrawal line, the pre-dilution infusion fluid line is connected to the blood withdrawal line between the blood pump segment and the filtration unit, and a pre-blood pump infusion fluid line is connected to the blood withdrawal line in a region of this latter which is positioned between the blood pump segment and an end of the blood withdrawal line opposite the end connected to the filtration unit.

In a fiftieth aspect according to any one of the preceding aspects the control unit is configured to calculate the set value for the fluid flow rate through each of the infusion fluid lines and dialysis fluid line by imposing that the emptying time of each given of said first, second, third, and fourth containers is multiple of the same reference time $T_r$.

In a fifty-first aspect according to the preceding aspect the control unit is configured to calculate the set value for the fluid flow rate through each of the infusion fluid lines and dialysis fluid line by imposing that the emptying time of each given of said first, second, third, and fourth containers is same as or multiple of the emptying time of one or more other of said first, second, third, and fourth containers.

In a fifty-second aspect according to the preceding aspect the waste line is connected to the waste container and the control unit is configured to calculate the set value for the fluid flow rate through each of the fluid lines by imposing that the emptying time of each given of said containers of fresh fluid and the filling time of the waste container are multiple of the same reference time $T_r$ and are optionally same as or multiple of the emptying time of one or more other containers of fresh fluid or filling time of the waste container.

In a fifty-third aspect according to any one of the preceding aspects the control unit is configured to store in a memory connected to the control unit the volume or weight of fluid which may be contained in each container of fresh fluid and optionally in said waste container.

In a fifty-fourth aspect according to the preceding aspect, said volume or weight of fluid is detected by a sensor associated to each respective container and connected to the control unit.

In a fifty-fifth aspect according to the fifty-third aspect, said volume or weight of fluid is entered by an operator for each respective container through a user interface connected to the control unit; or said volume or weight of fluid is determined by the control unit associating an identification code on each respective container to a respective volume.

In a fifty-sixth aspect according to the fifty-third aspect, said volume or weight of fluid is pre-stored in said memory.

In a fifty-seventh aspect according to any one of the preceding aspects the control unit is further configured to receive, for instance by allowing a corresponding selection by an operator, at least one set value for a treatment time T.

In a fifty-eighth aspect according to any one of the preceding aspects the control unit is further configured to receive, for instance by allowing a corresponding selection by an operator, at least one set value for a treatment dose $D_{set}$ to be delivered to the patient during the treatment.

In a fifty-ninth aspect according to the preceding aspect the set value for the treatment dose comprises a prescribed value for one selected in the group including:

an effluent dose flow rate $D_{eff\_set}$, which is the prescribed mean value of the flow rate through the effluent line, a convective dose flow rate $D_{conv\_set}$, which is the prescribed mean value of the sum of the flow rates through any infusion fluid line $Q_{rep}$, $Q_{pbp}$ and the patient fluid removal rate $Q_{pfr}$, a diffusive dose flow rate $D_{dial\_set}$, which is the prescribed mean value of the flow rate through the dialysis fluid line $Q_{dial}$, an urea dose $D_{urea\_set}$, which is a prescribed mean value for an estimated urea clearance, a clearance dose $K_{solute\_set}$, which is a prescribed mean value for an estimated clearance for a given solute.

In a sixtieth aspect according to any one of the preceding aspects the control unit is further configured to receive, for instance by allowing a corresponding selection by an operator, at least one set value for one or more of:

a fluid flow rate $Q_{rep1}$ through the pre-dilution infusion fluid line;

a fluid flow rate $Q_{rep2}$ through the post-infusion fluid line;

a fluid flow rate $Q_{pbp}$ through the pre-blood pump infusion fluid line;

a fluid flow rate $Q_{dial}$ through the dialysis liquid fluid line;

a fluid flow rate $Q_{eff}$ through the effluent fluid line.

In a sixty-first aspect according to any one of the preceding aspects the apparatus comprises one or more scales weighing one or more of said containers.

In a sixty-second aspect according to any one of the preceding aspects the apparatus comprises a corresponding scale for each respective of said containers, said one or more scales being connected to the control unit and sending to the control unit corresponding weight signals.

In a sixty-third aspect according to any one of the preceding aspects the control unit is configured to:

receive an initial weight or volume $W_i$, $V_i$ of one or more of said containers, calculate the set value of the fluid flow rate $Q_{iset}$ in one or more of said fluid lines dividing a weight or volume $W_i$, $V_i$ of the respective container by the value of the reference time $T_r$ using formula: $Q_{iset}=W_i/T_r$ or $Q_{iset}=V_i/T_r$.

In a sixty-fourth aspect according to any one of the preceding aspects the control unit is configured to:

receive an initial weight or volume $W_i$, $V_i$ of one or more of said containers, calculate the set value of the fluid flow rate $Q_{iset}$ in one or more of said fluid lines or dividing a weight or volume $W_i$, $V_i$ of the respective container by the value of a reference time $T_r$ multiplied by a respective weighing coefficient $c_i$ for each respective container using formula:

$$Q_{iset}=W_i/(T_r \cdot c_i) \text{ or } Q_{iset}=W_i/(T_r \cdot c_i)$$

In a sixty-fifth aspect according to any one of the preceding aspects the control unit is configured to:

receive an initial weight or volume $W_i$, $V_i$ of one or more of said containers, receive proposed values $Q_i$ of the flow rates for said fluid lines;

calculate the set value of the fluid flow rate $Q_{iset}$ in one or more of said fluid lines dividing a weight or volume $W_i$, $V_i$ of the respective container by the value of the reference time $T_r$ multiplied by a respective weighing coefficient $c_i$ for each respective container using formula:

$$Q_{iset}=W_i/(T_r \cdot c_i), \text{ or } Q_{iset}=V_i/(T_r \cdot c_i),$$

where the weighing coefficient $c_i$ for each respective container is calculated as a function of an intermediary factor $b_i$ obtained by dividing either the dose or the sum of said proposed values $Q_i$ of the flow rates by the respective proposed value $Q_i$, optionally wherein the weighing coefficient $c_i$ for each respective container is calculated using formula:

$$C_i=\text{Round}[b_i/\text{min}(b_1 \ldots b_n)], \text{ where:}$$

"$\text{min}(b_1 \ldots b_n)$" is a function selecting the minimum among the $b_i$ factors, and "Round" calculates the natural number nearest to the result of quotient $b_i/\text{min}(b_1 \ldots b_n)$.

In a sixty-sixth aspect according to any one of the preceding aspects the control unit is configured to:

receive an initial weight or volume $W_i$, $V_i$ of one or more of said containers, receive proposed values $Q_i$ of the flow rates for said fluid lines;

receive the value of an adjustment parameter A defined as maximum relative change allowed on container change periods;

calculate the set values of said fluid flow rates $Q_{iset}$ based on the proposed values $Q_i$, the initial weight or volume $W_i$, $V_i$ of each container and the value of the adjustment parameter A.

A sixty-seventh aspect relates to an apparatus for extracorporeal treatment of fluid comprising:

a filtration unit having a primary chamber and a secondary chamber separated by a semi-permeable membrane;

a blood withdrawal line connected to an inlet of the primary chamber, and a blood return line connected to an outlet of the primary chamber said blood lines being configured for connection to a patient cardiovascular system;

a blood pump configured to control the flow of blood through the blood lines;

an effluent fluid line connected, at one end thereof, to an outlet of the secondary chamber and, at its other end, optionally connected to a waste container;

at least two further fluid lines selected in the group comprising:

a pre-dilution infusion fluid line connected at one end thereof to the blood withdrawal line and at its other end to a first container of fresh fluid, a post-dilution infusion fluid line connected at one end thereof to the blood return line and at its other end to a second container of fresh fluid, a dialysis fluid line connected at one end thereof to the inlet of the secondary chamber and at its other end to a third container of fresh fluid, a pre-blood pump infusion fluid line connected at one end thereof to a fourth container of fresh fluid and at its other end to the blood withdrawal line in a region of this latter which is positioned in use upstream the blood pump, one or more syringe lines (50) connected at one end thereof either to the blood withdrawal line (6) or to the blood return line (7) or directly to the patient, and at its other end to a syringe container (S), means for regulating the flow of fluid through one or more said fluid lines; and a control unit connected to the means for regulating, the control unit being configured to calculate set values $Q_{iset}$ of two or more of the fluid flow rates selected in the group including:

a fluid flow rate $Q_{rep1}$ through the pre-dilution infusion fluid line, a fluid flow rate $Q_{rep2}$ through the post-infusion fluid line, a fluid flow rate $Q_{pbp}$ through the pre-blood pump infusion fluid line, a fluid flow rate $Q_{dial}$ through the dialysis liquid fluid line, a fluid flow rate ($Q_{syr}$) through the syringe fluid line, a fluid flow rate $Q_{eff}$ through the effluent fluid line, by executing the following steps:

receiving an initial weight or volume $W_i$, $V_i$ of one or more of said containers, receiving proposed values $Q_i$ of the flow rates for said fluid lines;

receiving the value of an adjustment parameter A defined as maximum relative change allowed on container change periods;

calculating the set values of said fluid flow rates $Q_{iset}$ based on the proposed values $Q_i$, the initial weight or volume $W_i$, $V_i$ of each container and the value of the adjustment parameter A.

In a sixty-eighth aspect according to any one of the preceding aspects the control unit is configured to:

receive an initial weight or volume $W_i$, $V_i$ of one or more of said containers, receive proposed values $Q_i$ of the flow rates for said fluid lines, which may be either entered by the user or come from a previous calculation step, e.g. using the mathematical relations mentioned in some of the above aspects, for each pair of lines and respective containers, generate ratios of interest $R0_k$, which are reference ratios between change periods of pairs of containers and are defined for each pair of lines and respective containers, K being an integer from 1 to M, with the value of M pre-stored in the control unit memory or receivable from a user input;

calculate the containers change periods $T_i=V_i/Q_i$ or $T_i=W_i/Q_i$ and rank each circuit according to the calculated container change period, where i=1 to N with $T_i$ increasing with i and N is the number of lines to which the calculation (that is the synchronization sequence) applies;

compute all period ratios $R_{ij}=T_i/T_j$, with i>j;

compare each period ratio $R_{ij}$ to the ratios of interest $R0_k$;

verify if there is a k value verifying that $R_{ij}/R0_k$ stays within a tolerance limit (selectable by the user or preset in a memory of the computer unit), compute the number of daily saved container changes and selecting the ratios $R_{ij}$ providing the largest number of saved container changes and respecting the above tolerance limit;

apply the ratios of interest corresponding to the selected ratios $R_{ij}$ to compute the optimized flow rates $Q_{iset}$.

In a sixty-ninth aspect according to any one of the preceding aspects the control unit is configured to:

receive an initial weight or volume $W_i$, $V_i$ of one or more of said containers, receive proposed values $Q_i$ of the flow rates for said fluid lines, which may be either entered by the user or come from a previous calculation step, e.g. using the mathematical relations mentioned in some of the above aspects, for each pair of lines and respective containers, generate ratios of interest $R0_k$, which are reference ratios between change periods of pairs of containers and are defined for each pair of lines and respective containers, K being an integer from 1 to M, with the value of M pre-stored in the control unit memory or receivable from a user input;

calculate the containers change periods $T_i = V_i/Q_i$ or $T_i = W_i/Q_i$ and rank each circuit according to the calculated container change period, where i=1 to N with $T_i$ increasing with i and N is the number of lines to which the calculation (that is the synchronization sequence) applies;

compute all period ratios $R_{ij} = T_i/T_j$, with i>j;

compare each period ratio $R_{ij}$ to the ratios of interest $R0_k$;

for each ratio $R_{ij}$ where a k value exists verifying the tolerance relation: $(1-A) \cdot R0_k < R_{ij} < (1+A) \cdot R0_k$, compute the number of daily saved container changes;

select the ratios $R_{ij}$ providing the largest number of saved container changes;

apply the ratios of interest corresponding to the selected ratios to compute the optimized flow rates $Q_{iset}$.

In a seventieth aspect according to any one of the preceding aspects from the $41^{st}$ to the $69^{th}$ said control unit is configured to:

allow entry of the treatment time T, calculate the reference time $T_r$ either as the treatment time T or as a sub-multiple of the treatment time T.

In a seventy-first aspect according to any one of the preceding aspects from the forty-first to the seventieth the control unit is configured to receive one set value set by an operator for one fluid flow rate selected in the group comprising:

a fluid flow rate $Q_{rep1}$ through the pre-dilution infusion fluid line, a fluid flow rate $Q_{rep2}$ through the post-infusion fluid line, a fluid flow rate $Q_{pbp}$ through the pre-blood pump infusion fluid line, a fluid flow rate $Q_{dial}$ through the dialysis liquid fluid line;

identifying the container associated to the fluid line for which the fluid flow rate has been set by the operator; and calculating the reference time $T_r$, dividing the initial weight or volume $W_i$, $V_i$ of the identified container by the set value of the fluid flow rate set by the operator.

In a seventy-second aspect according to any one of the preceding aspects from the forty-first to the seventy-first the control unit is configured to compute the reference time $T_r$ by:

dividing the sum of the initial weights or volumes $W_i$, $V_i$ of a plurality of said containers by the prescribed dose flow rate value which is set to be delivered in total through the lines $D_{conv\_set}$ leading to the same plurality of containers, or dividing the sum of the initial weights or volumes $W_i$, $V_i$ of all said containers by the total prescribed dose flow rate $D_{eff\_set}$, or dividing the weighed sum of the initial weights or volumes $W_i$ of a plurality of said containers by the prescribed dose flow rate value which is set to be delivered in total through the lines $D_{conv\_set}$ leading to the same plurality of containers, using formula:

$$T_r = \Sigma W_i \cdot c_i/\text{Dose}$$

where $c_i$ is an weighing coefficient to be multiplied by the initial weight or volume of each container; or dividing the weighed sum of the initial weights or volumes $W_i$, $V_i$ of all said containers by the total prescribed dose flow rate $D_{eff\_set}$, using formula:

$$T_r = \Sigma W_i \cdot c_i/\text{Dose}$$

where $c_i$ is the weighing coefficient to be multiplied by the initial weight or volume of each container.

In a seventy-third aspect according to any one of the preceding aspects from the forty-first to the seventy-second wherein the apparatus comprises a separate scale detecting the weight of each respective container.

In a seventy-fourth aspect according to the preceding aspect, the control unit is configured to receive a weight $W_i$ of one or more of said containers as measured by a corresponding scale associated to each container, wherein the weight of each respective container $W_i$ used for the calculation of the set values of the fluid flow rates is determined either at the beginning of the treatment or at a prefixed checkpoint during treatment or responsive to a user input.

In a seventy-fifth aspect according to one of the preceding two aspects the control unit is configured to compare the detected weight of each container of fresh fluid to a respective threshold and to determine that a fresh fluid container is empty if the detected weight is below the respective threshold.

In a seventy-sixth aspect according to one of the preceding three aspects the control unit is configured to compare the detected weight of the waste fluid container a respective threshold and to determine that the waste container is full if the detected weight is above the threshold. The threshold may be fixed or the control unit may be configured to calculate as threshold a set value ($V_{eff\text{-}change}$) of the waste container reference volume or weight, at which the control unit considers that the waste container is full, by imposing that the filling time of the waste container is substantially same as, proportional to, or multiple of the emptying time of one or more of the other containers of fresh fluid.

In a seventy-seventh aspect according to one of the preceding two aspects the control unit is configured to generate an empty container signal when the weight of one or more containers of fresh fluid is below the respective threshold and to generate a full container signal when the weight of said waste container is above the respective threshold.

In a seventy-eighth aspect according to any one of the preceding aspects the means for regulating the flow of fluid through said fluid lines comprises a pre-dilution pump for regulating the flow through said pre-dilution fluid line and a post-dilution pump for regulating the flow through said post-dilution fluid line, a dialysis fluid line is connected to the inlet of the secondary chamber, and the means for regulating the flow of fluid through said fluid lines comprises at least a dialysis fluid pump for regulating the flow through said dialysis fluid line, said one or more infusion fluid lines comprise a pre-blood pump infusion fluid line connected to the blood withdrawal line in a region of this latter which is positioned in use upstream the blood pump, and the means for regulating the flow of fluid through said fluid lines comprises at least a pre-blood infusion pump for regulating the flow through said pre-blood pump infusion line.

In a seventy-ninth aspect according to any one of the preceding aspects the control unit is further configured to:

allow entry by an operator of the set value for a blood flow $Q_{BLOOD}$ through the blood withdrawal or blood return line, or calculate the set value for the blood flow based on a sensed value of a patient parameter selected in the group comprising:

blood pressure measured in a tract of the blood withdrawal line portion extending, in use, upstream the blood pump, a measured blood recirculation fraction re-circulating from the blood return line into the blood withdrawal line, a measured value of hemo-concentration measured in correspondence of one of the blood lines, a measured value of transmembrane pressure across the filter semipermeable membrane, control the blood pump using either the entered or the calculated set value for the blood flow $Q_{BLOOD}$.

In an eightieth aspect according to any one of the preceding aspects said control unit is configured to allow entry of:

a) the fluid removal rate $Q_{pfr}$ from the patient, or of b) the treatment time T and of the weight loss WL to be imposed over said treatment time T. In this second case the fluid removal rate may be calculated as ratio between WL and T.

In an eighty-first aspect according to any one of the preceding aspects the control unit is further configured to calculate the set values ($Q_{iset}$) of the fluid flow rates through said fluid lines by imposing that:

the emptying times of the containers of fresh fluid (16, 20, 21, 26) are multiple of a same reference time ($T_r$), and the sum of the fluid flow rates ($Q_{rep1}$, $Q_{rep2}$, $Q_{pbp}$) through the infusion fluid lines present in the apparatus (15, 25, 21) plus the fluid flow rate ($Q_{dial}$) through the dialysis line (19), if present, plus the fluid removal rate ($Q_{pfr}$) from the patient equals ($Q_{eff}$) the fluid flow rate through the effluent fluid line (13).

In an eighty-second aspect according to any one of the preceding aspects all containers of fresh fluid comprise a fluid having a same composition.

Alternatively, the fourth container of fresh fluid comprises a fluid having a composition different from that of the other containers of fresh fluid, for example said fourth container contains an anticoagulant (heparin or a regional anticoagulant such as a citrate solution): in this case the control unit is configured to calculate the set value of fluid flow rate through the pre-blood pump infusion line based on a pre-defined algorithm: e.g. the flow rate through the pre-blood pump infusion line may be set to be proportional to the set or calculated value of the blood pump flow rate. In a further alternative if the apparatus comprises the fourth container which includes a regional anticoagulant, for example a citrate based solution, then the second container leading to said post-dilution infusion fluid line includes an ionic balance solution, for example calcium ion based solution: in this case the control unit is configured to calculate the fluid flow rate through said pre-blood pump infusion fluid line and through said post-dilution infusion fluid line based on pre-defined algorithm(s).

In an eighty-third aspect according to any one of the preceding aspects the apparatus comprises one or two syringe lines leading to respective syringe containers (S)

including an anticoagulant solution or a ionic balance solution, the control unit being configured to calculate the fluid flow rate through said syringe line or lines based on pre-defined algorithm(s).

In an eighty-fourth aspect according to any one of the preceding aspects the control unit is configured to check if the calculated set value for the fluid flow rate through the post-dilution infusion line is higher than a prefixed fraction of the blood flow rate.

In an eighty-fifth aspect according to the preceding aspect wherein if the calculated set value for the fluid flow rate through the post-dilution infusion line is higher than a prefixed fraction of the blood flow rate, the control unit is configured to activate a correction procedure comprising:

correcting the delivery of fluid through one or more of the other lines, or temporary connecting the post-dilution fluid line to the blood withdrawal line.

In an eighty-sixth aspect according to any one of the preceding aspects the control unit is configured to:

associate to each container a reference volume or a reference weight which, when reached by the respective container, triggers a container change signal, and compare a measured volume or weight of each container to the respective reference volume or reference weight to trigger a container change signal container when the container reaches the respective reference volume or a reference weight;

further wherein the control unit is configured to impose on one or more containers of fresh fluid a reference volume or reference weight which is different from zero and/or on the waste container a reference volume or weight which is less than the maximum volume ore weight of the waste container. For instance the control unit is configured to calculate a set value ($V_{eff\text{-}change}$) of the waste container reference volume or weight, at which the control unit considers that the waste container is full, by imposing that the filling time of the waste container is substantially same as, proportional to, or multiple of the emptying time of one or more of the other containers of fresh fluid.

An eighty-seventh aspect concerns a process of setting up a medical apparatus for the delivery and/or collection of fluids, the apparatus comprising:

a plurality of fluid lines connected at one end thereof a respective container, a pump or a valve regulator configured to regulate the flow of fluid through said fluid lines;

the process comprising the following steps:

calculating set values of two or more of the fluid flow rates through said lines by imposing that an emptying time and/or a filling time of at least one among the containers is substantially same as, proportional to or multiple of, the emptying time of one or more of the other containers, storing said calculated set values in identified retrievable memory locations of said apparatus for subsequent use to control said pump or valve regulator.

In an eighty-eighth aspect according to the preceding aspect, the apparatus comprises:

a filtration unit having a primary chamber and a secondary chamber separated by a semi-permeable membrane;

a blood withdrawal line connected to an inlet of the primary chamber, and a blood return line connected to an outlet of the primary chamber said blood lines being designed to be connected to a patient cardiovascular system;

a blood pump configured to control the flow of blood through the blood lines;

an effluent fluid line connected, at one end thereof, to an outlet of the secondary chamber and, at its other end, optionally connected to a waste container;

at least two fluid lines selected in the group comprising:

a pre-dilution infusion fluid line connected at one end thereof to the blood withdrawal line and at its other end to a first container, a post-dilution infusion fluid line connected at one end thereof to the blood return line and at its other end to a second container, a dialysis fluid line connected at one end thereof to the inlet of the secondary chamber and at its other end to a third fluid container, a pre-blood pump infusion line connected at one end thereof to a fourth container and at its other end to the blood withdrawal line in a region of this latter which is positioned in use upstream the blood pump, one or more syringe lines (50) connected at one end thereof either to the blood withdrawal line (6) or to the blood return line (7) or directly to the patient, and at its other end to a syringe container (S);

the pump or a valve regulator being configured to regulate the flow of fluid through said fluid lines and a control unit being connected to the pump or valve regulator, wherein the process is executed by the control unit and comprises the following steps:

calculating set values of two or more of the fluid flow rates selected in the group including:

a fluid flow rate $Q_{rep1}$ through the pre-dilution infusion fluid line, a fluid flow rate $Q_{rep2}$ through the post-infusion fluid line, a fluid flow rate $Q_{pbp}$ through the pre-blood pump infusion fluid line, a fluid flow rate $Q_{dial}$ through the dialysis liquid fluid line, a fluid flow rate $Q_{syr}$ through the syringe fluid line(s) (50), a fluid flow rate $Q_{eff}$ through the effluent fluid line, by imposing that an emptying time of at least one among the containers of fresh fluid and/or a filling time of the waste container is substantially same as, or multiple of, the emptying time of one or more of the other containers of fresh fluid, storing said calculated set values in identified retrievable memory locations for subsequent use to control said means for regulating the flow of fluid.

In an eighty-ninth aspect according to the preceding aspect, the apparatus comprises:

a filtration unit having a primary chamber and a secondary chamber separated by a semi-permeable membrane;

a blood withdrawal line connected to an inlet of the primary chamber, and a blood return line connected to an outlet of the primary chamber said blood lines being designed to be connected to a patient cardiovascular system;

a blood pump configured to control the flow of blood through the blood lines;

an effluent fluid line connected, at one end thereof, to an outlet of the secondary chamber and, at its other end, optionally connected to a waste container;

at least two fluid lines selected in the group comprising:

a pre-dilution infusion fluid line connected at one end thereof to the blood withdrawal line and at its other end to a first container, a post-dilution infusion fluid line connected at one end thereof to the blood return line and at its other end to a second container, a dialysis fluid line connected at one end thereof to the inlet of the secondary chamber and at its other end to a third fluid container, a pre-blood pump infusion line connected at one end thereof to a fourth container and at its other end to the blood withdrawal line in a region of this latter which is positioned in use upstream the blood pump, one or more syringe lines connected at one end thereof either to the blood withdrawal line or to the blood return line or directly to the patient, and at its other end to a syringe container;

the pump or a valve regulator being configured to regulate the flow of fluid through said fluid lines and a control unit being connected to the pump or valve regulator, wherein the process is executed by the control unit and comprises the following steps:

calculating set values of two or more of the fluid flow rates selected in the group including:

a fluid flow rate $Q_{rep1}$ through the pre-dilution infusion fluid line, a fluid flow rate $Q_{rep2}$ through the post-infusion fluid line, a fluid flow rate $Q_{pbp}$ through the pre-blood pump infusion fluid line, a fluid flow rate $Q_{dial}$ through the dialysis liquid fluid line, a fluid flow rate $Q_{syr}$ through the syringe fluid line or lines, a fluid flow rate $Q_{eff}$ through the effluent fluid line, by that emptying times of at least two among the containers of fresh fluid and, optionally, the filling time of the waste container are multiple of a same reference time $T_r$, and optionally storing said calculated set values in identified retrievable memory locations for subsequent use to control said means for regulating the flow of fluid.

By defining the reference time $T_r$ and a multiplication factor, it is possible to define in relation to each fresh fluid line e.g. the following:

an emptying time of the respective container which is the same of the emptying time of a container relating to another line, an emptying time of the respective container which is the multiple of the emptying time of a container relating to another line, an emptying time of the respective container which is a fraction (A/B where both A and B are integers) of the emptying time of a container relating to another line.

Optionally the above relations may be made with the filling time of the waste container.

In a ninetieth aspect according to the one of the preceding two aspects, the apparatus comprises at least the following three fluid lines:

a pre-dilution infusion fluid line connected to the blood withdrawal line, a post-dilution infusion fluid line connected to the blood return line, a dialysis fluid line connected to the inlet of the secondary chamber;

and wherein the process comprises the following further steps:

allowing selection by an operator of at least one set value
for a parameter selected in the group comprising:
a treatment time T,
a dose $D_{set}$ of the treatment to be delivered to the
patient,
a fluid flow rate $Q_{rep1}$ through the pre-dilution infusion
fluid line,
a fluid flow rate $Q_{rep2}$ through the post-infusion fluid
line,
a fluid flow rate $Q_{pbp}$ through the pre-blood pump
infusion fluid line,
a fluid flow rate $Q_{dial}$ through the dialysis liquid fluid
line,
a fluid flow rate $Q_{eff}$ through the effluent fluid line,
a fluid removal rate $Q_{pfr}$ from the patient,
determining the weight or volume $W_i$, $V_i$ of the respective
container at the beginning of the treatment or at a
prefixed checkpoint or responsive to an operator's
input,
calculating the set value for the fluid flow rate through
each of the above-listed fluid lines by imposing that
emptying times of at least two among the containers of
fresh fluid and, optionally, the filling time of the waste
container are multiple of a same reference time $T_r$.
In a ninety-first aspect according to the preceding aspect,
the emptying time of each given of said first, second, third
and fourth containers and/or the filling time of the waste
container is substantially the same as, or multiple of, the
emptying time of one or more other of said first, second,
third and fourth containers, said set value for the fluid flow
rate through each of the above-listed three fluid lines being
calculated dividing said weight or volume $W_i$, $V_i$ of the
respective container by the value of reference time $T_r$.
In a ninety-second aspect according to the one of the
preceding aspects from $87^{th}$ to $91^{st}$, the calculation of
reference time $T_r$ may be made as disclosed in connection
with the above apparatus aspects.
In a ninety-third aspect according to the one of the
preceding aspects from $87^{th}$ to $92^{nd}$ the process comprises to:
receive an initial weight or volume $W_i$, $V_i$ of one or more
of said containers,
receive proposed values $Q_i$ of the flow rates for said fluid
lines;
receive the value of an adjustment parameter A defined as
maximum relative change allowed on container change
periods;
calculate the set values of said fluid flow rates $Q_{iset}$ based
on the proposed values $Q_i$, the initial weight or volume
$W_i$, $V_i$ of each container and the value of the adjustment
parameter A.
In a ninety-fourth aspect according to the preceding
aspect the process comprises to:
receive an initial weight or volume $W_i$, $V_i$ of one or more
of said containers,
receive proposed values $Q_i$ of the flow rates for said fluid
lines, which may be either entered by the user or come
from a previous calculation step, e.g. using the math-
ematical relations mentioned in some of the above
aspects,
for each pair of lines and respective containers, generate
ratios of interest $R0_k$, which are reference ratios
between change periods of pairs of containers and are
defined for each pair of lines and respective containers,
K being an integer from 1 to M, with the value of M
pre-stored in the control unit memory or receivable
from a user input;

calculate the containers change periods $T_i=V_i/Q_i$ or
$T_i=W_i/Q_i$ and rank each circuit according to the calcu-
lated container change period, where i=1 to N with $T_i$
increasing with i;
compute all period ratios $R_{ij}=T_i/T_j$, with i>j;
compare each period ratio $R_{ij}$ to the ratios of interest $R0_k$;
verify if there is a k value verifying that $R_{ij}/R0_k$ stays
within a tolerance limit (selectable by the user or preset
in a memory of the computer unit),
compute the number of daily saved container changes and
selecting the ratios $R_{ij}$ providing the largest number of
saved container changes and respecting the above tol-
erance limit;
apply the ratios of interest corresponding to the selected
ratios $R_{ij}$ to compute the optimized flow rates $Q_{iset}$.
In a ninety-fifth aspect according to the ninety-third
aspect the process comprises to:
receive an initial weight or volume $W_i$, $V_i$ of one or more
of said containers,
receive proposed values $Q_i$ of the flow rates for said fluid
lines, which may be either entered by the user or come
from a previous calculation step, e.g. using the math-
ematical relations mentioned in some of the above
aspects,
for each pair of lines and respective containers, generate
ratios of interest $R0_k$, which are reference ratios
between change periods of pairs of containers and are
defined for each pair of lines and respective containers,
K being an integer from 1 to M, with the value of M
pre-stored in the control unit memory or receivable
from a user input;
calculate the containers change periods $T_i=V_i/Q_i$ or
$T_i=W_i/Q_i$ and rank each circuit according to the calcu-
lated container change period, where i=1 to N with $T_i$
increasing with i;
compute all period ratios $R_{ij}=T_i/T_j$, with i>j;
compare each period ratio $R_{ij}$ to the ratios of interest $R0_k$;
for each ratio $R_{ij}$ where a k value exists verifying the
tolerance relation: $(1-A)\cdot R0_k<R_{ij}<(1+A)\cdot R0_k$, compute
the number of daily saved container changes;
select the ratios $R_{ij}$ providing the largest number of saved
container changes;
apply the ratios of interest corresponding to the selected
ratios to compute the optimized flow rates $Q_{iset}$.
A ninety-sixth aspect concerns a process of setting up a
medical apparatus for the delivery or collection of fluid, the
apparatus comprising:
a filtration unit having a primary chamber and a secondary
chamber separated by a semi-permeable membrane;
a blood withdrawal line connected to an inlet of the
primary chamber, and a blood return line connected to
an outlet of the primary chamber said blood lines being
designed to be connected to a patient cardiovascular
system;
a blood pump configured to control the flow of blood
through the blood lines;
an effluent fluid line connected to an outlet of the sec-
ondary chamber;
at least two fluid lines selected in the group comprising:
a pre-dilution infusion fluid line connected to the blood
withdrawal line,
a pre-blood pump infusion line connected to the blood
withdrawal line in a region of this latter which is
positioned in use upstream the blood pump
a post-dilution infusion fluid line connected to the
blood return line, a dialysis fluid line connected to the inlet of the secondary chamber;

means for regulating the flow of fluid through said fluid lines;

a control unit connected to the means for regulating, the method comprising the following steps executable by the control unit:

allow entry by an operator of the set value for at least a first fluid flow rate selected in the group including:

a fluid flow rate $Q_{eff}$ through the effluent fluid line, a fluid flow rate $Q_{rep1}$ through the pre-dilution infusion fluid line, a fluid flow rate $Q_{rep2}$ through the post-infusion fluid line, a fluid flow rate $Q_{pbp}$ through the pre-blood pump infusion fluid line, a fluid flow rate $Q_{dial}$ through the dialysis liquid fluid line, and a fluid removal rate $Q_{pfr}$ from the patient, allow entry of a set value for a prescribed dose $D_{set}$ to be delivered, calculate set values of at least a second and a third of the fluid flow rates of said group of flow rates, based on the said first fluid flow rate set by the operator and on said prescribed dose value $D_{set}$ by applying said prescribed dose value $D_{set}$ and the set value of the first fluid flow rate entered by the operator to mathematical relations stored in a memory connected to the control unit.

In a ninety-seventh aspect according to the ninety-sixth said means for regulating the flow of fluid are controlled based on said set values of the fluid flow rates.

In a ninety-eighth aspect according to any one of the preceding two aspects, said mathematical relations stored in said memory comprise one or more of the following:

a convection-diffusion relation, relating the total fluid flow rate through said infusion fluid lines $Q_{rep1}+Q_{rep2}+Q_{pbp}$ with the fluid flow rate through said dialysis fluid line $Q_{dial}$, a blood pre-dilution relation, relating the flow rate of blood or of plasma $Q_{BLOOD}$, $Q_{PLASMA}$ and the fluid flow rate infused in the blood withdrawal line $Q_{rep1}+Q_{pbp}$ through said pre-dilution infusion fluid line and through said pre-blood pump infusion line, a pre-post relation, relating the fluid flow rates $Q_{rep1}+Q_{pbp}$ through pre-dilution infusion fluid line and pre-blood pump infusion line with the fluid flow rate through the post-dilution infusion line $Q_{rep2}$.

In a ninety-ninth aspect according to any one of the preceding three aspects the process comprises selecting at least two of said relations and calculating the set values of at least the second and third of said fluid flow rates by applying the set value of the prescribed dose and the set value of the first fluid flow rate entered by the operator to the selected mathematical relations.

In a one-hundredth aspect according to any one of the preceding four aspects, the convection-diffusion relation defines a first ratio $R_1$ dividing the total fluid flow rate $Q_{rep1}+Q_{rep2}+Q_{pbp}$ through said infusion fluid lines by the fluid flow rate $Q_{dial}$ through said dialysis fluid line, the blood pre-dilution relation defines a second ratio $R_2$ dividing the flow rate of blood or of plasma $Q_{BLOOD}$, $Q_{PLASMA}$ by the sum of fluid flow rates $Q_{rep1}+Q_{pbp}$ infused in the blood withdrawal line through said pre-dilution infusion fluid line and through said pre-blood pump infusion line, and the pre-post relation defines a third ratio $R_3$ dividing the sum of the fluid flow rates $Q_{rep1}+Q_{pbp}$ through said pre-blood pump infusion line and pre-dilution infusion line by the fluid flow rate $Q_{rep2}$ through said post-dilution infusion line.

In a one-hundred-first aspect according to any one of the preceding five aspects the process may include selection of optimization relations as disclosed in connection with the above apparatus aspects.

In a one-hundred-second aspect according to any one of the preceding apparatus aspects, the apparatus comprises one or more scales weighing one or more of said containers, optionally wherein a corresponding scale is provided for each respective of said containers, said scales being connected to the control unit and sending to the control unit corresponding weight signals, wherein the control unit is configured to receiving the initial weight $W_i$ of one or more of said containers from one or more of said scales.

In a one-hundred-third aspect a data carrier is provided comprising instructions which when executed by the control unit of an apparatus according to any one of the preceding apparatus aspects render said control unit configured to execute the respective steps described in the preceding aspects.

DESCRIPTION OF THE DRAWINGS

Aspects of the invention are shown in the attached drawings, which are provided by way of non-limiting example, wherein.

DETAILED DESCRIPTION

Figure 1:
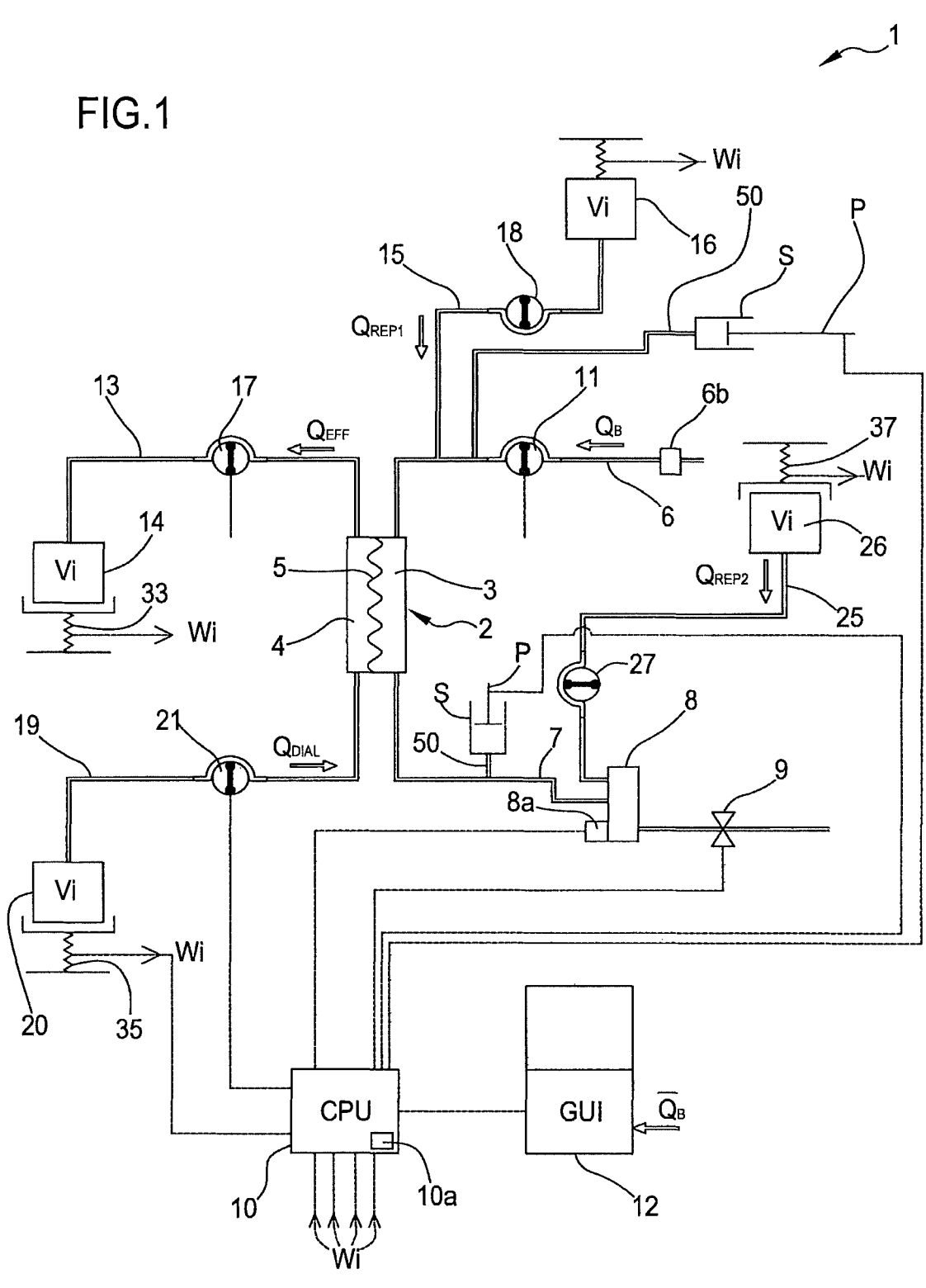
FIGS. 1-4 show schematic representations of blood treatment apparatuses according to aspects of the invention.

FIGS. 1-4 show exemplifying embodiments of apparatus for extracorporeal treatment of blood according to aspects of the invention. Note that same components are identified by same reference numerals in the figures. Also note that—although the present invention is described with specific reference to blood treatment apparatuses—the invention may also refer to apparatuses for handling a plurality of medical fluids, such as nutrients, replacement solutions, serum, or other fluids which need to be controllably injected into or withdrawn from a patient's body.

FIG. 1 shows an extracorporeal blood treatment apparatus 1 which is designed for delivering any one of treatments like hemodialysis, hemofiltration, hemodiafiltration, ultrafiltration. The apparatus 1 comprises a filtration unit 2 having a primary chamber 3 and a secondary chamber 4 separated by a semi-permeable membrane 5; depending upon the treatment the membrane of the filtration unit may be selected to have different properties and performances.

A blood withdrawal line 6 is connected to an inlet of the primary chamber 3, and a blood return line 7 is connected to an outlet of the primary chamber 3. In use, the blood withdrawal line 6 and the blood return line 7 are connected to a needle or to a catheter or an implanted port or other access device (not shown) which is then placed in fluid communication with the patient vascular system, such that blood may be withdrawn through the blood withdrawal line, flowed through the primary chamber and then returned to the patient's vascular system through the blood return line. An air separator, such as a bubble trap 8, may be present on the blood return line; moreover, a safety clamp 9 controlled by a control unit 10 may be present on the blood return line downstream the bubble trap 8. A bubble sensor 8a, for instance associated to the bubble trap 8 or coupled to a portion of the line 7 between bubble trap 8 and clamp 9 may be present: if present, the bubble sensor is connected to the control unit 10 and sends to the control unit signals for the control unit to cause closure of the clamp 9 in case one or more bubbles are detected. As shown in FIG. 1, the blood flow through the blood lines is controlled by a blood pump 11, for instance a peristaltic blood pump, acting either on the blood withdrawal line (as shown e.g. in FIG. 1) or on the blood return line. An operator may enter a set value for the blood flow rate $Q_{BLOOD}$ through a user interface 12 and the control unit 10, during treatment, is configured to control the blood pump based on the set blood flow rate. Note that, alternatively, the blood pump 11 may be automatically controlled with no need of user input: in that case control unit may control the blood pump at a prefixed flow rate or at a flow rate calculated based on other parameters such as, for instance, pressure detected upstream the blood pump; if the blood pump 11 is controlled based on the pressure signal detected upstream the blood pump then a pressure sensor 6b is present in the tract 6a of bloodline upstream the blood pump 11: for instance the control unit 10 may be designed to drive the blood pump in a manner to keep the pressure detected by pressure sensor 6b within a prefixed range, or below a prefixed threshold.

Going back to FIG. 1, an effluent fluid line 13 is connected, at one end, to an outlet of the secondary chamber 4 and, at another end, to an effluent fluid container 14 collecting the fluid extracted from the secondary chamber. The embodiment of FIG. 1 also presents a pre-dilution fluid line 15 connected to the blood withdrawal line: this line 15 supplies replacement fluid from an infusion fluid container 16 connected at one end of the pre-dilution fluid line. Note that a post-dilution fluid line 25 may also be present connecting an infusion fluid container 26 to the blood return line, for instance in correspondence of bubble trap 8. When the apparatus (as in FIG. 1) includes both a pre-dilution 15 and a post infusion fluid line 25 each infusion fluid line may be connected to a respective infusion fluid container or the two infusion fluid lines could receive infusion fluid from a same infusion fluid container or other fluid source. An effluent fluid pump 17 operates on the effluent fluid line under the control of said control unit 10 to regulate the flow rate $Q_{eff}$ across the effluent fluid line. Furthermore, an infusion pump 18 operates on the infusion line 15 to regulate the flow rate $Q_{rep1}$ through the pre-dilution fluid line 15. Note that in case of two infusion fluid lines (pre-dilution and post-dilution) each fluid line 15, 25 may cooperate with a respective infusion pump 18, 27 to regulate the flow rate $Q_{rep1}$ and $Q_{rep2}$ through the respective lines. The apparatus of FIG. 1, further includes a dialysis fluid line 19 connected at one end with a dialysis fluid container 20 and at its other end with the inlet of the secondary chamber 4 of the filtration unit. A dialysis pump 21 works on the dialysis fluid line 19 under the control of said control unit 10, to supply fluid from the dialysis liquid container to the secondary chamber at a flow rate $Q_{dial}$.

The dialysis fluid pump 21, the infusion fluid pump 18 (or pumps 18, 27) and the effluent fluid pump 17 are part of means for regulating the flow of fluid through the respective lines and, as mentioned, are operatively connected to the control unit 10 which controls the pumps as it will be in detail disclosed herein below. The control unit 10 is also connected to a memory 10a and to user interface 12, for instance a graphic user interface, which receives operator's inputs and displays the apparatus outputs. For instance, the graphic user interface 12 may include a touch screen, a display screen and/or hard keys for entering user's inputs or a combination thereof.

Figure 2:
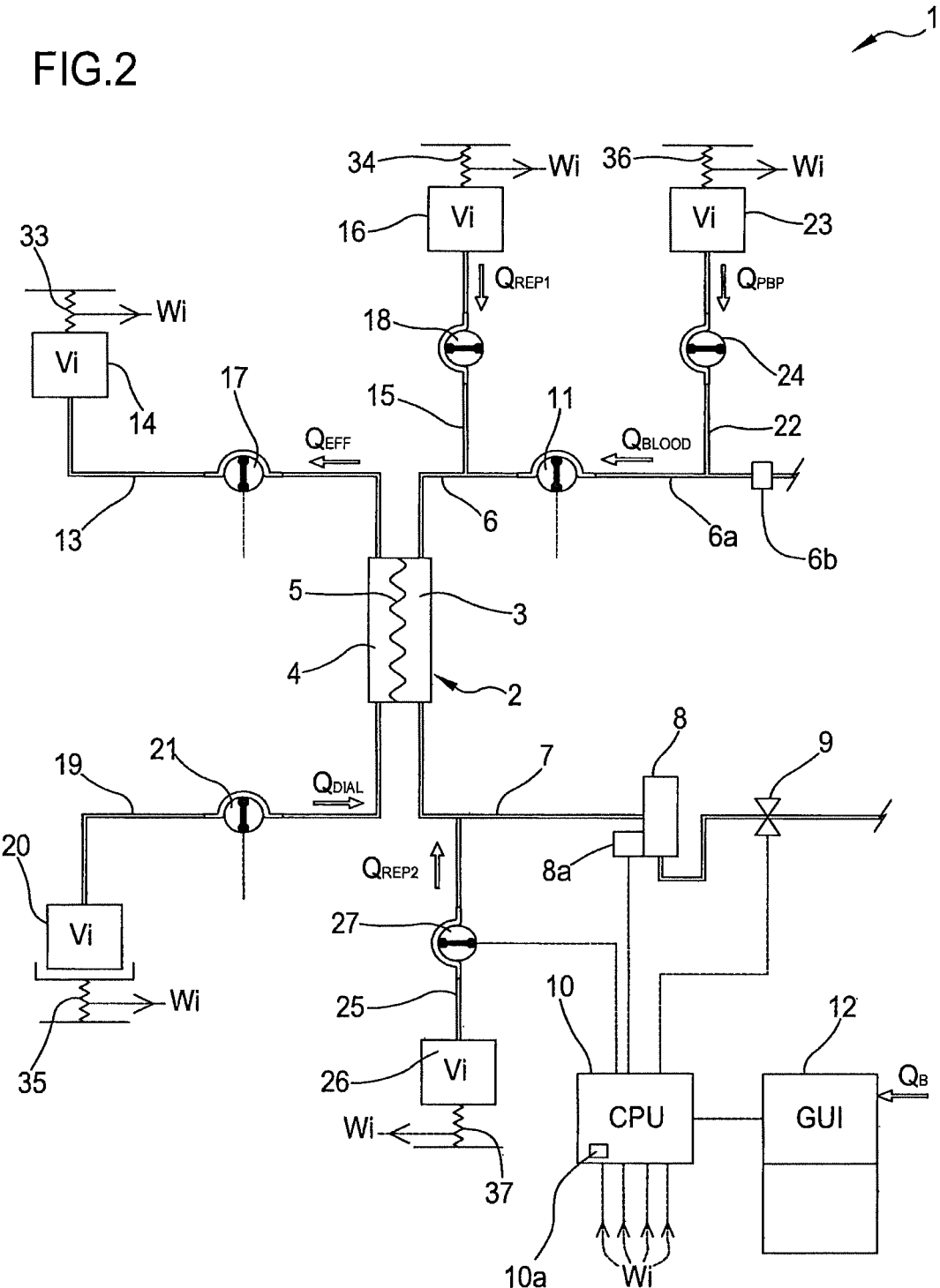

The embodiment of FIG. 2 shows an alternative apparatus 1 where the same components described for the embodiment of FIG. 1 are also present and are identified by same reference numerals and thus not described again. Additionally, the apparatus 1 shown in FIG. 2 presents a further infusion line connected, at one end, with a tract 6a of the blood withdrawal line 6 positioned upstream the blood pump 11 and, at its other end, with a further infusion fluid container 23, which for instance may contain a drug, or a regional anticoagulant such as a citrate solution, or a nutrients solution or other. This further infusion line is herein referred to as pre-blood pump infusion line 22. The means for regulating comprises a pump 24, for instance a peristaltic pump controlled by control unit 10, acting on a segment of the pre-blood pump infusion line to regulate a pre-blood pump infusion rate $Q_{pbp}$.

The apparatus of FIG. 2 may also present a post-dilution line 25 similar to that of the apparatus of FIG. 1: the infusion line 25 in FIG. 2 is connected to the blood return line 7 in a location between the bubble trap 8 and the exit of the filtering unit 2; alternatively the infusion line may be directly connected to bubble trap 8.

Figure 3:
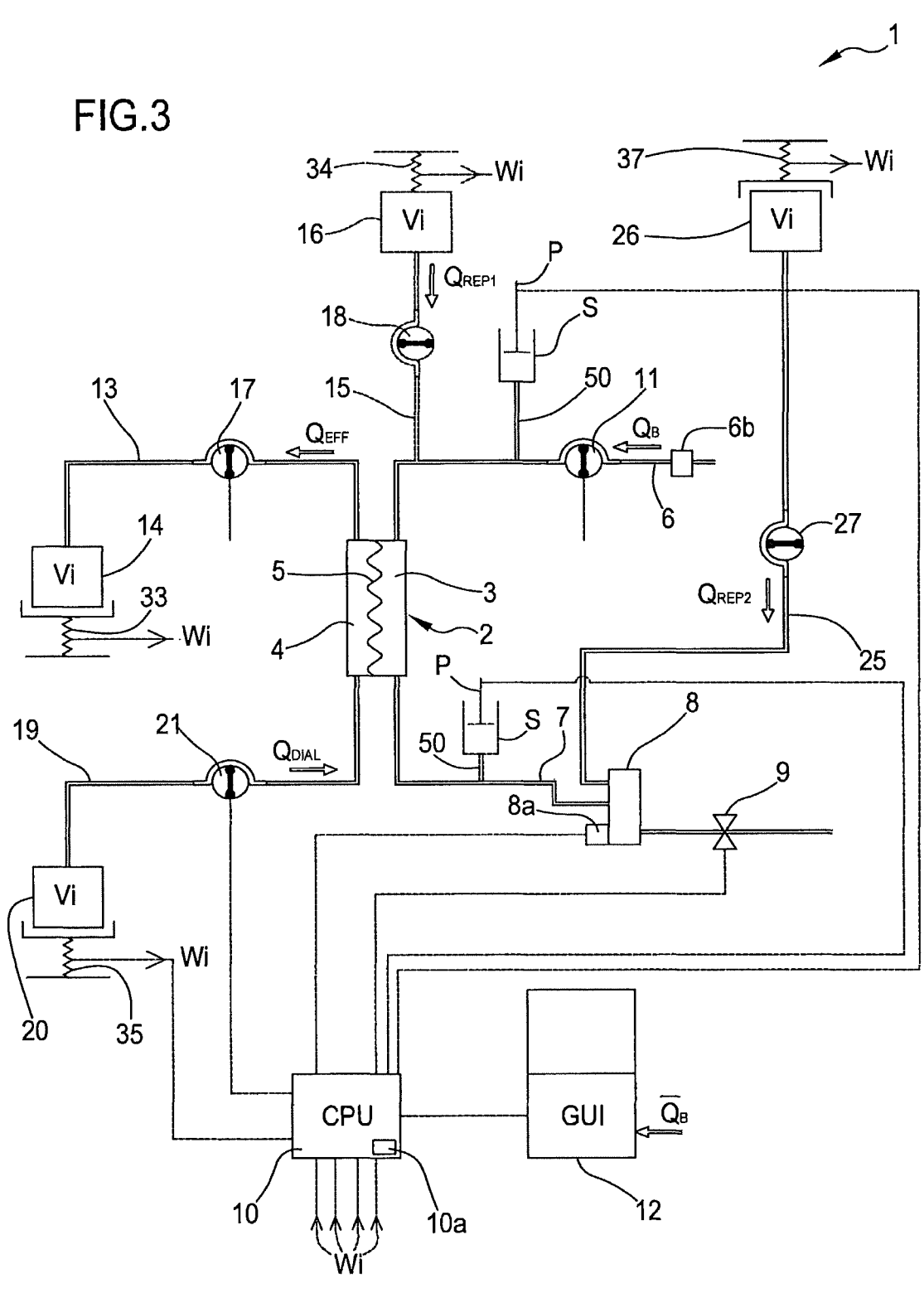

The apparatus of FIG. 3 is similar to that of FIG. 1 but includes only either the post-dilution line 25 with its pump 27 and infusion fluid container 26 or the pre-dilution line 15 with its pump and container (see phantom line).

Figure 4:
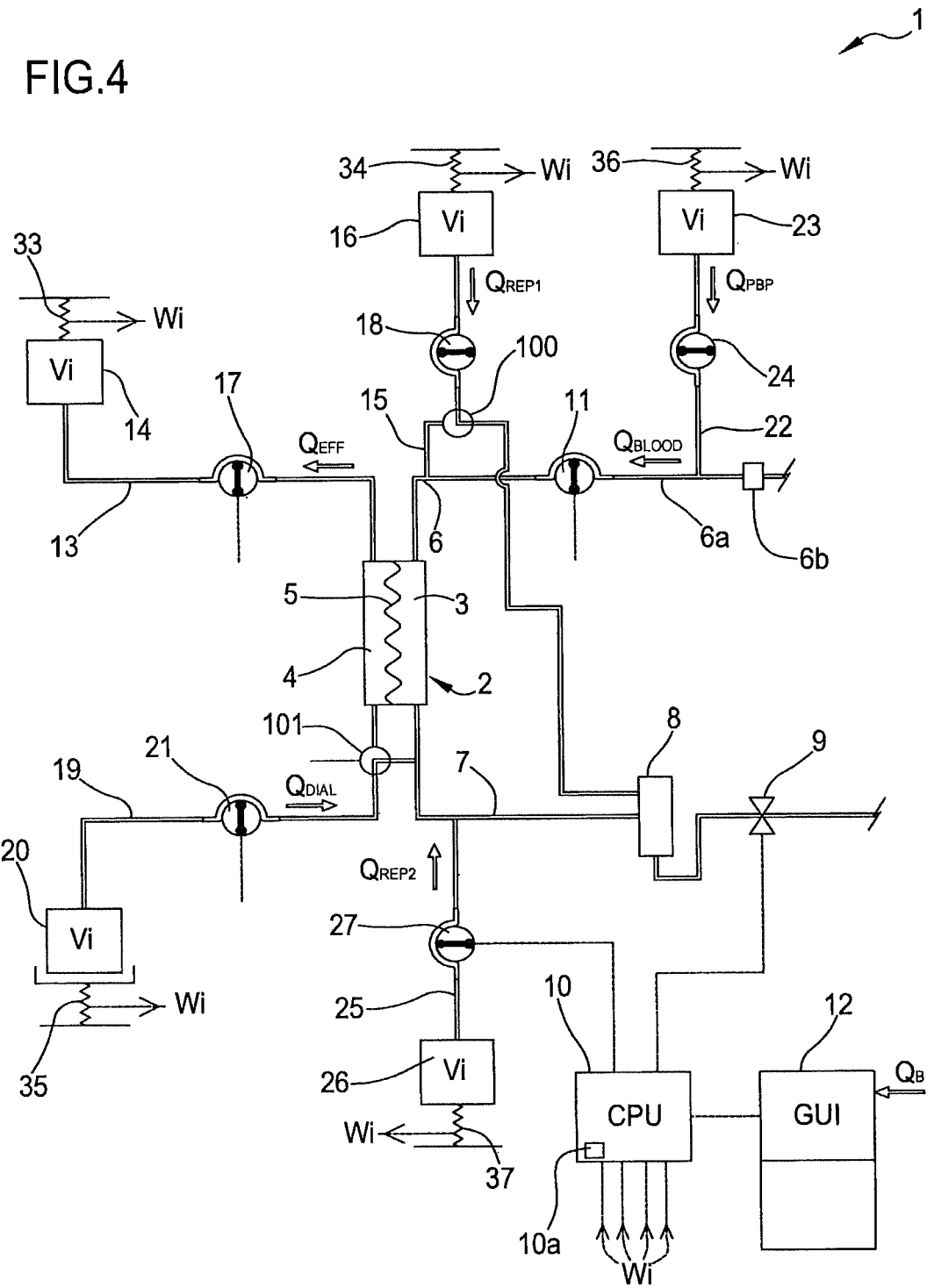

A further embodiment is shown in FIG. 4. In this embodiment, compared to that of FIG. 2, a line switch 101 operates (such as a 3-way valve or a clamp mechanism) on the dialysis fluid line 19 which allows the dialysis line to be selectively coupled either to the inlet of the second chamber 4 or to the return line 7: in this latter case the dialysis line would work as a post-dilution line. Moreover a further line switch 100 operates on the infusion line 15 which allows the infusion line 15 to be selectively coupled either to the blood withdrawal line or to the blood return line. A further post-dilution line 27 (see phantom line in FIG. 4) may or may not be present.

Of course the above described blood treatment apparatus are of exemplifying character only and further variants may be envisaged without departing from the scope of the invention.

For instance the above apparatuses may also include a syringe pump S connected via a respective line to one of the blood lines 6 and 7. In FIGS. 1 and 3 the syringe pump S is connected to the blood withdrawal line 6, upstream the blood pump. Syringe pump S may be used to inject medicaments, anticoagulants or other fluids. Although not shown also the circuits shown in FIGS. 2 and 4 may include a syringe connected either to the blood withdrawal line or to the blood return line.

The means for regulating have been described as one or more pumps (in particular of the peristaltic type); however it is not to be excluded that other flow regulating means such as valves or combinations of pumps and valves may be used.

Dose Definitions

In the present specification, dose refers to a flow rate or to a combination of flow rates.

For example, one of the following magnitudes may be used as dose:

effluent dose $D_{eff}$: the flow rate across the effluent line $Q_{eff}$;

convective dose $D_{conv}$: the sum of the flow rates $Q_{rep}+Q_{pbp}+Q_{pfr}$, where $Q_{pfr}$ represents the patient fluid removal rate, $Q_{rep}$ is the flow rate through the infusion line or lines (e.g. $Q_{rep1}+Q_{rep2}$) connected directly to the patient or connected to the blood circuit downstream the blood pump and $Q_{pbp}$ is the flow rate through the pre-blood pump infusion line, diffusive dose $D_{dial}$: the flow rate $Q_{dial}$ of fluid supplied to the filtration unit secondary chamber.

urea dose $D_{urea}$: estimated urea clearance; note that a first approximated expression assumes that filter Urea clearance is more or less identical to effluent flow rate $Q_{eff}$; alternatively a urea monitor could be placed on the effluent line in order to measure an actual value of the urea clearance; in a further alternative, an estimate of urea clearance more accurate than $Q_{eff}$, especially when operating with large flow rates or small filters (paediatric conditions), may be provided by the following equations:

a) For purely diffusive mode (where there is no infusion of replacement fluid and where the patient fluid removal rate is zero or substantially zero) and counter-courant flow configuration (fluids in the chambers of the filtration unit 2 are countercurrent):

$$Z = \frac{Qpw_{inlet}}{Qdial}$$

$$NT = \frac{S/RT}{Qpw_{inlet}}$$

$$K(Qpw_{inlet}, Qdial) = Qpw_{inlet} \times \frac{\exp[NT \times (1-Z)] - 1}{\exp[NT \times (1-Z)] - Z} \text{ if } Z \neq 1$$

$$K(Qpw_{inlet}, Qdial) = Qpw_{inlet} \times \frac{NT}{NT+1} \text{ if } Z = 1$$

where: S (effective surface area) is dependent on the hemodialyzer (as filtration unit 2) in use; RT is total mass transfer resistance dependent of the hemodialyzer in use (membrane properties, filter design) and the solute of interest, in this case urea; and $Qpw_{inlet}$ is the plasma water flow rate at the inlet of the filtration unit 2 b) In case of presence of both $Q_{dial}$ and of one or more infusions of fluid, then:

$$y = \exp\left(\frac{SC \times Qfil}{S/RT}\right) - 1$$

$$f = \left(\frac{Qpw_{inlet} - SC \times Qfil}{Qpw_{inlet}} \times \frac{Qdial \div SC \times Qfil}{Qdial}\right)^{1/y}$$

$$K(Qpw_{inlet}, Qdial, Qfil) = \frac{Qpw_{inlet} \times Qdial - f \times}{(Qpw_{inlet} - SC \times Qfil) \times (Qdial + SC \times Qfil)}{Qdial - f \times (Qpw_{inlet} - SC \times Qfil)}$$

where: S (effective surface area) is dependent on the hemodialyzer in use; $Q_{fil}=Q_{pbp}+Q_{rep}+Q_{pfr}$ (again, $Q_{pfr}$ represents the patient fluid removal rate, $Q_{rep}$ is the flow rate through the infusion line or lines connected directly to the patient or connected to the blood circuit downstream the blood pump and $Q_{pbp}$ is the flow rate through the pre-blood pump infusion line); and $Qpw_{inlet}$ is the plasma water flow rate at the inlet of the filtration unit 2.

clearance dose: an estimated clearance for a given solute; for certain solutes a first approximated expression assumes that filter solute clearance is more or less identical to effluent flow rate $Q_{eff}$; alternatively solute clearance may be estimated as function of all flow settings and of dialyzer/filter related parameters; alternatively appropriate sensors could be placed to measure conductivity or concentration and thereby allow calculation of an actual clearance for a given solute (e.g. sodium), for instance using one of the methods described in EP patent n. 0547025 or EP patent n. 0658352 or EP patent n. 0920887. In a further alternative the equations of above paragraphs a) and b) as described for the urea clearance could be used with RT and SC adapted to take into account the specific solute.

In the course of the following description reference will be made to the above dose definitions which are relating to doses not normalized to patient body weight (BW) or patient surface area (PA). Of course the same principles and formulas below described could be normalized to body weight or patient surface area by dividing the dose value by either body weight BW or surface area PA.

$$\text{Normalized Dose} = \text{Dose}/\text{BW}$$

or $$N\text{Dose} = \text{Dose}/PA \times 1.73 \text{ (when normalised to a 1.73}$$
$$\text{m}^2 \text{ surface area patient)}$$

Furthermore, the above defined doses could be corrected to take into account the predilution effect, when a fluid replacement line is present upstream the treatment unit, such as lines 15 and 22 in the enclosed drawings. Each of the above defined doses could be corrected multiplying the dose value times a dilution factor $F_{dilution}$:

$$\text{Dose}_{corr\_xxx} = F_{dilution} \times \text{Dose}_{\_xxx} \text{ (with } xxx = \text{eff,conv,}$$
$$\text{dial,etc)}$$

The dilution factor $F_{dilution}$ may be defined according to one of the following:

$$\text{Blood dilution factor: } Fdilution_{blood} = \frac{Qblood}{Qblood + Qpre}$$

$$\text{Plasma dilution factor: } Fdilution_{plasma} =$$

$$\frac{Qp}{Qp + Qpre} = \frac{(1 - Hct) \times Qblood}{(1 - Hct) \times Qblood + Qpre}$$

$$\text{Plasma water dilution factor: } Fdilution_{pw} =$$

$$\frac{Qpw}{Qpw + Qpre} = \frac{(1 - Hct) \times Fp \times Qblood}{(1 - Hct) \times Fp \times Qblood + Qpre}$$

Where $Q_{pre}$ is the total predilution infusion rate (where two infusion lines are present upstream the treatment unit, as lines 15 and 22, $Q_{pre}$ combines PBP infusion 15 and pre-replacement infusion 22)

$Q_{BLOOD}$: blood flow rate
$Q_{PLASMA}$: plasma flow rate
$Q_{pw}$: plasma water flow rate
Hct: haematocrit
$F_p$: plasma water fraction, which is a function of total protein concentration (typical value Fp=0.95)

In practice, the effluent dose corrected for the predilution effect would be:

$$\text{Dose}_{corr\_eff} = F_{dilution} \times \text{Dose}_{\_eff}.$$

The Control Unit

The control unit 10 is connected to the various sensors, to the means for regulating the flow rate through the various lines (in the above examples this means comprises the pumps active on the lines and the switch valves) and to the user interface. The control unit 10 may comprise a digital processor (CPU) and necessary memory (or memories) such as memory 10a, an analogical type circuit, or a combination thereof. In the course of the present description it is indicated that the control unit is "configured" or "programmed" to execute certain steps: this may be achieved in practice by any means which allow configuring or programming the control unit. For instance, in case of a control unit comprising one or more CPUs, a program may be stored in an appropriate memory containing instructions which, when executed by the control unit, cause the control unit to execute the steps herein described. Alternatively, if the control unit is of an analogical type, then the circuitry of the control unit may be designed to include circuitry configured in use to execute the steps herein disclosed.

In the example of FIG. 1, the control unit 10 is configured to execute a flow-rate setup procedure as described here below. This procedure comprises to receive a prescribed dose value $D_{set}$, a prescribed value for the a fluid removal rate $Q_{pfr}$ from the patient, and a setting for the blood flow rate $Q_{BLOOD}$ (see step 200 in FIG. 5).

The memory 10a associated with or connected to the control unit 10 stores a plurality of mathematical relations correlating the fluid flow rates $Q_{rep1}$, $Q_{rep2}$ and $Q_{dial}$. The mathematical relations stored in said memory may be the following:

a convection-diffusion relation, relating the total fluid flow rate through said infusion fluid lines+patient fluid removal rate $Q_{rep1} + Q_{rep2} + Q_{pfr}$ with the fluid flow rate through said dialysis fluid line $Q_{dial}$; the convection-diffusion relation may define in practice a first ratio $R_1 = (Q_{rep1} + Q_{rep2} + Q_{pfr})/(Q_{dial})$, a blood pre-dilution relation, relating the flow rate of blood or of plasma $Q_{BLOOD}$ or $Q_{PLASMA}$ and the fluid flow rate infused in the blood withdrawal line $Q_{rep1}$ through said pre-dilution infusion fluid line 15; the blood pre-dilution relation may define a second ratio $R_2 = Q_{BLOOD}/(Q_{rep1})$ or $R_2 = Q_{PLASMA}/(Q_{rep1})$;

a pre-post relation, relating the fluid flow rates $Q_{rep1}$ through pre-dilution infusion fluid line with the fluid flow rate through the post-dilution infusion line $Q_{rep2}$; the pre-post relation may define in practice a third ratio $R_3 = (Q_{rep1})/(Q_{rep2})$.

The control unit 10 allows the user, e.g. through user interface 12, to select e.g. two of said relations (step 201 in FIG. 5) and then may calculate the set values of all flow rates $Q_{rep1}$, $Q_{rep2}$, $Q_{dial}$ and $Q_{eff}$ (step 203 in FIG. 5) by applying the set value of the dose $D_{set}$ and the set value of fluid removal rate $Q_{pfr}$ entered by the operator to the mathematical relations selected by the user and to the following fluid balance equation which needs to be satisfied in order to maintain the fluid balance in line with the prescription:

$$Q_{rep1} + Q_{rep2} + Q_{dial} + Q_{pfr} = Q_{eff} \tag{FBE}$$

In case a syringe pump (not shown in FIGS. 1-4) is also present for injecting an auxiliary fluid, e.g. heparin, in the blood withdrawal line, then the above equation should be modified accordingly to account for the syringe flow rate.

Note that preset values for each one of said first, second and third ratios $R_1$, $R_2$, $R_3$ may be pre-stored in the memory or that the control unit may allow entry by an operator of a set value for each one of said first, second and third ratios $R_1$, $R_2$, $R_3$, e.g. via the user interface 12. In this last case, the control unit may be configured to:

display on the graphic user interface an indicium prompting a user to select the value for said first flow rate, display on the graphic user interface an indicium allowing selection of the mathematical relations the user intends to select, detecting selection of a mathematical relation and display an indicium allowing selection of a set value or of a range for the corresponding ratio.

In one alternative, the memory 10a of the apparatus of FIG. 1 may store a plurality of optimization criteria, which the control unit 10 may use to calculate the set values for $Q_{rep1}$, $Q_{rep2}$, $Q_{dial}$, $Q_{eff}$ in alternative or in combination with the above ratios $R_1$, $R_2$, $R_3$ (step 203).

For instance, optimization criteria stored in memory 10a may comprise a first optimization criterion imposing that an emptying time of at least one among the containers of fresh fluid 16, 20, 21, 26 and/or a filling time of the waste container is substantially same as, or multiple of, or proportional to the emptying time of one or more of the other containers of fresh fluid (See below section "synchronization of containers emptying or filling"). A second optimization criterion stored in the memory 10a may impose that fluid consumption through the fluid lines is minimized. A third optimization criterion stored in memory 10a may impose that a life time of filtration unit 2 is maximized. A fourth optimization criterion stored in the memory 10a may impose that urea clearance or dialysance of a given solute is maximized.

In practice, if optimization criteria are stored in memory 10a, the control unit 10 may be configured to allow the user to select (step 202), e.g. via the user interface 12, the criteria he wants to have satisfied and may be further configured to calculate the set values for $Q_{rep1}$, $Q_{rep2}$, $Q_{dial}$, $Q_{eff}$ based on the selected optimization criteria and on the above mentioned fluid balance equation (FBE).

Alternatively, the control unit may be configured to allow the user to select one or more of said criteria, e.g. maximization of fluid consumption, and one of the mathematical relations (e.g. the value for ratio R1). Then the control unit would calculate the set values for $Q_{rep1}$, $Q_{rep2}$, $Q_{dial}$, $Q_{eff}$ using said selected criterion and mathematical relation account being taken of above mentioned fluid balance equation (FBE).

Figure 5:
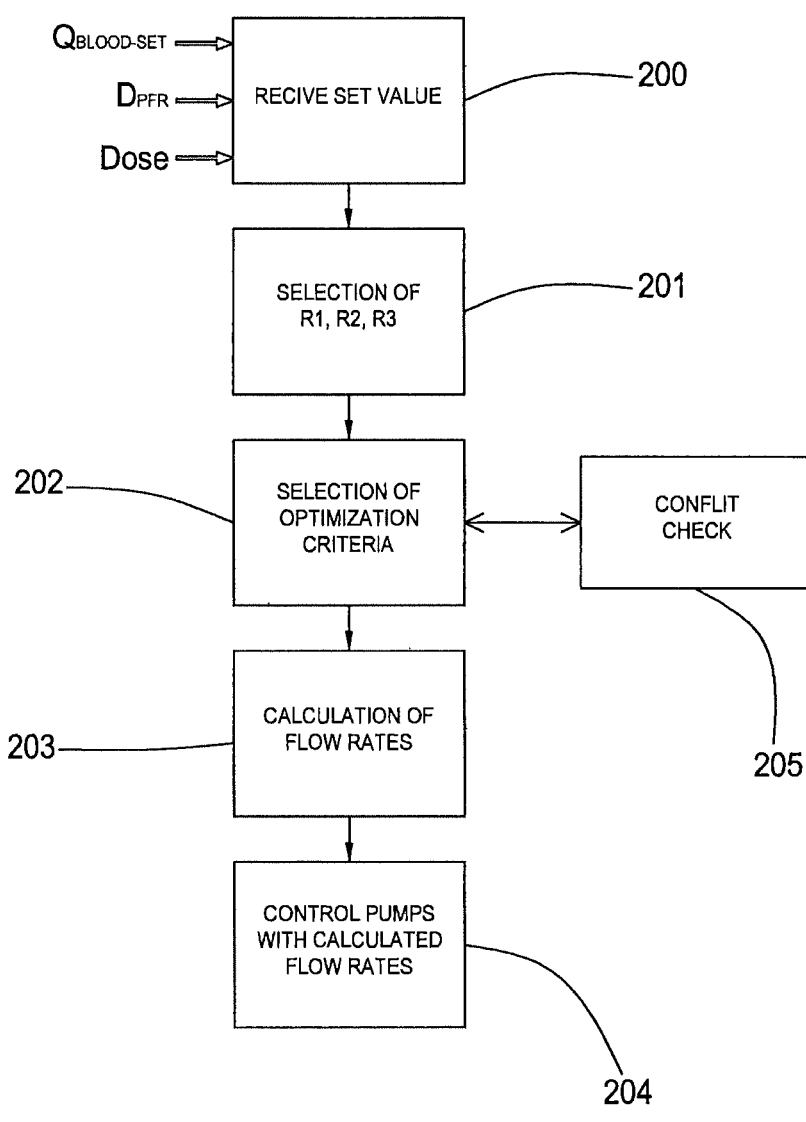
FIG. 5 is a flowchart showing calculation of set flow rates in a medical apparatus, e.g. of the type of FIGS. 1-4, according to an aspect of the invention.

If the memory 10a stores a plurality of mathematical relations and a plurality of optimization criteria, and if the user contemporaneously selects a number of optimization criteria together with a number of relations, then the control unit 10 may also be configured to determine if said selected criteria and said selected mathematical relations are compatible or conflicting (see conflict check step 205 in FIG. 5). In case the selected criteria and the selected mathematical relations are compatible, then the set flow rates are calculated based on both the selected mathematical relations and optimization criteria. On the other hand, in case the selected criteria and selected mathematical relations are conflicting, the control unit may be configured to execute one or more of the following sub-steps:

inform the user; the user has then the power to re-enter compatible selections;

assign a priority ranking to the selected criteria and mathematical relations; the priority ranking is either predetermined or user adjustable: in any case the control unit is configured to ignore criteria or mathematical relations as soon as flow rates have been calculated from the prioritized criteria/mathematical relations;

define a compromise between conflicting criteria or mathematical relations using preset rules.

In accordance with a variant, as already explained in the summary section the control unit may use the flow-rate setup procedure to initially calculate the flow rates set values through the various lines and during a first interval in the treatment control the means for regulating using said calculated set values. Then, after a certain time interval or upon detection of a user input, the control unit may recalculate the set values for the flow rates through the various lines exclusively based on one or more optimization criteria and, apply the newly calculated set values during a second time period subsequent to the first time period. For instance the flow-rate setup procedure may allow setting of the flow rates such that a certain delivered dose is attained. On the other hand, if at a certain point the user wants to privilege bag-emptying synchronization he may select to impose the first optimization criteria so that the control unit may recalculate the set values of the flow-rates allowing to synchronize as possible the emptying of the fluid bags.

In the example of FIG. 2, the apparatus has a further line 22 and a further fluid flow rate $Q_{pbp}$ needs to be set. The features disclosed above in connection with FIG. 1 are also present in the apparatus of FIG. 2. The control unit 10 is configured to receive a prescribed dose value $D_{set}$, a prescribed value for the a fluid removal rate $Q_{pfr}$ from the patient, and a setting for the blood flow rate $Q_{BLOOD}$ (see step 200 in FIG. 5). The control unit will then repeat the steps described in connection with the embodiment of FIG. 1 with the difference that one more mathematical relation or one more optimization criteria needs to be selected and used by the control unit 10 because the set values to calculate are $Q_{rep1}$, $Q_{rep2}$, $Q_{dial}$, $Q_{eff}$ and $Q_{pbp}$.

Note that in this case the memory 10a associated with or connected to the control unit 10 stores a plurality of mathematical relations correlating the fluid flow rates $Q_{rep1}$, $Q_{rep2}$, $Q_{pbp}$ and $Q_{dial}$. The mathematical relations stored in said memory may be the following:

a convection-diffusion relation, relating the total fluid flow rate through said infusion fluid lines+the patient fluid loss rate $Q_{rep1}+Q_{rep2}+Q_{pbp}+Q_{pfr}$ with the fluid flow rate through said dialysis fluid line $Q_{dial}$; the convection-diffusion relation may define in practice a first ratio $R_1=(Q_{rep1}+Q_{rep2}+Q_{pbp}+Q_{pfr})/(Q_{dial})$, a blood pre-dilution relation, relating the flow rate of blood or of plasma $Q_{BLOOD}$ or $Q_{PLASMA}$ and the fluid flow rate infused in the blood withdrawal line $Q_{rep1}+Q_{pbp}$ through said pre-dilution infusion fluid line 15 and through said pre-blood pump infusion line 21; the blood pre-dilution relation may define a second ratio $R_2=Q_{BLOOD}/(Q_{rep1}+Q_{pbp})$ or $R_2=Q_{PLASMA}/(Q_{rep1}+Q_{pbp})$;

a pre-post relation, relating the fluid flow rates $Q_{rep1}+Q_{pbp}$ through pre-dilution infusion fluid line 15 and pre-blood pump infusion line 21 with the fluid flow rate $Q_{rep2}$ through the post-dilution infusion line; the pre-post relation may define in practice a third ratio $R_3=(Q_{rep1}+Q_{pbp})/(Q_{rep2})$.

In the example of FIG. 3, the apparatus has one line (line 15 or 25) less than the apparatus of FIG. 1. The features disclosed above in connection with FIG. 1 are also present in the apparatus of FIG. 3. The control unit 10 is configured to receive a prescribed dose value $D_{set}$, a prescribed value for the a fluid removal rate $Q_{pfr}$ from the patient, and a setting for the blood flow rate $Q_{BLOOD}$ (see step 200 in FIG. 5). The control unit will then repeat the steps described in connection with FIG. 1 with the difference that one less mathematical relation or one less optimization criteria needs to be selected and used by the control unit 10 because the set values to calculate are $Q_{rep}$, $Q_{dial}$, and $Q_{eff}$. Note that in this case the memory 10a associated with or connected to the control unit 10 stores a plurality of mathematical relations correlating the fluid flow rates $Q_{rep}$ and $Q_{dial}$. The mathematical relations stored in said memory may include a convection-diffusion relation, relating the fluid flow rate through said infusion fluid line $Q_{rep}$+the patient fluid loss rate $Q_{pfr}$ with the fluid flow rate through said dialysis fluid line $Q_{dial}$; the convection-diffusion relation may define in practice a first ratio $R_1=(Q_{rep}+Q_{pfr})/(Q_{dial})$.

In the example of FIG. 4, compared to the apparatus of FIG. 1, a further line 22 is present and a thus further fluid flow rate $Q_{pbp}$ needs to be set. The features disclosed above in connection with FIG. 1 are also present in the apparatus of FIG. 4. The control unit 10 is configured to receive a prescribed dose value $D_{set}$, a prescribed value for the a fluid removal rate $Q_{pfr}$ from the patient, and a setting for the blood flow rate $Q_{BLOOD}$ (see step 200 in FIG. 5). The control unit will then repeat the steps described in connection with FIG. 1 with the difference that one more mathematical relation or one more optimization criteria may be selected and used by the control unit 10 because the set values to calculate are $Q_{rep1}$, $Q_{rep2}$, $Q_{dial}$, $Q_{eff}$ and $Q_{pbp}$. Note that in this case the memory 10a associated with or connected to the control unit 10 stores a plurality of mathematical relations correlating the fluid flow rates $Q_{rep1}$, $Q_{rep2}$, $Q_{pbp}$ and $Q_{dial}$. The mathematical relations stored in said memory may be the following:

a convection-diffusion relation, relating the total fluid flow rate through said infusion fluid lines+the patient fluid removal rate $Q_{rep1}+Q_{rep2}+Q_{pbp}+Q_{pfr}$ with the fluid flow rate through said dialysis fluid line $Q_{dial}$; the convection-diffusion relation may define in practice a first ratio $R_1=(Q_{rep1}+Q_{rep2}+Q_{pbp}+Q_{pfr})/(Q_{dial})$, a blood pre-dilution relation, relating the flow rate of blood or of plasma $Q_{BLOOD}$ or $Q_{PLASMA}$ and the fluid flow rate infused in the blood withdrawal line $Q_{rep1}$ through said pre-dilution infusion fluid line 15 and through said pre-blood pump infusion line 21; the blood pre-dilution relation may define a second ratio $R_2=Q_{BLOOD}/(Q_{rep1}+Q_{pbp})$ or $R_2=Q_{PLASMA}/(Q_{rep1}+Q_{pbp})$;

a pre-post relation, relating the fluid flow rates $Q_{rep1}+Q_{pbp}$ through pre-dilution infusion fluid line 15 and pre-blood pump infusion line 21 with the fluid flow rate $Q_{rep2}$ through the post-dilution infusion line; the pre-post relation may define in practice a third ratio $R_3=(Q_{rep1}+Q_{pbp})/(Q_{rep2})$.

Optimization Criterion: Synchronization of the Emptying and/or Filling Time of the Containers Again referring to the circuits of FIGS. 1-4, the control unit may be configured to store and use optimization criteria for the calculation of the set flow rates: as mentioned the optimization criteria may be used in combination with mathematical relations, e.g. in combination with use of ratios $R_1$, $R_2$, $R_3$. In the example of FIG. 1, the control unit 10 may be configured to calculate set values of fluid flow rate $Q_{rep1}$ through the pre-dilution infusion fluid line 15, of fluid flow rate $Q_{rep2}$ through the post-infusion fluid line 25, and of fluid flow rate $Q_{dial}$ through the dialysis fluid line 27, by imposing that an emptying time of the containers of fresh fluid 16, 20, 26 is either identical to, or proportional to, or multiple of the emptying time of one of the other containers of fresh fluid. In the example of FIG. 2, the control unit 10 may be configured to calculate set values of fluid flow rate $Q_{rep1}$ through the pre-dilution infusion fluid line 15, of fluid flow rate $Q_{rep2}$ through the post-infusion fluid line 25, of fluid flow rate $Q_{dial}$ through the dialysis fluid line 27, and of $Q_{pbp}$ through line 22 by imposing that an emptying time of the containers of fresh fluid 16, 20, 23, 26 is either identical to or multiple of or proportional to the emptying time of one of the other containers of fresh fluid. In the example of FIG. 3, the control unit 10 may be configured to calculate set values of fluid flow rate $Q_{rep2}$ through the post-infusion fluid line 25, of fluid flow rate $Q_{dial}$ through the dialysis fluid line 27 by imposing that an emptying time of one of the containers of fresh fluid 20, 26 is either identical to or multiple of or proportional to the emptying time of the other container of fresh fluid 26, 20. Finally, in the example of FIG. 4, the control unit 10 may be configured to calculate set values of fluid flow rate $Q_{rep1}$ through the pre-dilution infusion fluid line 15, of fluid flow rate $Q_{dial}$ through the dialysis fluid line 27, and of $Q_{pbp}$ through line 22 by imposing that an emptying time of the containers of fresh fluid 16, 20, 23 is either identical to or proportional to or multiple of the emptying time of one of the other containers of fresh fluid. In other words, the control unit may be configured to calculate the set flow rates through the various lines of fresh fluid such as to either synchronize the emptying time of all containers (e.g. bags) or to make sure that the emptying time of each container is a multiple of a reference emptying time so that the frequency of bag/container substitutions is minimized or at least reduced. In a further aspect which may be combined to the above synchronization criteria, the control unit may also be configured to calculate the set value of the fluid flow rate $Q_{eff}$ through the effluent fluid line 13, by imposing that the filling time of the waste container 14 is substantially same as, proportional to, or multiple of the emptying time of one or more of the other containers of fresh fluid.

Figure 6:
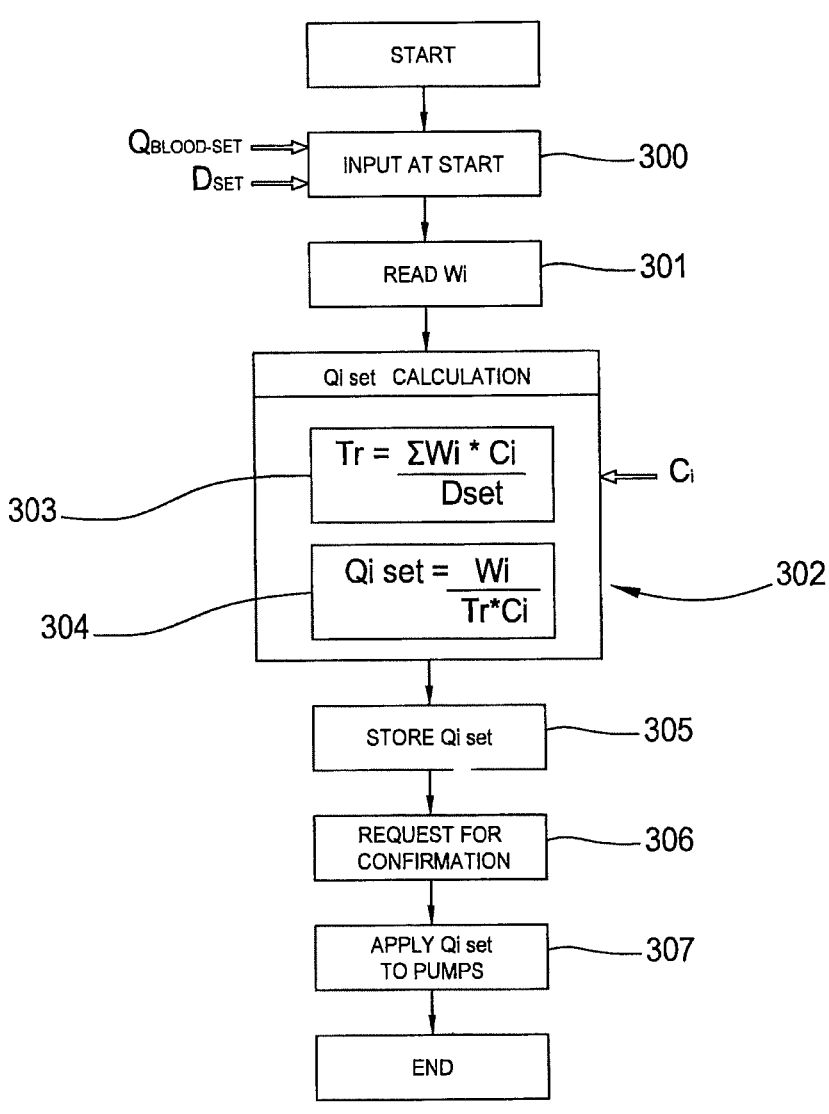
FIG. 6 is a flowchart showing calculation of set flow rates in a medical apparatus, e.g. of the type of FIGS. 1-4, according to another aspect of the invention.

In accordance with a first solution, see the flowchart of FIG. 6, the control unit 10 is configured to allow selection by an operator of a set value for the treatment dose $D_{set}$ to be delivered to the patient during the treatment (step 300). Alternatively, the set value of the dose may be received through an external channel or be pre-stored in a memory connected to the control unit. This set value may be for instance an effluent dose flow rate $D_{eff\_set}$, which is the prescribed mean value of the flow rate through the effluent line, or a convective dose flow rate $D_{conv\_set}$, which is the prescribed mean value of the sum of the flow rates $Q_{rep1}$, $Q_{pbp}$, $Q_{rep2}$ through any infusion fluid line and the patient fluid removal rate $Q_{pfr}$, or a diffusive dose flow rate $D_{dial\_set}$, which is the prescribed mean value of the flow rate through the dialysis fluid line $Q_{dial}$. The control unit also receives the readings of the scales and thus knows the values $W_i$ of the initial weights of each container (step 301). Note that the volumes $V_i$ of each of the containers may be used as an alternative to the weights in below description of this first solution. Then the set value $Q_{iset}$ namely the flow rate to be set in each fluid line is calculated (step 302). Depending upon the set value $D_{set}$ which has been entered or received, the control unit is configured to calculate a reference time value $T_r$ in different ways, namely:

if $D_{dial\_set}$ is being set, $T_r$ is calculated by dividing the initial weight $W_i$ of the fresh dialysate container 20 by the dose flow rate $D_{dial\_set}$ of the line leading to the same container, or if $D_{conv\_set}$ is being set, $T_r$ is calculated by dividing the sum of the initial weights $W_i$ of the replacement fluid containers (depending upon the circuit structure those present among containers 16, 23, 26) by the dose flow rates of the lines $D_{conv\_set}$ leading to the same containers, or if $D_{eff\_set}$ is being set, $T_r$ is calculated by dividing the sum of the initial weights of the first, second, third, and fourth containers (depending upon the circuit structure those present among containers 16, 20, 23, 26) by the effluent dose flow rate $D_{eff\_set}$.

Once the reference time $T_r$ is calculated (step 303), the control unit is configured to determine the fluid flow rate in each one of the fresh fluid lines by dividing a weight $W_i$ of the respective container by the value of reference time $T_r$ (step 304). For the sake of simplicity, the description given above in connection with steps 303 and 304 was restricted to the simultaneous emptying of all the bags/containers being used (see also FIGS. 7A and 7B). In most cases this results in having all the pumps running at the same flow rate considering that all fluid bags have roughly the same initial weight.

Figure 8A:
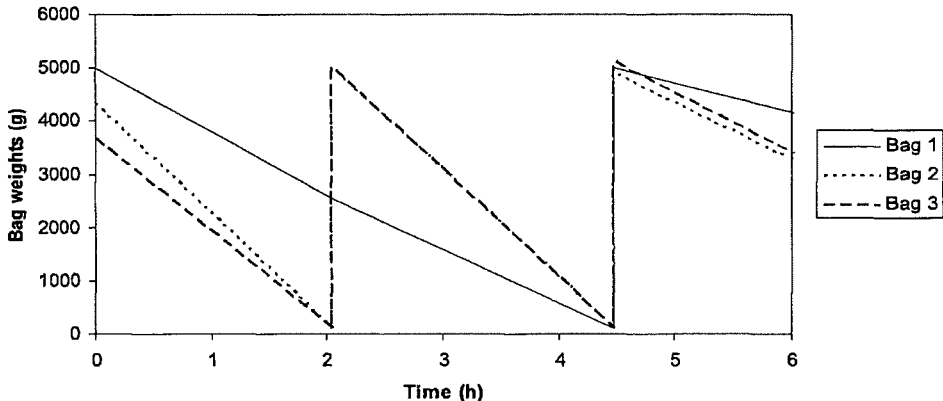
FIG. 8A shows a chart, relative to the emptying profiles of three bags/containers in accordance with the flowchart of FIG. 6, where the vertical axis represents the weight of each one of three bags/containers and the horizontal axis represents the emptying time.
Figure 8B:
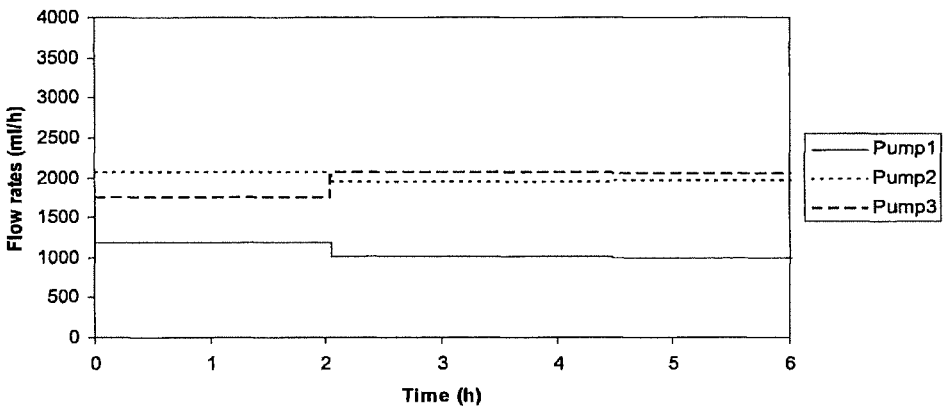
FIG. 8B shows a chart, relative to the set flow rates as a function of time for the three pumps withdrawing fluid from respective bags/containers in order obtain the emptying profiles shown in FIG. 8A.

To give more flexibility to the system, it is possible to attribute a weighting factor per pump/bag in such a manner that the emptying time of a given bag could be a multiple of the emptying time of one or more bags. FIGS. 8A and 8B show a second solution where the time required for emptying one of the bags is twice that required for the other 2 bags. Thus, in general and as shown in FIG. 6, it is possible associating a multiplying weighing coefficient $c_i$ to each weight $W_i$ of the respective container when calculating the value for $T_r$. Note that the volumes $V_i$ of each of the containers may be used as an alternative to the weights also for this second solution. Moreover, note $c_i$ is an integer: when all $c_i$ values are imposed to be equal to 1 then all containers empty at the same time, while if for instance, as in FIG. 8A, one of the $c_i$ values is imposed to be equal to 2 and the others equal to 1, then two bags empty twice as faster than the other. In general $c_i$ (normally equal to 1, 2, 3, or 4 or 5) may be used to customize the control by allowing the emptying times of the various bags to be one multiple of one the remaining bags. In this case $T_r$ would be calculated as follows:

$$T_r = (\Sigma W_i \cdot c_i)/\text{Dose}$$

$Q_{iset}$, namely the flow rate to be set in each fluid line, is then computed also taking the value of each coefficient $c_i$ into account as:

$$Q_{iset} = W_i/(T_r \cdot c_i)$$

Once the $Q_{iset}$ values are calculated, following one or the other of the above sequence of steps, they are stored in a memory (step 305) and then applied to control the pump speeds as described herein below in greater detail with reference to certain embodiments (step 307). In accordance with an optional aspect the control unit may issue a signal to the user interface 12 requesting a confirmation (306) from the user before actually applying the calculated values of $Q_{iset}$ to control the pumps.

Figure 9:
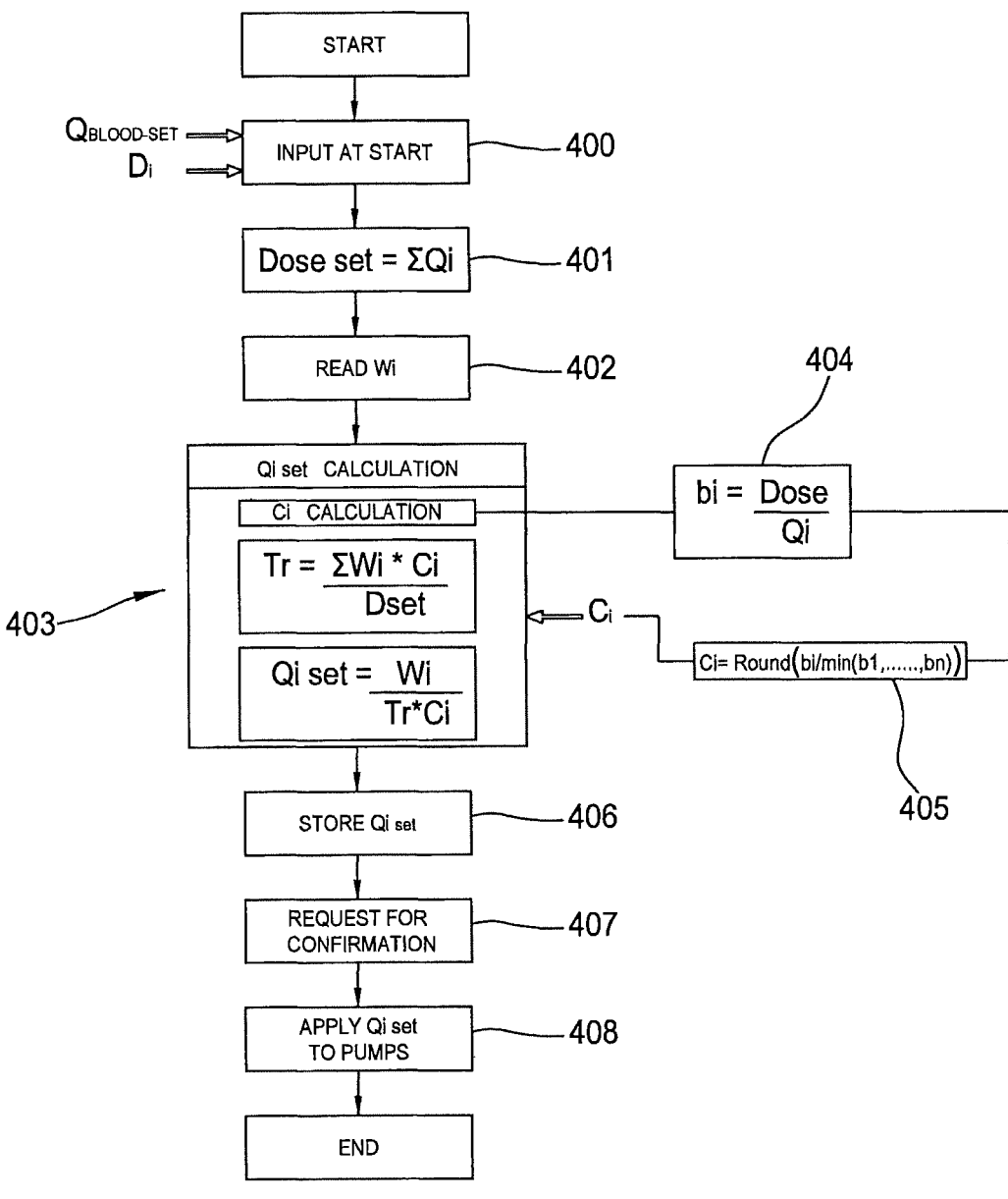
FIG. 9 represents a flowchart showing calculation of set flow rates in a medical apparatus, e.g. of the type of FIGS. 1-4, according to a further aspect of the invention.

In accordance with a third alternative solution, which is shown in the flowchart of FIG. 9, the control unit 10 may be configured to work in a situation where a number of proposed values $Q_i$ for the flow rates through each one of the lines are available. This may happen before start of the treatment or at a certain moment during the treatment. For instance the proposed $Q_i$ values could be values set by the user (step 400), or values calculated by the control unity to accomplish targets other than synchronization of the emptying of the fluid bags. The set value of the treatment dose $D_{set}$ to be delivered to the patient during the treatment may be either calculated by the control unit based on the flow rates $Q_i$ or set by the user and communicated by to the control unit (step 401). Alternatively, the set value of the dose may be received through an external channel or be pre-stored in a memory connected to the control unit. The blood pump flow rate may be set by the user (step 400) or calculated by the control unit (see below section "Blood pump setting"). The control unit also receives the readings of the scales and thus knows the values $W_i$ of the initial weights of each container (step 402). Note that the volumes $V_i$ of each of the containers may be used as an alternative to the weights also for this third solution. Then, the set value $Q_{iset}$ namely the flow rate to be set in each fluid line may be calculated by the control unit (step 403) dividing a weight $(W_i)$ of the respective container by the value of a reference time $(T_r)$ multiplied by a respective weighing coefficient $(c_i)$ for each respective container using formula:

$$Q_{iset} = (W_i/c_i)/T_r, \text{ where } T_r = (\Sigma W_i \cdot c_i)/\text{Dose}$$

On its turn, $c_i$ for each respective container may be calculated as a function of an intermediary factor $b_i$ obtained (see step 404) by dividing either the dose or the sum of said proposed values $Q_i$ of the flow rates by the respective proposed value $Q_i$. In the example of FIG. 9, each weighing coefficient $c_i$ for each respective container is calculated (step 405) using formula:

$c_i = \text{Round } [b_i/\text{min}(b_i \ldots b_n)]$, where "$\text{min}(b_i \ldots b_n)$" is a function selecting the minimum among the $b_i$ factors, and "Round" is a function determining the natural number nearest to the result of quotient $b_i/\text{min}(b_1 \ldots b_n)$.

Once the $Q_{iset}$ values are calculated, they may be stored in a memory (step 406) and then applied to control the pump speeds as described herein below in greater detail with reference to certain embodiments (step 408). In accordance with an optional aspect the control unit may issue a signal to the user interface 12 requesting a confirmation (407) from the user before actually applying the calculated values of $Q_{iset}$ to control the pumps.

As a further variant applicable to the above described three alternative solutions, the calculation of the reference time $T_r$ may be done as follows: the control unit may be configured to allow entry of the treatment time T, and calculate the reference time $T_r$ either as the treatment time T or as a sub-multiple of the treatment time T. As disclosed hereinbefore once $T_r$ has been calculated, each flow rate may be set as $Q_{iset} = W_i/T_r$, or as $Q_{iset} = W_i/(T_r \cdot c_i)$ where $c_i$ is an integer from e.g. 1 to 5. In another variant for the calculation of $T_r$, the control unit 10 may be configured to receive one set value set by an operator for one fluid flow rate through one of the lines present in the blood treatment apparatus. For instance, the operator may set the fluid flow rate $Q_{rep1}$ through the pre-dilution infusion fluid line 15, or the fluid flow rate $Q_{rep2}$ through the post-infusion fluid line 25, or the fluid flow rate $Q_{pbp}$ through the pre-blood pump infusion fluid line 21, a fluid flow rate $Q_{dial}$ through the dialysis liquid fluid line 27. The setting may be done through the user interface or via any other input. Once the input of a flow rate to a certain fluid line is set, the control unit is configured to identify the container associated to the fluid line for which the fluid flow rate has been set and to detect the respective initial weight. Then, the control unit may calculate the reference time $T_r$ dividing the initial weight $W_i$ of the identified container by the set value of the fluid flow rate set by the operator. Once $T_r$ has been calculated, each flow rate may be set as $W_i/T_r$ or as $Q_{iset} = W_i/(T_r \cdot c_i)$ where $c_i$ is an integer from e.g. 1 to 5.

In accordance with a fourth alternative solution, the control unit may be configured to execute a synchronization algorithm able to combine the use of proposed values for the set flow rates (for instance initially set by the user or calculated using one or more of the mathematical relations, as above described) with at least a certain degree of synchronization in the emptying of the containers; in other words, a purpose of the algorithm is to minimize the number of user interventions while keeping the flow rates in the 'neighborhood' of some initial settings (which may be manual or computed settings). In practice this algorithm is designed to change according to a certain set percentage the initially set or calculated flow rates in order to reduce as possible the number of container/bag changes across a certain time period, e.g. 24 hours, without substantially changing the initially set or calculated flow rates.

Figure 13:
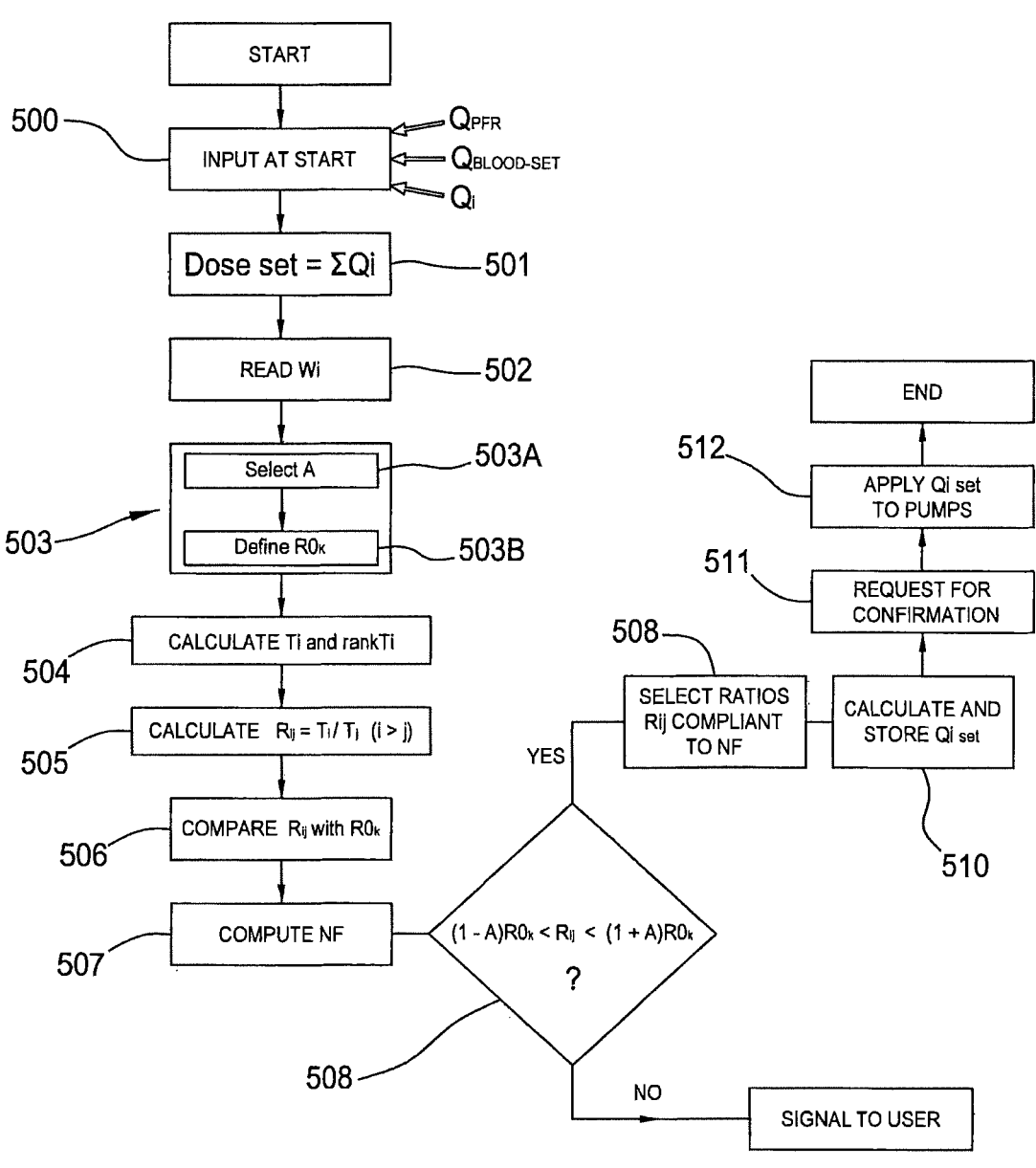
FIG. 13 is a flowchart showing calculation of set flow rates in a medical apparatus, e.g. of the type of FIGS. 1-4, according to another aspect of the invention.

The starting point of the algorithm (see FIG. 13) is the knowledge of:

the full set of proposed flow rates $Q_i$ (coming either from user settings or from a previous computation step—step 500);

the full set of bag/container weight or volume data $W_i$ or $V_i$ providing the initial weight or volume of each container (again either entered by the user or measured with appropriate sensors—step 502).

Also the blood flow rate setting for the blood pump may be entered or calculated by the control unit, see step 500.

At step 503, an allowed adjustment parameter 'A' is defined as maximum relative change allowed on bag/container change periods in order to optimize bag synchronization and reduce number of user interventions (step 503A). The algorithm also considers 'ratios of interest' $R0_k$ which are parameters defined in the algorithm as ratios between change periods (time between one container change and the next change of the same container) of pairs of containers (step 503B). Ratios of interest are defined for each pair of lines and respective containers. K is an integer which may vary from 1 to M, and M may be pre-stored in the control unit memory or the control unit may be configured to receive it from a user input. The algorithm takes into account that more interventions (container changes) are saved when identifying a '1 to 1' container synchronization ratio between two lines (because in that case the containers of the two lines are changed at the same time), than when having a '1 to 4' ratio.

Next table 1 provides the list of the optimum ratios of interest when considering all synchronization ratios up to 'order 5' in relation with a pair of containers indicated as bag1 and bag2. The first 8 $R0_k$ values are used in some examples reported at the end of the detailed description.

TABLE 1

| period ratios of interest ranked by 'efficiency' | | | | |
|---|---|---|---|---|
| k | Bag 1 | Bag 2 | Period ratio Ba1/Bag2 ($R0_k$) | % bag change saved |
| 1 | 1 | 1 | 1.00 | 50% |
| 2 | 1 | 2 | 2.00 | 33% |
| 3 | 1 | 3 | 3.00 | 25% |
| 4 | 1 | 4 | 4.00 | 20% |
| 5 | 2 | 3 | 1.50 | 20% |
| 6 | 1 | 5 | 5.00 | 17% |
| 7 | 3 | 4 | 1.33 | 14% |
| 8 | 2 | 5 | 2.50 | 14% |
| 9 | 3 | 5 | 1.67 | 13% |
| 10 | 4 | 5 | 1.25 | 11% |

In the above table referring for instance to the third more interesting ratio (corresponding to k=3), it is possible to see that k=3 matches with Bag1-Bag2=1 to 3, meaning that Bag2 is changed 3 times while Bag1 is changed once. This corresponds to a change bag period of Bag1 which is 3.0 times longer than the change bag period for Bag2: thus, one user intervention out of 4 is saved compared to a situation where no synchronization at all would be present. Indeed, with k=3 there would be 2 single bag changes of Bag2+1 simultaneous bag changes of Bags 1 and 2 with a total of 3 interventions, whilst in case of no synchronization there would be 3 single bag changes of Bag2+1 single bag change of Bag2, meaning a total of 4 interventions. As K increases the degree of synchronization goes down and, consequently, the number of bag or container changes saved also goes down.

Referring now to the general case of a treatment apparatus with N lines leading to respective N bags or containers, the control unit may be configured to execute the following steps, after the value of A has been selected or predefined (at step 503, see FIG. 13):

Step 504: calculate $T_i$ container change period $T_i=V_i/Q_i$ and rank each circuit according to the calculated container change period, where i=1 to N ($T_i$ increasing with i), Step 505: compute all period ratios $R_{ij}=T_i/T_j$, with i>j Step 506: compare each period ratio $R_{ij}$ to the preset list of ratios of interest $R0_k$, k=1 to M, Step 507: compute the number of degrees of freedom NF; this number if given by the sum of the number of lines less the number of constraints (see further below), Step 508: for each ratio $R_{ij}$ where a k value exists verify that $(1-A) \cdot R_0 k < R_{ij} < (1+A) \cdot R_0 k$, compute the number of daily saved container changes, Step 509: Select the NF ratios $R_{ij}$ providing the largest number of saved container changes; the selection of the 'best' $R_{ij}$ has to ensure the definition of NF independent relations between NF+1 variables (with the 'NF+1'$^{th}$ relation: $Q_{eff}=\Sigma Q_{iset}$), Step 510: Apply these ratios to compute the optimized flow rates, keeping $Q_{eff}=\Sigma Q_{iset}$ unchanged, and optionally store the calculated $Q_{iset}$, Step 511: optionally request for confirmation by a user of the calculated $Q_{iset}$, Step 512: apply the calculated values $Q_{iset}$ to control each one of the respective pumps.

Concerning the mentioned degrees of freedom NF (step 507 above), the following should be noted. In an apparatus having N lines (e.g. a number of infusion lines, a dialysate line, a line leading to a syringe and an effluent line), then the effluent line flow rate may verify condition $Q_{eff}=\Sigma Q_{iset}$; moreover the syringe line may have a fixed flow rate; the N−2 other lines are infusion or dialysate lines leading to respective containers having fixed volume. In the case where both effluent and syringe bag/container volumes are fixed, the associated bag change periods are also fixed and the N−2 bag change periods for the other lines remain to be defined. As these N−2 periods/flow rates are already linked by the relation $Q_{eff}=\Sigma Q_{iset}$, only NF=N−3 relations may be considered for defining all the flow rates. In the scenario where both effluent and syringe bag/container volumes are let free, then the number of degrees of freedom is NF=N−1, since effluent bag volume ($V_{eff}$) and syringe volume ($V_{syr}$) are two additional variables in the system.

In accordance with an aspect, the selection of the NF ratios $R_{ij}$ (step 509 above) providing for the highest number of saved bag changes considers also the 'degrees of freedom' issue. The selection of the 'best' $R_{ij}$ has to ensure the definition of NF independent relations between NF+1 variables (with the 'NF+1'th relation being $Q_{eff}=\Sigma Q_i$).

Note that irrespective of which one of the above described sequences of steps is used for the determination of $Q_{iset}$, once these set values $Q_{iset}$ have been calculated (e.g. using one or more mathematical relations and/or one or more optimization criteria), then the control unit 10 may be configured to display the calculated set values. As mentioned, the control unit may also be configured to ask, or wait, for a confirmation which may be entered by the user, e.g. through action onto the user interface 12. The control unit 10 is designed to control the means for regulating the flow rate based on the calculated set values either automatically (i.e. with no need of any action on the part of an operator), or after the appropriate confirmation is entered and a confirmation signal received at the control unit.

Figure 7A:
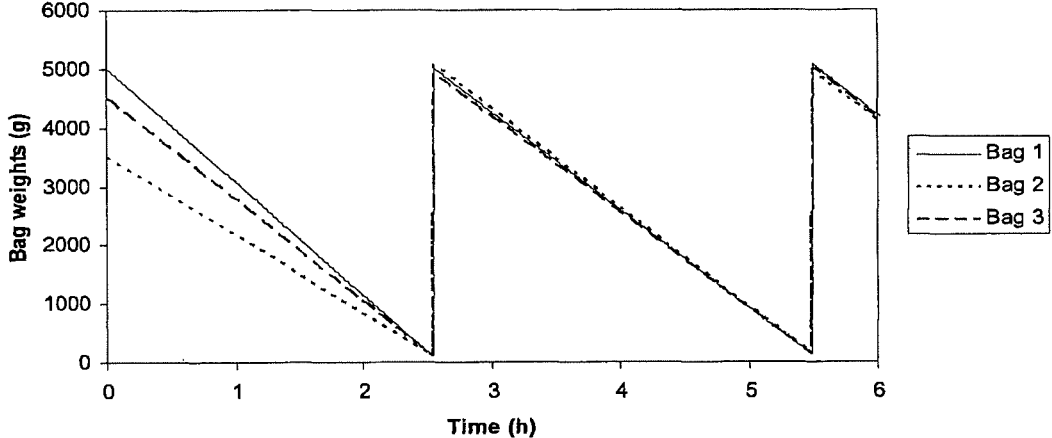
FIG. 7A shows a chart, relative to the emptying profiles of three bags/containers in accordance with the flowchart of FIG. 6, where the vertical axis represents the weight of each one of three bags/containers and the horizontal axis represents the emptying time; as it may be seen although the initial weight of each bag may be different, all bags/containers are emptied at the same time.
Figure 7B:
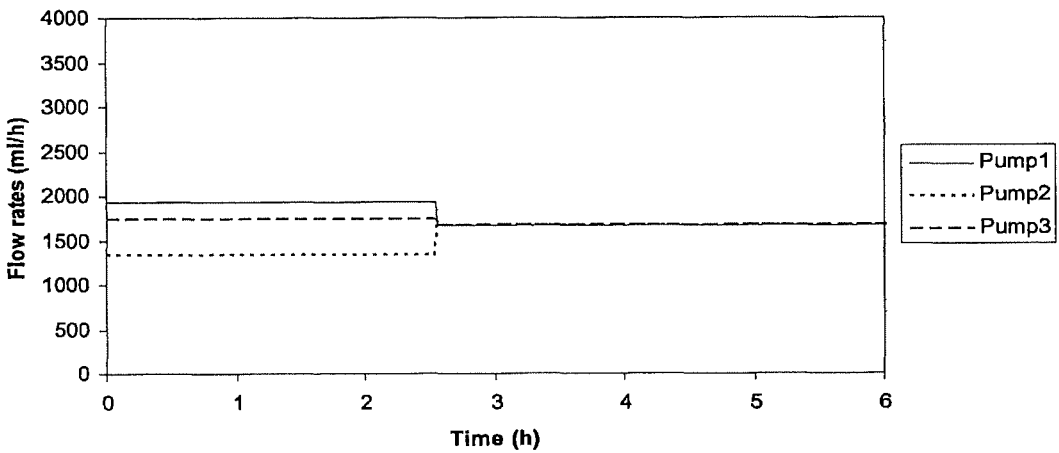
FIG. 7B shows a chart, relative to three set flow rates as function of time for three pumps withdrawing fluid from respective bags/containers in order obtain the emptying profiles shown in FIG. 7A.

The control unit 10 may also be configured store, e.g. in the memory 10a connected to the same control unit, the maximum volume of fluid which may be contained in each container of fresh fluid. The control unit may also be configured to store in a memory connected to the same control unit the maximum volume of fluid which may be contained in said waste container. The volume each container may host may be detected by a sensor associated to each respective container and connected to the control unit, or may be entered by an operator for each respective container through a user interface connected to the control unit, or determined by the control unit associating an identification code (indicia such as a bar code, an RFID or other identification means may be associated to the container) on each respective container to a respective volume, or said volume may be pre-stored in said memory. By knowing the volume of fluid that may be hosted in each container, the control unit may be configured to generate an alarm signal and/or to stop the treatment when the minimum quantity of fluid in one fresh fluid container (i.e. in one among the infusion fluid containers 16, 23, 26 and the dialysis fluid container 20) is reached, corresponding to a "empty container" threshold. In this situation, the user knows that he is supposed to substitute all fresh fluid containers (if the user selected the simultaneous emptying criteria and the emptying is simultaneous on all bags/containers as shown in FIGS. 7A, 7B) or to substitute a known number of the fresh fluid containers (if the user selected the simultaneous emptying criteria and the emptying of the bags or containers is synchronized to happen for two or more containers at prefixed intervals, as shown in FIG. 8A,8B). The control unit may also be configured to generate an alarm signal and/or to stop the treatment when the maximum quantity of fluid has been reached in the effluent fluid container (corresponding to a "full container" threshold). By treatment stop it is meant a condition where the control unit is configured to stop at least the pumps delivering fresh and spent fluid (namely pumps 18, 21, 24, 27, 17 in the embodiments of FIGS. 2 and 4; pumps 18, 21, 27, 17 in the embodiment of FIG. 1; pumps 21, 27, 17 or 21, 18, 17 in the embodiment of FIG. 3) and optionally also the blood pump 11.

In the embodiments of FIGS. 1-4 a respective scale (or other force sensor) is associated to the support of each container for detecting in real time the actual weight, and thus the current volume of fluid, of each container. In this manner the control unit, which is connected to the scales, may determine when the volume of fluid in each respective container is approaching or passing the respective thresholds (empty or full) as above described. Of course alternative sensors (e.g. level sensors) depending upon the circumstances and or the structure of the containers.

Blood Pump Setting

In the above description the it has been indicated that the blood pump may be controlled by the control unit 10 using a set value of the blood flow rate $Q_{BLOOD}$ entered by the user (step 200 in FIG. 5). More in general, the control unit 10 may allow entry by an operator of the set value for a blood flow $Q_{BLOOD}$ through the blood withdrawal or blood return line, or it may be configured to calculate the set value for the blood flow to be set. In this latter case the calculated value for the set blood flow could be calculated based on the value of the flow rate determined in one of the fluid lines: for instance the blood flow rate could be calculated to be proportional to calculated value of the flow rate through pre-blood pump infusion line (or vice versa the pre-blood pump infusion line flow rate could be calculated to be proportional to $Q_{BLOOD}$). Alternatively, the blood flow rate may be calculated based on a sensed value of a patient parameter or of a treatment parameter, e.g. by way of non-limiting examples: the pressure sensed by pressure sensor 6b in tract 6a of the blood withdrawal line, a measured blood recirculation fraction re-circulating from the blood return line 7 into the blood withdrawal line 6, a measured value of hemo-concentration measured in correspondence of one of the blood lines 6, 7, a measured value of transmembrane TMP pressure across the filter semipermeable membrane 5.

In any case, the control unit 10 may control the blood pump using either the entered or the calculated set value for the blood flow $Q_{BLOOD}$.

Safety Features

It should be noted that the control unit may be designed to include some safety features: for instance the filtration fraction is an important factor to be considered. Since the flow rates may automatically be set by the control unit 10, it is may be convenient to ensure that all pumps infusing in post-dilution do not cause an excessive filtration fraction (e.g. post-dilution flow rate >20% of blood flow rate). In this respect the control unit 10 may be configured to check if the calculated set value for the fluid flow through the post-dilution infusion line is higher than a prefixed fraction of the blood flow rate and in the affirmative activate a correction procedure. The correction procedure may comprise issuing a warning to the user interface, or it may comprise issuing a command to stop the treatment, or it may comprise correcting the delivery of fluid through one or more of the other lines, or (in case for instance the blood treatment apparatus includes a switch on the post-dilution line) issuing a command to switch 100 and/or 101 to temporary connecting a post-dilution fluid line to the blood withdrawal line. For instance referring to FIG. 4, the control unit could switch one or more lines infusing in post-dilution to pre-dilution or dialysate mode (acting on switch valves 100 and 101). The switch could be accompanied by an increase in the flow rate of the pump(s) that have been switched and by a reduction in the flow rates of the other pumps. For instance if line 15 was initially in post dilution configuration, said line may be switched to pre-dilution by acting on valve 100: the switched condition may be maintained until the weight of the container 16 decreases to a level making it possible to infuse in post-dilution without exceeding the maximum allowed filtration fraction. Alternatively, it is possible to have the control unit 10 configured to simply decrease the flow rate through one or more post-dilution lines to an extent sufficient to avoid problems in term of filtration fraction: in this case the emptying time for the concerned containers may be differed.

Composition of the Fluid Containers

All containers of fresh fluid may comprise a fluid (e.g. a replacement solution) having a same composition. The fact that the flow rates are not set individually implies that if the same type of composition is used during the treatment for containers there is no unexpected outcome regarding the electrolytic balance and/or acid-base equilibrium of the patient.

It may be envisaged that a container of fresh fluid comprises a fluid having a composition different from that of the other containers of fresh fluid: for instance the fourth container may contain an anticoagulant, such as a citrate solution; in this case the control unit 10 is configured to calculate the set value of fluid flow rate through the pre-blood pump infusion line to be proportional to the set or calculated value of the blood pump flow rate for achieving an adequate anticoagulation level. The other pump flow rates are adjusted so as to become follow the relations selected or the optimization criteria selected: for instance, if the optimization criteria of synchronous emptying time has been selected, the lines leading to the remaining bags/containers may be controlled such as these other containers empty at the same time as the citrate bag/container. Alternatively, the control unit could use the citrate bag/container in a way that it is not synchronized with the emptying of the other fluid bags/containers and is thus managed separately (e.g. flow rate is proportional to blood flow rate). In a further alternative, fourth bag/container emptying is synchronized with the other bags/containers and the blood pump flow rate setting is adjusted so as to be proportional to the citrate pump flow rate. Of course one could also envisage that all infusion bags/containers used be citrate-containing bags/containers: in this case synchronization may be made with no problems.

Example 1

Reference is made to an apparatus as shown in FIG. 3, provided with 3 fluid pumps (Dialysate pump 21, Replacement pump 27, Effluent pump 17) and thus capable of running a HDF therapy.

It is assumed that the following prescription is entered by the user via user interface 12:

Patient: BW (body weight)=80 kg blood flow rate: $Q_{BLOOD}$=200 ml/min patient fluid removal rate: $Q_{pfr}$=100 ml/h CRRT dose $D_{eff\text{-}set}$=35 ml/kg/h, where the dose is an 'effluent dose' per kg The following criteria are stored in memory 10a:

dialysate flow rate ($Q_{dial}$): 0 to 6000 ml/h replacement flow rate ($Q_{rep}$): 0 to 4000 ml/h no specific hemofilter/dialyzer related data

R1 optimization criteria as disclosed above for embodiments of FIGS. 1-4

The operator selects:

diffusion/convection ratio: R1=1.0 maximize filter life time

The control unit 10 then computes the flow rates as follows:

Effluent flow rate: $Q_{eff}$=35×80=2800 ml/h, $Q_{dial}$, $Q_{rep2}$ defined through the 2 below equations:

$$R_1 = Q_{dial}/(Q_{rep2}+Q_{pfr})=1.0$$

$$Q_{dial}+Q_{rep2}+Q_{pfr}=Q_{eff}=2800$$

Leading to $Q_{dial}$=1400 ml/h, $Q_{rep2}$=1300 ml/h

In order to maximize filter life time, replacement is set in PRE-dilution, rather than POST-dilution.

Example 2

Reference is made to an apparatus as shown in FIG. 1, provided with 4 fluid pumps (Dialysate pump 21, Replacement pump 27, Replacement pump 15, Effluent pump 17) and thus capable of running a HDF therapy.

Prescription:

Patient: BW=65 kg blood flow rate: $Q_{BLOOD}$=220 ml/min patient fluid removal rate: $Q_{pfr}$=100 ml/h CRRT dose $D_{eff\text{-}set}$=38 ml/kg/h, where the is defined as 'Urea dose'

The following criteria are stored in memory 10a:

dialysate flow rate ($Q_{dial}$): 0 to 6000 ml/h

PRE-replacement flow rate ($Q_{rep1}$): 0 to 4000 ml/h

POST-replacement flow rate ($Q_{rep2}$): 200 to 4000 ml/h no specific hemofilter/dialyzer related data The operator selects:

blood predilution ratio: $R_2$>0.10 minimize fluid consumption

The control unit 10 then computes the flow rates as follows:

$$Q_{eff}=Q_{dial}+Q_{rep1}+Q_{rep2}+Q_{pfr} \text{ to be minimized} \qquad \text{Eq.1:}$$

$$D_{set\text{-}urea}=Q_{BLOOD}/(Q_{BLOOD}+Q_{rep1})\times Q_{eff}=65\times \\ 38=2470 \text{ ml/h} \qquad \text{Eq.2:}$$

$$Q_{rep2}>200 \text{ ml/min} \qquad \text{Eq.3:}$$

$$R_2>0.10 \qquad \text{Eq.4:}$$

In order to meet the Urea dose target while minimizing fluid consumption ($Q_{eff}$), it is necessary to maximize the ratio $Q_{BLOOD}/(Q_{BLOOD}+Q_{rep1})$ According to the set constraints, this requires to set $Q_{rep1}$=0.10×$Q_{BLOOD}$=1320 ml/h (from eq. 4).

Equation 2 allows to define $Q_{eff}$=2470×(1+0.10/1)=2717 ml/h.

$Q_{dial}$ and $Q_{rep2}$ have then to be defined from:

$$Q_{dial}+Q_{rep2}=2717-100-1320=1297 \text{ ml/h} \qquad \text{Eq.1bis:}$$

$$Q_{rep2}>200 \text{ ml/h} \qquad \text{Eq.3:}$$

As no selected constraints allow fixing $Q_{dial}$ and $Q_{rep2}$ values among the multiple solutions of equations 1bis and 3, the control unit may be configured to:

offer intermediate values as default (typically $Q_{dial}$=700 ml/h and $Q_{rep2}$=600 ml/h in the example with rounding to the next ten of ml/h), or let the opportunity to the operator select to change this default within the computed range of solutions ($Q_{dial}$ from 0 to 1100 ml/h).

Example 3

Referring to FIG. 1 the equipment comprises three fresh fluid containers 16, 20, 26. The control unit may be configured to adopt the emptying profiles shown in FIG. 7A, thereby synchronizing the emptying of the three containers. At the beginning of the treatment, the scales inform the control unit about the quantity of fluid present in each bag. Then, an overall dose $D_{eff}$ of 5000 ml/h is received by the control unit and a first reference time Tri calculated as sum of the weights of the bags divided by the total dose: (5000+4500+3500) ml/5000 ml/h=2.6 h Each pump flow rate is then calculated as:

$$Q_{rep1}=5000/2.6=1923 \text{ ml/h}$$

$$Q_{dial}=4500/2.6=1730 \text{ ml/h}$$

$$Q_{rep2}=3500/2.6=1346 \text{ ml/h}$$

The above flow rates are then set as set values, and the respective pumps 18, 21 and 27 controlled accordingly by the control unit 10, as shown in FIG. 7B. After 2.6 hours all bags or containers 16, 20, 26 are simultaneously empty and the control unit is configured to stop the treatment and allow the containers to be substituted with new ones. In FIG. 7A it appears that the new containers have the same weight of 5000 ml and therefore the flow rate of each pump is set at the same flow rate of $5000/T_{r2}=1750$, as $T_{r2}$ is 3 hours

Example 4

Again referring to FIG. 1, the control unit may alternatively be configured to adopt the emptying profiles shown in FIG. 8A, thereby synchronizing the emptying of two of containers after a first interval and synchronizing the emptying of all three containers after a second interval. At the beginning of the treatment, the scales inform the control unit about the quantity of fluid present in each bag. Then, an overall dose $D_{eff}$ of 3000 ml/h is received by the control unit and a first reference time $T_r$ calculated as sum of the weights of the bags divided by the total dose:

$$T_r=(5000\cdot c_1+5000\cdot c_2+5000\cdot c_3)\text{ml}/3000\text{ ml/h}=4.17\text{ h}$$

where $c_1$, $c_2$ and $c_3$ are weighing factors in this case respectively set equal to 1, 1 and 2.
Each pump flow rate is then calculated as:

$$Q_{rep1}=5000/(4.17\cdot c_1)=1200\text{ ml/h}$$

$$Q_{dial}=5000/(4.17\cdot c_2)=1200\text{ ml/h}$$

$$Q_{rep2}=5000/(4.17\cdot c_3)=600\text{ ml/h}$$

The above flow rates are then imposed as set values and the respective pumps 18, 21 and 27 controlled accordingly by the control unit 10, as shown in FIG. 8B. After 4.17 hours two of the bags/containers 16, 20, 26 are simultaneously empty and the control unit is configured to stop the treatment and allow the two containers to be substituted with new ones. After about other 4.17 hours all three containers are empty and the control unit is configured to stop the treatment and allow the three containers to be substituted with new ones.

Example 5

Figure 10:
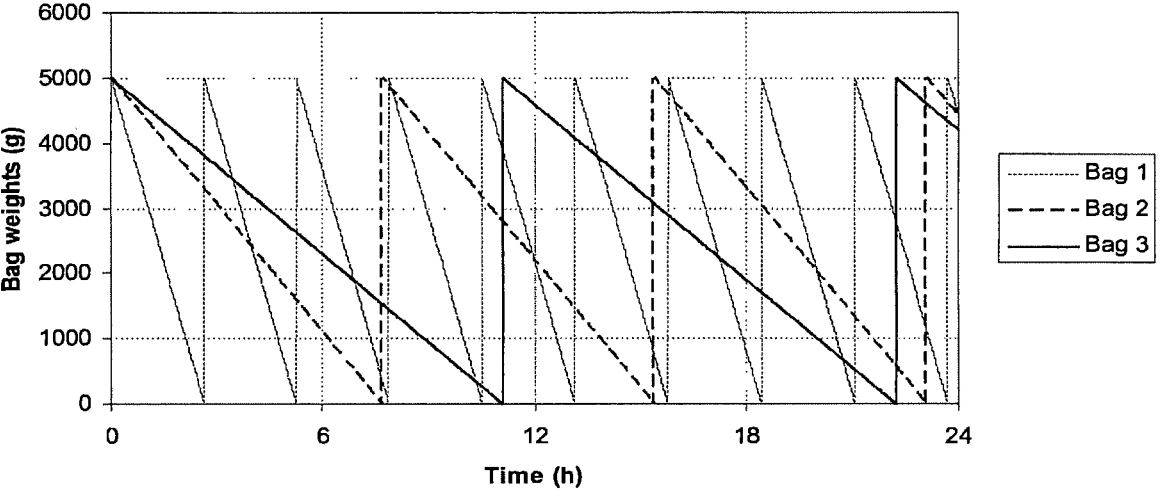
FIG. 10 shows a chart, relative to the emptying profiles of three bags/containers in a case where certain flow rates have been imposed for each one of the lines leading to the three bags/containers; the vertical axis in FIG. 10 represents the weight of each one of three bags/containers and the horizontal axis represents the emptying time.

Referring to the circuit of FIG. 1 and to the flowchart of FIG. 9, it may occur that proposed values $Q_i$ for the flow rates through each one of the 3 lines 15, 19 and 25 are available, e.g. after having been calculated by the control unity to accomplish certain ratios $R_1$, $R_2$, $R_3$. In this example the following proposed $Q_i$ values are given:
$Q_1$=1900 ml/h—proposed flow rate for $Q_{DIAL}$ through line 19
$Q_2$=650 ml/h—proposed flow rate for $Q_{REP1}$ through line 15
$Q_3$=450 ml/h—proposed flow rate for $Q_{REP2}$ through line 25
Each container 20, 16 and 26 is a 5 L bag, and the set dose is the sum of the above $Q_i$ values, namely 3000 ml/h.
In the case where no synchronization is implemented, then the situation would be as per FIG. 10, where 14 interventions for bag changes are required every 24 hours.
According to this example where the machine attempts to achieve a certain degree of synchronization without substantially changing the proposed flow rates, $c_1$, $c_2$ and $c_3$ are calculated as follows:
First the control unit calculates intermediary parameters Bi using the formula:

$$b_i=\text{Dose}/Q_i \text{ (where is the flow rate of the }i\text{th pump)}$$

The following results are obtained:

$$b_1=3000/1900=1.58$$

$$b_2=3000/650=4.62$$

$$b_3=3000/450=6.67$$

The value of $c_i$ are obtained by normalizing the values of bi with respect to their minimum and rounding the result to the closest natural number, using the formula:

$$c_i=\text{Round}(b_i/\min(b_1 \dots b_n))$$

With the following results:

$$c_1=\text{Round}(1.58/1.58)=1$$

$$c_2=\text{Round}(4.62/1.58)=3$$

$$c_3=\text{Round}(6.67/1.58)=4$$

From $c_1$, $c_2$ and $c_3$ the flow rate $Q_i$ of a given pump is calculated as follows:

$$T_r=(\Sigma W_i/c_i)/\text{Dose}$$

$$Q_i=(W_i/c_i)/T_r, \text{ where } W_i \text{ is the initial weight of the Bag}$$

$$T_r=(5000/1+5000/3+5000/4)/3000=2.6389\text{ h}$$

$$Q_{1set}=(5000/1)/2.6389=1895\text{ ml/h}$$

$$Q_{2set}=(5000/3)/2.6389=632\text{ ml/h}$$

$$Q_{3set}=(5000/4)/2.6389=474\text{ ml/h}$$

Figure 11:
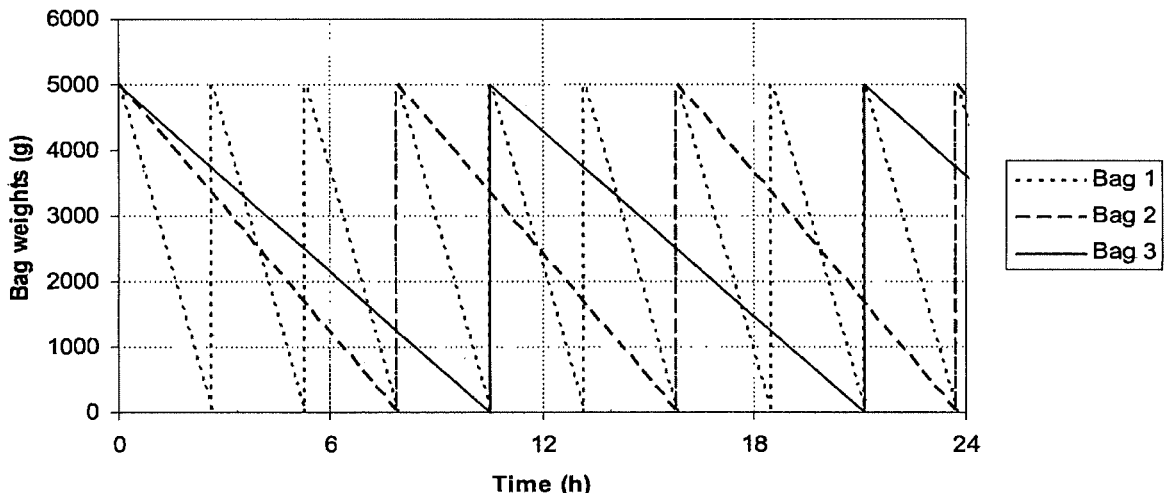
FIG. 11 shows a chart, relative to the emptying profiles of three bags/containers in accordance with the flowchart of FIG. 9, where the vertical axis represents the weight of each one of three bags/containers and the horizontal axis represents the emptying time.
Figure 12A:
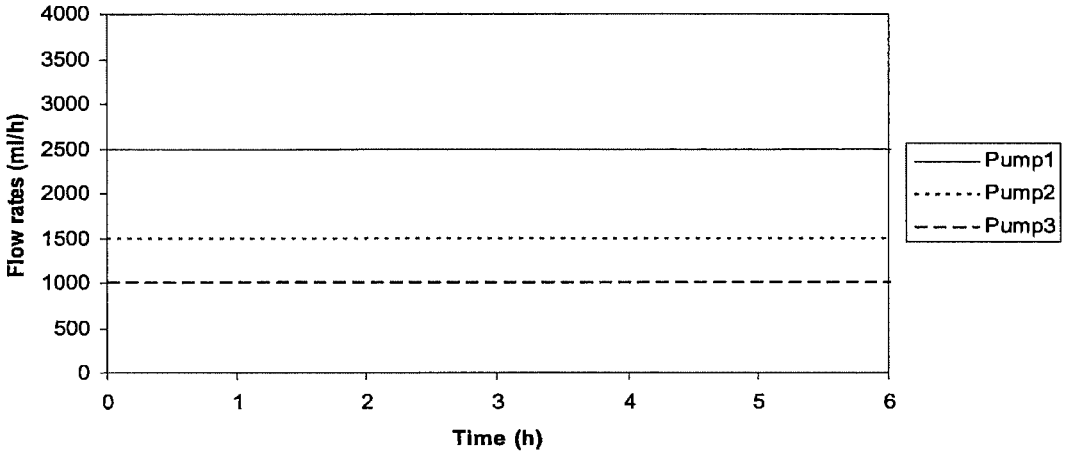
FIG. 12A shows a chart, relative to the emptying profiles of bags in accordance with a state of the art solution in a case where certain flow rates have been imposed for each one of the lines leading to the three bags/containers; also in FIG. 12A the vertical axis represents the weight of each one of three bags and the horizontal axis represents the emptying time.
Figure 12B:
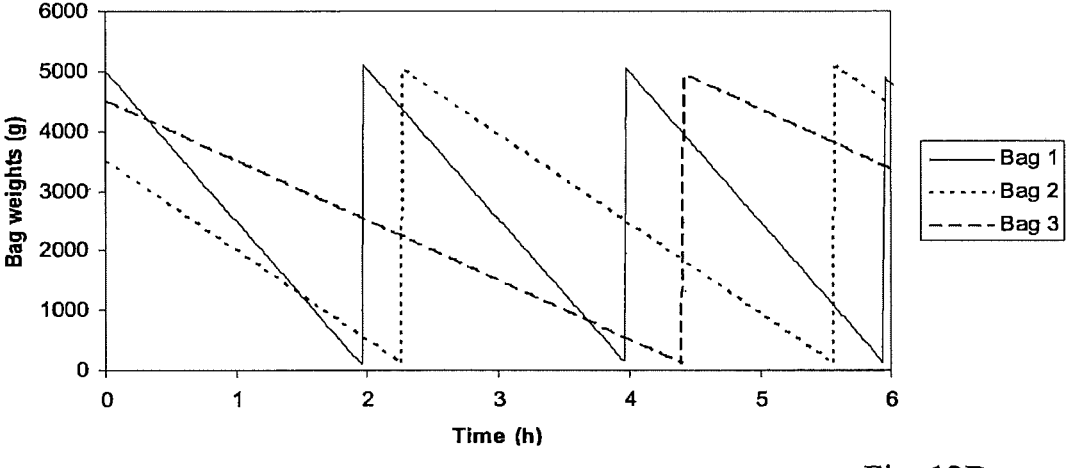
FIG. 12B shows a chart, relative to the set flow rates as a function of time for the three pumps withdrawing fluid from respective bags in order obtain the emptying profiles shown in FIG. 12A.

As shown in FIG. 11, the number of interventions for bag changes during 24 hours goes down to 9, while keeping the flow rates quite close to the initially proposed flow rates.

Example 6

The following is a general example according to the fourth synchronization solution described above which follows the general flowchart of FIG. 13.
$Q_{BLOOD}$ and the proposed $Q_i$ values are set by the user or calculated by the control unit at step 500. At this step, the patient fluid removal rate $Q_{PFR}$ is fixed or entered by the user at 100 ml/h. Then the dose value is set or calculated (step 501) and the volume of the of each bag detected or entered by the user (step 502).
The following parameters are selected or preprogrammed (step 503):
number ratios of interest 1 to 8 (M=8),
allowed flow rate adjustment of 10% (A=0.10) on the initially proposed $Q_i$.
It is assumed that the apparatus comprises a circuit similar to that of FIG. 2 with a syringe pump connected to the blood return line instead of infusion line 25. Effluent and Syringe bag/container volumes are fixed.
At step 504 the $T_i$ values are calculated and ranked by the control unit.
Table 2 below recaps the initial flow rates $Q_i$ ($2^{nd}$ column), the bag volumes ($3^{rd}$ column), the change bag periods $T_i$ ($4^{th}$ column) using the initial $Q_i$ values and the corresponding number of daily bag changes ($5^{th}$ column).

TABLE 2

| circuit | flow rate (initial) (ml/h) | bag volume (ml) | change bag period (h) | nb of daily bag changes (day$^{-1}$) |
|---|---|---|---|---|
| PBP | 1000 | 5000 | 5.00 | 4.80 |
| Dial | 1200 | 5000 | 4.17 | 5.76 |
| Rep | 350 | 3000 | 8.57 | 2.80 |
| syringe | 15 | 50 | 3.33 | 7.20 |

TABLE 2-continued

| circuit | flow rate (initial) (ml/h) | bag volume (ml) | change bag period (h) | nb of daily hag changes (day$^{-1}$) |
|---|---|---|---|---|
| PFR | 100 | — | — | — |
| Effluent | 2665 | 5000 | 1.88 | 12.79 |
| Total | | | | 33.35 |

Table 3 below ranks the change bag periods Ti from the shortest to the longest.

TABLE 3

| | Shortest period | | | | Longest period |
|---|---|---|---|---|---|
| | | Circuit index 'i' | | | |
| | 1 | 2 | 3 | 4 | 5 |
| Circuit ID | Effluent | syringe | Dial | PBP | Rep |
| Period (h) | 1.88 | 3.33 | 4.17 | 5.00 | 8.57 |
| nb daily bag changes (day$^{-1}$) | 12.79 | 7.20 | 5.76 | 4.80 | 2.80 |

At step 505, the $R_{ij}=T_i/T_j$ (i>j) are calculated by the control unit. Table 4 provides the computation of period ratios $R_{ij}=T_i/T_j$ (i>j)

TABLE 4

| i | j | | | | |
|---|---|---|---|---|---|
| | 1 | 2 | 3 | 4 | 5 |
| 1 | | | | | |
| 2 | 1.78 | | | | |
| 3 | 2.22 | 1.25 | | | |
| 4 | 2.67 | 1.50 | 1.20 | | |
| 5 | 4.57 | 2.57 | 2.06 | 1.71 | |

Then at step 506, the control unit compares the $R_{ij}$ ratios to the ratios of interests $R0_k$ of table 1 creating the ratios $R_{ij}/R0_k$. Table 5 shows the ratios $R_{ij}/R0_k$; At step 508 the control unit table 5 also checks the ratios $R_{ij}/R0_k$ which stay within the 'A' criterion, namely those which verify the condition:

$$(1-A)\cdot R0_k < R_{ij} < (1+A)\cdot R0_k.$$

Note that table 5 also includes an identification of ratios which result within 'A' criterion (see cells with underlined values, namely those which verify the condition: (1−A) $\cdot R0_k < R_{ij} < (1+A)\cdot R0_k$).

TABLE 5

| R0k | $R_{21}$ | $R_{31}$ | $R_{41}$ | $R_{51}$ | $R_{32}$ | $R_{42}$ | $R_{52}$ | $R_{43}$ | $R_{53}$ | $R_{54}$ |
|---|---|---|---|---|---|---|---|---|---|---|
| $R0_1$ | 1.78 | 2.22 | 2.67 | 4.57 | 1.25 | 1.50 | 2.57 | 1.20 | 2.06 | 1.71 |
| $R0_2$ | 0.89 | 1.11 | 1.33 | 2.28 | 0.63 | 0.75 | 1.29 | 0.60 | <u>1.03</u> | 0.86 |
| $R0_3$ | 0.59 | 0.74 | 0.89 | 1.52 | 0.42 | 0.50 | 0.86 | 0.40 | 0.69 | 0.57 |
| $R0_4$ | 0.44 | 0.56 | 0.67 | 1.14 | 0.31 | 0.38 | 0.64 | 0.30 | 0.51 | 0.43 |
| $R0_5$ | 1.18 | 1.48 | 1.78 | 3.05 | 0.83 | <u>1.00</u> | 1.71 | 0.80 | 1.37 | 1.14 |
| $R0_6$ | 0.36 | 0.44 | 0.53 | <u>0.91</u> | 0.25 | <u>0.30</u> | 0.51 | 0.24 | 0.41 | 0.34 |
| $R0_7$ | 1.33 | 1.67 | 2.00 | 3.43 | <u>0.94</u> | 1.13 | 1.93 | <u>0.90</u> | 1.54 | 1.29 |
| $R0_8$ | 0.71 | 0.89 | <u>1.07</u> | 1.83 | 0.50 | 0.60 | <u>1.03</u> | 0.48 | 0.82 | 0.69 |

At step 507 (this step may be executed at any time before step 509 below described), the control unit computes the degrees of freedom NF. Table 6 indicates the number of degrees of freedom (NF).

TABLE 6

| circuit | Flow rate | Bag volume | Deaees of freedom | NF |
|---|---|---|---|---|
| PBP | adjustable | fixed | Yes | NF = 3-1 = 2 |
| Dial | adjustable | fixed | Yes | |
| Rep | adjustable | fixed | Yes | |
| syringe | fixed | fixed | No | |
| Effluent | fixed | fixed | No | |

Then the control unit provides a computation of the number of bag change saved for all $R_{ij}$ within the above criterion for the A parameter and identifies the most effective combinations complying also with the available NF=2 degrees of freedom.

Table 7 shows this computation of the number of bag change saved and identifies (see arrow) of the NF=2 most effective combinations.

TABLE 7

| | i/j | Bag 1 | Bag 2 | nb daily bag changes | nb saved bag changes |
|---|---|---|---|---|---|
| ⟹ | 5/3 | 1 | 2 | 8.6 | 2.9 |
| | 4/2 | 2 | 3 | 12.0 | 2.4 |
| ⟹ | 5/1 | 1 | 5 | 15.6 | 2.6 |
| | 3/2 | 3 | 4 | 13.0 | 1.9 |
| | 4/3 | 3 | 4 | 10.6 | 1.5 |
| | 4/1 | 2 | 5 | 17.6 | 2.5 |
| | 5/2 | 2 | 5 | 10.0 | 1.4 |

Then the control unit calculates and optionally stores the flow rates

Table 8 provides a summary of selected $R_{ij}$ ratios and flow rate relations obtained using below Equations:

$$T_i = \frac{V_i}{Q_i}$$

$$R_{ij} = \frac{T_i}{T_j}$$

Flow rate relations derived from selected $R_{ij}$ and related $R0_k$ values:

$$Q_i = \frac{V_i}{V_j} \times \frac{Q_j}{R0_k}$$

TABLE 8

| $R_{ij}$ ID | Target $R0_k$ | $RO_k$ value | Flow rate relation* |
|---|---|---|---|
| $R_{53}$ | $RO_2$ | 2.00 | Q5 = 0.30 × Q3 |
| $R_{51}$ | $RO_6$ | 5.00 | Q5 = 0.12 × Q1 |

Then follows the computation of flow rates using $R_{ij}$ ratios selected in table 8. The adjusted flow rates are recapped in Table 9 below which clarifies how with a relatively small adjustment to the initially proposed flow rates a certain degree of synchronization in the container emptying has been achieved thus saving significant time in container changes.

TABLE 9

| circuit | flow rate (initial) (ml/h) | Adjusted flow rate (computed) | nb of daily bag changes day$^{-1}$ | Number of saved use rinterventions per day |
|---|---|---|---|---|
| PBP | 1000 | 1164 | 5.59 | |
| Dial | 1200 | 1066 | 5.12 | 2.56 |
| Rep | 350 | 320 | 2.56 | 2.56 |
| syringe | 15 | 15 | 7.20 | |
| PFR | 100 | 100 | — | |
| Effluent | 2665 | 2665 | 12.79 | |
| Total | | | 33.26 | 5.12 |
| Daily number of user interventions | | | 28.1 | |

Example 7

Reference is made to an apparatus as shown in FIG. 1, provided with 4 fluid pumps (Dialysate pump 21, Replacement pump 27, Replacement pump 15, Effluent pump 17) and thus capable of running a HDF therapy.
Prescription:
Patient: BW=65 kg
blood flow rate: $Q_{BLOOD}$=220 ml/min
patient fluid removal rate: $Q_{pfr}$=100 ml/h
CRRT dose $D_{eff-set}$=38 ml/kg/h, where the is defined as 'Urea dose'
The following criteria are stored in memory 10a:
dialysate flow rate ($Q_{dial}$): 0 to 6000 ml/h
PRE-replacement flow rate ($Q_{rep1}$): 0 to 4000 ml/h
POST-replacement flow rate ($Q_{rep2}$): 200 to 4000 ml/h
no specific hemofilter/dialyzer related data
The operator selects:
blood predilution ratio: $R_2$>0.10
minimize fluid consumption
The control unit 10 then computes the flow rates as follows:

$$Q_{eff}=Q_{dial}+Q_{rep1}+Q_{rep2}+Q_{pfr} \text{ to be minimized} \qquad \text{Eq.1:}$$

$$D_{set-urea}=Q_{BLOOD}/(Q_{BLOOD}+Q_{rep1})\times Q_{eff}=65\times 38=2470 \text{ ml/h} \qquad \text{Eq.2:}$$

$$Q_{rep2}>200 \text{ ml/min} \qquad \text{Eq.3:}$$

$$R_2>0.10 \qquad \text{Eq.4:}$$

In order to meet the Urea dose target while minimizing fluid consumption ($Q_{eff}$), it is necessary to maximize the ratio $Q_{BLOOD}/(Q_{BLOOD}+Q_{rep1})$
According to the set constraints, this requires to set $Q_{rep1}$=0.10×$Q_{BLOOD}$=1320 ml/h (from eq. 4).

Equation 2 allows to define $Q_{eff}$=2470×(1+0.10/1)=2717 ml/h.
$Q_{dial}$ and $Q_{rep2}$ have then to be defined from:

$$Q_{dial}+Q_{rep2}=2717-100-1320=1297 \text{ ml/h} \qquad \text{Eq. 1bis:}$$

$$Q_{rep2}>200 \text{ ml/h} \qquad \text{Eq.3:}$$

From the above first phase of computation, the following has been defined:
$Q_{eff}$=2717 ml/h,
$Q_{rep1}$=1320 ml/h,
a relation between $Q_{dial}$ and $Q_{rep2}$ ($Q_{dial}+Q_{rep2}$=1297 ml/h, directly derived from $Q_{eff}$=$\Sigma$Qi),
a condition on $Q_{rep2}$ (>200 ml/h).
In other words some flow rates are not completely defined. As above discussed in connection with the fourth solution of synchronization, a synchronization algorithm may be performed by the control unit from an arbitrary set of values; for example the above calculated flow rates where Qdial=550 ml/h (=>Qrep2=747 ml/h). The issue in this case is the choice of the 'allowed adjustment' parameter A, since a specific flow rate range is defined for Qdial [0;1297], allowing for a large range of bag change period. For this application case, the value of 'A' is selected at 0.3 (while 0.1 was used in example 6).

Qrep1, as well as Veff, are fixed; then number of degrees of freedom is NF=4−3=1 and consequently one single synchronization relation may be introduced. The initial input data to the synchronization algorithm are indicated in Table 10 while in Table 11 a ranking of change bag periods Ti is given.

TABLE 10

| circuit | flow rate (initial) (ml/h) | bag volume (ml) | change bag period (h) | nb of daily bag changes (day$^{-1}$) |
|---|---|---|---|---|
| Pre | 1320 | 5000 | 3.79 | 6.34 |
| Dial | 550 | 5000 | 9.09 | 2.64 |
| Post | 747 | 5000 | 6.69 | 3.59 |
| PFR | 100 | — | — | — |
| Effluent | 2717 | 5000 | 1.84 | 13.04 |
| Total | | | | 25.60 |

TABLE 11

| | Shortest period | | | Longest period |
|---|---|---|---|---|
| | | Circuit index 'i' | | |
| | 1 | 2 | 3 | 4 |
| Circuit ID | Effluent | Qpre | Qpost | Qdial |
| Period (h) | 1.84 | 3.79 | 6.69 | 9.09 |
| nb daily bag changes (day$^{-1}$) | 13.04 | 6.34 | 3.59 | 2.64 |

Then the control unit computes period ratios $R_{ij}=T_i/T_j$ (i>j). Table 12 recaps the computed values for $R_{ij}=T_i/T_j$.

TABLE 12

| | | | i | | |
|---|---|---|---|---|---|
| i | 1 | 2 | 3 | 4 |
| 1 | | | | |
| 2 | 2.06 | | | |
| 3 | 3.64 | 1.77 | | |
| 4 | 4.94 | 0.70 | 1.36 | |

Then the control unit compares the $R_{ij}$ ratios to the ratios of interests $R0_k$ of table 1 creating the ratios $R_{ij}/R0_k$ and also checks the ratios $R_{ij}/R0_k$ which stay within the 'A' criterion, namely those which verify the condition:

$(1-A)\cdot R0_k<R_{ij}<(1+A)\cdot R_0 k$. Below table 13 an identification of ratios which result within 'A' criterion (see cells with underlined values, namely those which verify the condition: $(1-A)\cdot R0_k<R_{ij}<(1+A)\cdot R0_k$).

TABLE 13

| R0k | $R_{21}$* | $R_{31}$** | $R_{41}$** | $R_{32}$** | $R_{42}$** | $R_{43}$*** |
|---|---|---|---|---|---|---|
| $R0_1$ | 2.06 | 3.64 | 4.94 | 1.77 | 0.70 | <u>1.36</u> |
| $R0_2$ | 1.03 | 1.82 | 2.47 | 0.88 | <u>0.35</u> | <u>0.68</u> |
| $R0_3$ | 0.69 | <u>1.21</u> | 1.65 | <u>0.59</u> | 0.23 | <u>0.45</u> |
| $R0_4$ | 0.51 | <u>0.91</u> | 1.24 | 0.44 | 0.17 | 0.34 |
| $R0_5$ | 1.37 | <u>2.42</u> | <u>3.29</u> | <u>1.18</u> | 0.46 | <u>0.91</u> |
| $R0_6$ | 0.41 | <u>0.73</u> | <u>0.99</u> | <u>0.35</u> | 0.14 | <u>0.27</u> |
| $R0_7$ | 1.54 | <u>2.73</u> | <u>3.71</u> | 1.33 | 0.52 | <u>1.02</u> |
| $R0_8$ | 0.82 | 1.45 | 1.98 | <u>0.71</u> | 0.28 | <u>0.54</u> |

*not considered as $Q_{eff}$ and $Q_{rep1}$ assumed already fixed
**selection with adjustment coefficient of 0.3 (ratio depending on $Q_{dial}$ or $Q_{rep2}$)
***selection with adjustment coefficient of 0.5 (ratio depending on $Q_{dial}$ and $Q_{rep2}$)

The number of degrees of freedom NF is then identified. Table 14 indicates the number of degrees of freedom (NF).

TABLE 14

| circuit | Flow rate | Bag volume | Degrees of freedom | NF |
|---|---|---|---|---|
| Pre | fixed | fixed | No | NF = 2-1 = 1 |
| Dial | adiustable | fixed | Yes | |
| Post | adjustable | fixed | Yes | |
| Effluent | fixed | fixed | No | |

Then the control unit identifies the best relation with NF=1 and respecting the limitations on the A value as well as the fixed parameters. Tables 15 and 16 indicate that the 'best' relation to introduce is $Q_{rep2}=Q_{eff}/3$, allowing to save more than 4 user interventions a day (~17%). Note that relation 2/1 (Qrep1–$Q_{eff}$) is discarded since both $Q_{eff}$ and $Q_{rep1}$ are fixed.

Relation 4/2 ($Q_{dial}$–$Q_{rep1}$) leads to $Q_{dial}=Q_{pre}$ which is not compatible with $Q_{eff}=\Sigma Q_i$

TABLE 15

| | i,j | Bag 1 | Bag 2 | nb daily bag changes | nb saved bag changes |
|---|---|---|---|---|---|
| | 4/2 | 1 | 1 | 9.0 | 4.49 |
| | 4/3 | 1 | 1 | 6.2 | 3.11 |
| | 2/1 | 1 | 2 | 12.4 | 6.46 |
| | 3/2 | 1 | 2 | 9.9 | 3.31 |
| | 4/3 | 1 | 2 | 6.2 | 2.08 |
| BEST ⟹ | 5/1 | 1 | 5 | 16.6 | 4.16 |
| | 3/1 | 1 | 4 | 16.0 | 3.33 |
| | 4/1 | 1 | 4 | 15.68 | 3.14 |
| | 3/2 | 2 | 3 | 9.92 | 1.98 |
| | 4/3 | 2 | 3 | 6.23 | 1.25 |

TABLE 16

| $R_{ij}$ ID | Target $R0_k$ | $R0_k$ value | Flow rate relation* |
|---|---|---|---|
| $R_{31}$ | $R0_3$ | 3.00 | Q3 = 0.333 × Q1 |

The above selected $R_{ij}$ ratios and flow rate relations (table 16) are used by the control unit for computation of flow rates $Q_{iset}$ (in this case $Q_3$ and $Q_1$ respectively corresponding to $Q_{rep2}$=391.3 ml/h and $Q_{dial}$=905.7 ml/h) as per below table 17.

TABLE 17

| circuit | flow rate (initial) (ml/h) | Adjusted flow rate (computed) | nb of daily bag changes day$^{-1}$ | Number of saved user interventions per day |
|---|---|---|---|---|
| Pre | 1320 | 1320 | 6.34 | |
| Dial | 550 | 905.7 | 4.35 | 4.35 |
| Post | 747 | 391.3 | 1.88 | |
| PFR | 100 | 100 | — | |
| Effluent | 2717 | 2717 | 13.04 | |
| Total | | | 25.60 | 4.35 |
| Daily number of user interventions | | | 21.3 | |

To secure the result, the algorithm might be repeated using a different set of initial flow rates; in this case it is verified that the same result is obtained with $Q_{dial}$=100 ml/h (=>$Q_{rep2}$=1197) as initial flow rate (same result except permutation of $Q_{rep2}$ and $Q_{dial}$ values).

Note that in the above example, in the case adjustment of Qrep1 is allowed, then NF=2 and 6.5 additional user interventions may be saved by setting $Q_{rep1}=Q_{eff}/2$ (computation steps not reported).

One positive aspect of the present invention is a simplification in setting of treatment prescription.

Moreover, the setting is more intuitive for the medical personnel.

In accordance with certain aspects, frequency of bag/container changes is reduced, with a positive impact on the treatment since lesser interruptions help in providing more continuous and accurate treatment.

Here below the components and corresponding reference numerals used in the detailed description are listed.

| Part | Reference numeral |
|---|---|
| extracorporeal blood treatment apparatus | 1 |
| filtration unit | 2 |
| primary chamber | 3 |
| secondary chamber | 4 |
| semi-permeable membrane | 5 |
| blood withdrawal line | 6 |
| blood return line | 7 |
| tract | 6a |
| bubble trap | 8 |
| bubble sensor | 8a |
| clamp | 9 |
| control unit | 10 |
| blood pump | 11 |
| user interface | 12 |
| an effluent fluid line | 13 |
| an effluent fluid container | 14 |
| pre-dilution fluid line | 15 |
| infusion fluid containers | 16, 23, 26 |
| dialysis fluid line | 19 |
| dialysis fluid container | 20 |
| dialysis pump | 21 |
| a post-dilution fluid line | 25 |
| effluent fluid pump | 17 |
| infusion pumps | 18, 27 |
| pre-blood pump infusion line | 22 |
| pump on pre-blood pump infusion line | 24 |
| line switches | 100, 101 |

The invention is claimed as follows:

1. An apparatus for extracorporeal treatment of blood comprising:

a filtration unit including a primary chamber and a secondary chamber separated by a semi-permeable membrane;

a blood withdrawal line in fluid communication with an inlet of the primary chamber, and a blood return line in fluid communication with an outlet of the primary chamber, said blood lines configured for connection to a patient cardiovascular system;

a blood pump configured to control a flow of blood through the blood lines;

an effluent fluid line in fluid communication with an outlet of the secondary chamber;

a dialysis fluid line in fluid communication at one end thereof with an inlet of the secondary chamber;

a pre-blood pump infusion line in fluid communication at one end thereof with the blood withdrawal line in a region of the blood withdrawal line positioned upstream of the blood pump;

a post-dilution infusion fluid line in fluid communication at one end thereof with the blood return line;

a container in fluid communication with an end of said pre-blood pump infusion line;

fluid flow regulators for regulating flow through said fluid lines comprising at least a dialysis fluid pump for regulating flow through said dialysis fluid line, at least a pre-blood infusion pump for regulating flow through said pre-blood pump infusion line, and an effluent fluid pump for regulating flow through said effluent fluid line;

a user interface for receiving entries from an operator; and a control unit operably connected to the user interface and the fluid flow regulators, the control unit configured to:

receive, as a first entry via the user interface, a set value for a blood flow ($Q_{BLOOD}$) through the blood withdrawal or blood return line, receive, as a second entry via the user interface, a set value for a fluid removal rate ($Q_{pfr}$) from the patient, receive, as a third entry via the user interface, a set value for a prescribed dose ($D_{set}$) to be delivered, wherein the prescribed dose ($D_{set}$) is a diffusive dose ($D_{dial}$) with a flow rate ($Q_{dial}$) of fluid supplied to the filtration unit secondary chamber through the dialysis fluid line, calculate set values of a second flow rate and a third flow rate based on said set value for the fluid removal rate ($Q_{pfr}$) from the patient set by the operator and on said prescribed dose value ($D_{set}$), wherein calculating the set values of the second flow rate and the third flow rate comprises:

calculating a fluid flow rate ($Q_{eff}$) through the effluent fluid line based on said set value for the fluid removal rate ($Q_{pfr}$) from the patient set by the operator and said prescribed dose value ($D_{set}$) set by the operator, and calculating a fluid flow rate ($Q_{rep2}$) through the post-dilution infusion fluid line, receive (i) a concentration ($C_{citrate}$) of an anticoagulant present in the container in fluid communication with the end of said pre-blood pump infusion line, and (ii) a prescribed dose for said anticoagulant ($D_{set-citrate}$) to be delivered to the patient during the extracorporeal treatment, calculate a set value for a fluid flow rate ($Q_{pbp}$) through said pre-blood pump infusion line as a function of:

the set value of blood flow rate ($Q_{BLOOD}$), the concentration ($C_{citrate}$) of the anticoagulant present in the container in fluid communication with the end of said pre-blood pump infusion line, and the prescribed dose for said anticoagulant ($D_{set-citrate}$) to be delivered through said pre-blood pump infusion line, and after calculating the fluid flow rate ($Q_{pbp}$) through said pre-blood pump infusion line, calculate the fluid flow rate ($Q_{eff}$) through the effluent fluid line as sum of the fluid flow rate ($Q_{rep2}$) through the post-dilution infusion fluid line, the fluid removal rate ($Q_{pfr}$) from the patient, the flow rate ($Q_{dial}$) of fluid supplied to the filtration unit secondary chamber through the dialysis fluid line, and the fluid flow rate ($Q_{pbp}$) through said pre-blood pump infusion line, wherein the control unit is further configured to control the blood pump, the dialysis fluid pump, the pre-blood infusion pump, the effluent fluid pump, and a post-dilution pump based on the set value of the blood flow rate ($Q_{BLOOD}$), the flow rate ($Q_{dial}$) of fluid supplied to the filtration unit secondary chamber through the dialysis fluid line, the fluid flow rate ($Q_{pbp}$) through the pre-blood pump infusion line, the fluid flow rate ($Q_{eff}$) through the effluent fluid line, and the fluid flow rate ($Q_{rep2}$) through the post-dilution infusion fluid line, respectively.

2. The apparatus of claim 1, further comprising a memory storing a plurality of mathematical relations correlating fluid flow rates selected in said group, said control unit being connected to said memory, and wherein the control unit is further configured to calculate the set values of at least the second and third fluid flow rates using said prescribed dose value ($D_{set}$) and the set value of the first fluid flow rate with said mathematical relations.

3. The apparatus of claim 1, wherein the apparatus includes a waste container in fluid communication with an end of the effluent fluid line and at least one further container of fresh fluid in fluid communication with an end of the dialysis fluid line.

4. The apparatus of claim 3, wherein the control unit is configured to store, in a memory connected to the control unit, a volume or weight of fluid that is contained in each container of fresh fluid and in the waste container, said volume or weight of fluid being detected by a sensor associated with each respective container and connected to the control unit, said sensors being in operable communication with the control unit and sending to the control unit corresponding weight signals.

5. The apparatus of claim 3, wherein the control unit is configured to:

assign to each container a reference volume or a reference weight which, when reached by the respective container, triggers a container change signal;

compare a measured volume or weight of each container to the respective assigned reference volume or assigned reference weight to trigger a container change signal when one of the containers reaches the respective assigned reference volume or assigned reference weight; and impose on one or more of the containers of fresh fluid a reference volume or reference weight which is different from zero and/or on the waste container a reference volume or weight that is less than a maximum volume or weight of the waste container.

6. The apparatus of claim 3, which comprises a separate scale detecting a weight of each respective container, wherein the control unit is configured to compare the detected weight of each container of fresh fluid to a respective threshold and to determine that at least one of the fresh fluid containers is empty if the detected weight is below the respective threshold and/or the control unit is configured to compare the detected weight of the waste fluid container to a respective threshold and to determine that the waste container is full if the detected weight is above the threshold, the control unit further configured to generate an empty container signal when the weight of one or more containers of fresh fluid is below the respective threshold and to generate a full container signal when the weight of said waste container is above the respective threshold.

7. The apparatus of claim 1, wherein the control unit is further configured to receive, by allowing a corresponding selection by an operator, at least one set value designating a treatment time.

8. The apparatus of claim 1, wherein the control unit is configured to identify at least one container associated with at least one of (i) the set value for the fluid flow rate ($Q_{rep2}$) through the post-dilution infusion fluid line, (ii) the set value for the flow rate ($Q_{dial}$) of fluid supplied to the filtration unit secondary chamber through the dialysis fluid line, (iii) a set value for a fluid flow rate ($Q_{rep1}$) through a pre-dilution infusion fluid line, and calculate a reference time by dividing an initial weight or volume of the identified at least one container by the at least respective set flow rate value.

9. The apparatus of claim 1, wherein the control unit is configured to calculate the set value of fluid flow rate ($Q_{pbp}$) through the pre-blood pump infusion line based on a pre-defined algorithm, the flow rate ($Q_{pbp}$) through the pre-blood pump infusion line being proportional to the set value of the blood pump flow rate ($Q_{BLOOD}$).

10. The apparatus of claim 1, comprising a second container leading to said post-dilution infusion fluid line, wherein the container in fluid communication with said pre-blood pump infusion line includes a regional anticoagulant, including a citrate based solution, the second container leading to said post-dilution infusion fluid line including an ionic balance solution, including a calcium ion based solution, the control unit configured to calculate the fluid flow rate ($Q_{pbp}$; $Q_{rep2}$) through said pre-blood pump infusion fluid line and through said post-dilution infusion fluid line based on at least one pre-defined algorithm.

11. The apparatus of claim 1, which includes a syringe line connected at one end thereof to the blood withdrawal line, the blood return line, or directly to the patient, the syringe line leading to a syringe container including an ionic balance solution, the control unit configured to calculate the fluid flow rate through said syringe line based on a pre-defined algorithm.

12. The apparatus of claim 1, wherein the pre-blood infusion pump is a peristaltic pump, controlled by the control unit, the peristaltic pump acting on a segment of the pre-blood pump infusion line to regulate the pre-blood pump infusion rate ($Q_{pbp}$).

13. The apparatus of claim 1, wherein a memory is provided storing a plurality of mathematical relations correlating fluid flow rates selected in a group of flow rates, said control unit being operably connected to said memory, wherein said mathematical relations stored in said memory comprise a convection-diffusion relation, relating a total fluid flow rate ($Q_{rep2}+Q_{pbp}$) through said infusion fluid lines with the fluid flow rate through said dialysis fluid line ($Q_{dial}$).

14. The apparatus of claim 1, wherein the blood pump is active in correspondence of a segment of the blood withdrawal line and the apparatus comprises the post-dilution infusion fluid line connected to the blood return line, wherein the control unit is configured to calculate the set value for the fluid flow rate through the post-dilution infusion fluid line, which is not set by the operator based on a group of flow rates and on said prescribed dose value ($D_{set}$).

15. An apparatus for extracorporeal treatment of blood comprising:

a filtration unit including a primary chamber and a secondary chamber separated by a semi-permeable membrane;

a blood withdrawal line in fluid communication with an inlet of the primary chamber, and a blood return line in fluid communication with an outlet of the primary chamber, said blood lines configured for connection to a patient cardiovascular system;

a blood pump configured to control a flow of blood through the blood lines;

an effluent fluid line in fluid communication with an outlet of the secondary chamber;

a waste container in fluid communication with an end of the effluent fluid line;

a dialysis fluid line in fluid communication at one end thereof with an inlet of the secondary chamber;

a first container of fresh fluid in fluid communication with an end of the dialysis fluid line;

a pre-blood pump infusion line in fluid communication at one end thereof with the blood withdrawal line in a region of the blood withdrawal line positioned upstream of the blood pump;

a second container in fluid communication with an end of said pre-blood pump infusion line and including a citrate based solution;

a post-dilution infusion fluid line in fluid communication at one end thereof with the blood return line;

a syringe container leading to said post-dilution infusion fluid line and including an ionic balance solution including a calcium ion based solution;

fluid flow regulators for regulating flow through said fluid lines comprising a dialysis fluid pump for regulating flow through said dialysis fluid line, a pre-blood infusion pump for regulating flow through said pre-blood pump infusion line, a syringe pump operable with the syringe container, and an effluent fluid pump for regulating flow through said effluent fluid line;

a user interface for receiving entries from an operator; and a control unit operably connected to the user interface and the fluid flow regulators, the control unit configured to:

receive, as a first entry via the user interface, a set value for a blood flow ($Q_{BLOOD}$) through the blood withdrawal or blood return line, receive, as a second entry via the user interface, a set value for a fluid removal rate ($Q_{pfr}$) from the patient, receive, as a third entry via the user interface, a set value for a prescribed dose ($D_{set}$) to be delivered, wherein the prescribed dose ($D_{set}$) is a diffusive dose ($D_{dial}$) with a flow rate ($Q_{dial}$) of fluid supplied to the filtration unit secondary chamber through the dialysis fluid line, calculate set values of a second flow rate and a third flow rate based on said set value for the fluid removal rate ($Q_{pfr}$) from the patient set by the operator and on said prescribed dose value ($D_{set}$), wherein calculating the set values of the second flow rate and the third flow rate comprises:

calculating a fluid flow rate ($Q_{eff}$) through the effluent fluid line based on said set value for the fluid removal rate $(Q_{pfr})$ from the patient set by the operator and said prescribed dose value $(D_{set})$ set by the operator, and calculating a fluid flow rate $(Q_{rep2})$ through the post-dilution infusion fluid line, receive (i) a concentration $(C_{citrate})$ of the citrate based solution present in the second container, and (ii) a prescribed dose for said citrate based solution $(D_{set\text{-}citrate})$ to be delivered to the patient during the extracorporeal treatment, calculate a set value for a fluid flow rate $(Q_{pbp})$ through said pre-blood pump infusion line as a function of:

the set value of blood flow rate $(Q_{BLOOD})$, the concentration $(C_{citrate})$ of the citrate based solution present in the second container, and the prescribed dose for said citrate based solution $(D_{set\text{-}citrate})$ to be delivered through said pre-blood pump infusion line, and after calculating the fluid flow rate $(Q_{pbp})$ through said pre-blood pump infusion line, calculate the fluid flow rate $(Q_{eff})$ through the effluent fluid line as sum of the fluid flow rate $(Q_{rep2})$ through the post-dilution infusion fluid line, the fluid removal rate $(Q_{pfr})$ from the patient, the flow rate $(Q_{dial})$ of fluid supplied to the filtration unit secondary chamber through the dialysis fluid line, and the fluid flow rate $(Q_{pbp})$ through said pre-blood pump infusion line, wherein the control unit is further configured to control the blood pump, the dialysis fluid pump, the pre-blood infusion pump, and the effluent fluid pump based on the set value of the blood flow rate $(Q_{BLOOD})$, the flow rate $(Q_{dial})$ of fluid supplied to the filtration unit secondary chamber through the dialysis fluid line, the fluid flow rate $(Q_{pbp})$ through said pre-blood pump infusion line, and the fluid flow rate $(Q_{eff})$ through the effluent fluid line, respectively.

16. An apparatus for extracorporeal treatment of blood comprising:

a filtration unit including a primary chamber and a secondary chamber separated by a semi-permeable membrane;

a blood withdrawal line in fluid communication with an inlet of the primary chamber, and a blood return line in fluid communication with an outlet of the primary chamber, said blood lines configured for connection to a patient cardiovascular system;

a blood pump configured to control a flow of blood through the blood lines;

an effluent fluid line in fluid communication with an outlet of the secondary chamber;

a dialysis fluid line in fluid communication at one end thereof with an inlet of the secondary chamber;

a pre-blood pump infusion line in fluid communication at one end thereof with the blood withdrawal line in a region of the blood withdrawal line positioned upstream of the blood pump;

a first container in fluid communication with an end of said pre-blood pump infusion line and including an anticoagulant;

a post-dilution infusion fluid line in fluid communication at one end thereof with the blood return line;

a second container leading to said post-dilution infusion fluid line and including an ionic balance solution;

fluid flow regulators for regulating flow through said fluid lines comprising at least a dialysis fluid pump for regulating flow through said dialysis fluid line, at least a pre-blood infusion pump for regulating flow through said pre-blood pump infusion line, and an effluent fluid pump for regulating flow through said effluent fluid line;

a user interface for receiving entries from an operator; and a control unit operably connected to the user interface and the fluid flow regulators, the control unit configured to:

receive, as a first entry via the user interface, a set value for a blood flow $(Q_{BLOOD})$ through the blood withdrawal or blood return line, receive, as a second entry via the user interface, a set value for a fluid removal rate $(Q_{pfr})$ from the patient, receive, as a third entry via the user interface, a set value for a prescribed dose $(D_{set})$ to be delivered, wherein the prescribed dose $(D_{set})$ is a prescribed dose $(D_{set\text{-}citrate})$ for said anticoagulant to be delivered through said pre-blood pump infusion line during the extracorporeal treatment, calculate set values of a second flow rate and a third flow rate based on said set value for the fluid removal rate $(Q_{pfr})$ from the patient set by the operator and on said prescribed dose value $(D_{set})$, the control unit configured to calculate the fluid flow rate $(Q_{pbp}; Q_{rep2})$ through said pre-blood pump infusion fluid line and through said post-dilution infusion fluid line based on pre-defined algorithms, wherein calculating the set values of the second flow rate and the third flow rate comprises:

calculating a fluid flow rate $(Q_{eff})$ through the effluent fluid line based on said set value for the fluid removal rate $(Q_{pfr})$ from the patient set by the operator and said prescribed dose value $(D_{set})$ set by the operator, and calculating a fluid flow rate $(Q_{rep2})$ through the post-dilution infusion fluid line, wherein the pre-defined algorithm for the fluid flow rate $(Q_{pbp})$ through said pre-blood pump infusion line is a function of:

the set value of flow rate of blood or of plasma $(Q_{BLOOD}; Q_{PLASMA})$, a concentration $(C_{citrate})$ of said anticoagulant present in the first container, and the prescribed dose for said anticoagulant $(D_{set\text{-}citrate})$ to be delivered through said pre-blood pump infusion line, and after calculating the fluid flow rate $(Q_{pbp})$ through said pre-blood pump infusion line, calculate the fluid flow rate $(Q_{eff})$ through the effluent fluid line as sum of the fluid flow rate $(Q_{rep2})$ through the post-dilution infusion fluid line, the fluid removal rate $(Q_{pfr})$ from the patient, the flow rate $(Q_{dial})$ of fluid supplied to the filtration unit secondary chamber through the dialysis fluid line, and the fluid flow rate $(Q_{pbp})$ through said pre-blood pump infusion line, wherein the control unit is further configured to control the blood pump, the dialysis fluid pump, the pre-blood infusion pump, and the effluent fluid pump based on the set value of the blood flow rate $(Q_{BLOOD})$, the flow rate $(Q_{dial})$ of fluid supplied to the filtration unit secondary chamber thorough the dialysis fluid line, the fluid flow rate $(Q_{pbp})$ through said pre-blood pump infusion line, and the fluid flow rate $(Q_{eff})$ through the effluent fluid line, respectively.

17. The apparatus of claim 16, further comprising a memory storing a plurality of mathematical relations correlating fluid flow rates selected in said group, said control unit being connected to said memory, and wherein the control unit is further configured to calculate the set values of at least the second and third fluid flow rates using said prescribed dose value ($D_{set}$) and the set value of the first fluid flow rate with said mathematical relations.

18. The apparatus of claim 16, which includes a waste container in fluid communication with an end of the effluent fluid line and an additional at least one container of fresh fluid in fluid communication with an end of the dialysis fluid line, wherein the control unit is configured to store in a memory connected to the control unit a volume or weight of fluid that is contained in each container of fresh fluid and in said waste container, wherein said volume or weight of fluid is detected by a sensor for each respective container, each sensor in operable communication with the control unit and sending to the control unit corresponding weight signals.

19. The apparatus of claim 16, wherein the control unit is configured to identify at least one container associated with at least one of (i) the set value for the fluid flow rate ($Q_{rep2}$) through the post-dilution infusion fluid line, (ii) the set value for the flow rate ($Q_{dial}$) of fluid supplied to the filtration unit secondary chamber through the dialysis fluid line, (iii) a set value for a fluid flow rate ($Q_{rep1}$) through a pre-dilution infusion fluid line, and calculate a reference time by dividing an initial weight or volume of the identified at least one container by the at least respective set flow rate value.

20. The apparatus of claim 16, wherein the apparatus comprises a separate scale detecting a weight of each respective container, the control unit is configured to compare a detected weight of each at least one container of fresh fluid to a respective threshold and to determine that at least one fresh fluid container is empty if the detected weight is below the respective threshold and/or the control unit is configured to compare the detected weight of a waste fluid container to a respective threshold and to determine that the waste container is full if the detected weight is above the threshold, the control unit is further configured to generate an empty container signal when the weight of one or more containers of fresh fluid is below the respective threshold and to generate a full container signal when the weight of said waste container is above the respective threshold.

21. The apparatus of claim 16, wherein the control unit is configured to calculate the set value of the fluid flow rate ($Q_{pbp}$) through the pre-blood pump infusion line based on a predefined algorithm, the flow rate ($Q_{pbp}$) through the pre-blood pump infusion line being proportional to the set value of the blood pump flow rate ($Q_{BLOOD}$), wherein the pre-blood infusion pump is a peristaltic pump, controlled by the control unit, acting on a segment of the pre-blood pump infusion line to regulate a pre-blood pump infusion rate ($Q_{pbp}$).

* * * * *